US011673938B2

(12) United States Patent
Henderson et al.

(10) Patent No.: US 11,673,938 B2
(45) Date of Patent: Jun. 13, 2023

(54) MUTANT G-PROTEIN COUPLED RECEPTORS AND METHODS FOR SELECTING THEM

(71) Applicant: Heptares Therapeutics Limited, Cambridge (GB)

(72) Inventors: Richard Henderson, Cambridge (GB); Christopher Gordon Tate, Cambridge (GB); Francesca Magnani, Cambridge (GB); Maria Josefa Serrano-Vega, Cambridge (GB); Yoko Shibata, Cambridge (GB); Antony Johannes Warne, Cambridge (GB); Malcolm Peter Weir, Cambridge (GB)

(73) Assignee: Heptares Therapeutics Limited, Cambridge (GB)

( * ) Notice: Subject to any disclaimer, the term of this patent is extended or adjusted under 35 U.S.C. 154(b) by 0 days.

(21) Appl. No.: 16/871,254

(22) Filed: May 11, 2020

(65) Prior Publication Data
US 2021/0061882 A1 Mar. 4, 2021

Related U.S. Application Data

(63) Continuation of application No. 16/215,533, filed on Dec. 10, 2018, now abandoned, which is a continuation of application No. 15/716,302, filed on Sep. 26, 2017, now abandoned, which is a continuation of application No. 14/836,820, filed on Aug. 26, 2015, now abandoned, which is a continuation of application No. 13/493,898, filed on Jun. 11, 2012, now abandoned, which is a continuation of application No. 12/450,358, filed as application No. PCT/GB2008/000986 on Mar. 20, 2008, now Pat. No. 8,785,135.

(30) Foreign Application Priority Data

Mar. 22, 2007 (GB) ..................................... 0705450
Dec. 8, 2007 (GB) ..................................... 0724052

(51) Int. Cl.
*C07K 14/72* (2006.01)
*C12N 15/10* (2006.01)
*G01N 33/566* (2006.01)

(52) U.S. Cl.
CPC ........ *C07K 14/723* (2013.01); *C12N 15/1034* (2013.01); *G01N 33/566* (2013.01); *G01N 2333/726* (2013.01)

(58) Field of Classification Search
CPC .............. C07K 14/723; C12N 15/1034; G01N 33/566; G01N 2333/726
See application file for complete search history.

(56) References Cited

U.S. PATENT DOCUMENTS

| | | | |
|---|---|---|---|
| 4,816,567 A | 3/1989 | Cabilly et al. |
| 4,946,778 A | 8/1990 | Ladner et al. |
| 5,223,409 A | 6/1993 | Ladner et al. |
| 5,290,681 A | 3/1994 | Kuroda et al. |
| 5,585,277 A | 12/1996 | Bowie et al. |
| 5,834,250 A | 11/1998 | Wells et al. |
| 5,925,549 A | 7/1999 | Hsueh et al. |
| 6,153,410 A | 12/2000 | Arnold et al. |
| 6,448,377 B1 | 9/2002 | Kobilka et al. |
| 6,537,749 B2 | 3/2003 | Kuimelis et al. |
| 6,692,696 B1 | 2/2004 | Alberte |
| 7,094,593 B1 | 8/2006 | Pausch et al. |
| 7,115,377 B2 | 10/2006 | Yao et al. |
| 7,294,472 B2 | 11/2007 | Gilchrist et al. |
| 7,462,457 B2 | 12/2008 | Beachy et al. |
| 7,998,694 B2 | 8/2011 | Trinquet et al. |
| 8,470,561 B2 | 6/2013 | Kobilka |
| 8,703,915 B2 | 4/2014 | Jazayeri-Dezfuly et al. |
| 8,748,182 B2 | 6/2014 | Heal et al. |
| 8,785,135 B2 | 7/2014 | Henderson et al. |
| 8,790,933 B2 | 7/2014 | Weir et al. |
| 8,900,591 B2 | 12/2014 | Hutchings et al. |
| 9,081,020 B2 | 7/2015 | Weir et al. |
| 9,260,505 B2 | 2/2016 | Weir et al. |
| 10,126,313 B2 | 11/2018 | Weir et al. |
| 10,174,101 B2 | 1/2019 | Jazayeri-Dezfuly et al. |
| 10,458,993 B2 | 10/2019 | Marshall et al. |
| 10,766,945 B2 | 9/2020 | Jazayeri-Dezfuly et al. |
| 2002/0028443 A1 | 3/2002 | Short |
| 2002/0147170 A1 | 10/2002 | Kopin et al. |
| 2003/0036092 A1 | 2/2003 | Iverson et al. |

(Continued)

FOREIGN PATENT DOCUMENTS

EP 0 184 187 A2 6/1986
EP 0 239 400 A2 9/1987

(Continued)

OTHER PUBLICATIONS

U.S. Appl. No. 60/080,686, filed Apr. 3, 1998, Kuimelis et al.
[No Author Listed] Uniprot Database Accession No. P08482. 1988. Muscarinic acetylcholine receptor M1.
[No Author Listed] Allergan and Heptares Announce Global R&D and Commercialization Partnership for Novel Treatments in Alzheimer's and Other Neurological Disorders. Press Release; Apr. 7, 2016. Last accessed from <https://www.heptares.com/index.php?mact=News,cntnt01,print,0&cntnt01articleid=268&cntnt01showtemplate=false&cntnt01returnid=74> on May 5, 2016.

(Continued)

*Primary Examiner* — Ruixiang Li
(74) *Attorney, Agent, or Firm* — Wolf, Greenfield & Sacks, P.C.

(57) ABSTRACT

The invention relates to mutant G-protein coupled receptors with increased conformational stability, and methods of use thereof. In some aspects, polynucleotides encoding the mutant G-protein coupled receptors are provided. In some aspects, host cells comprising the polynucleotides are provided. In some aspects, the invention relates to crystallized forms of the mutant G-protein coupled receptors, and methods of preparing the same.

3 Claims, 36 Drawing Sheets

Figure 1:
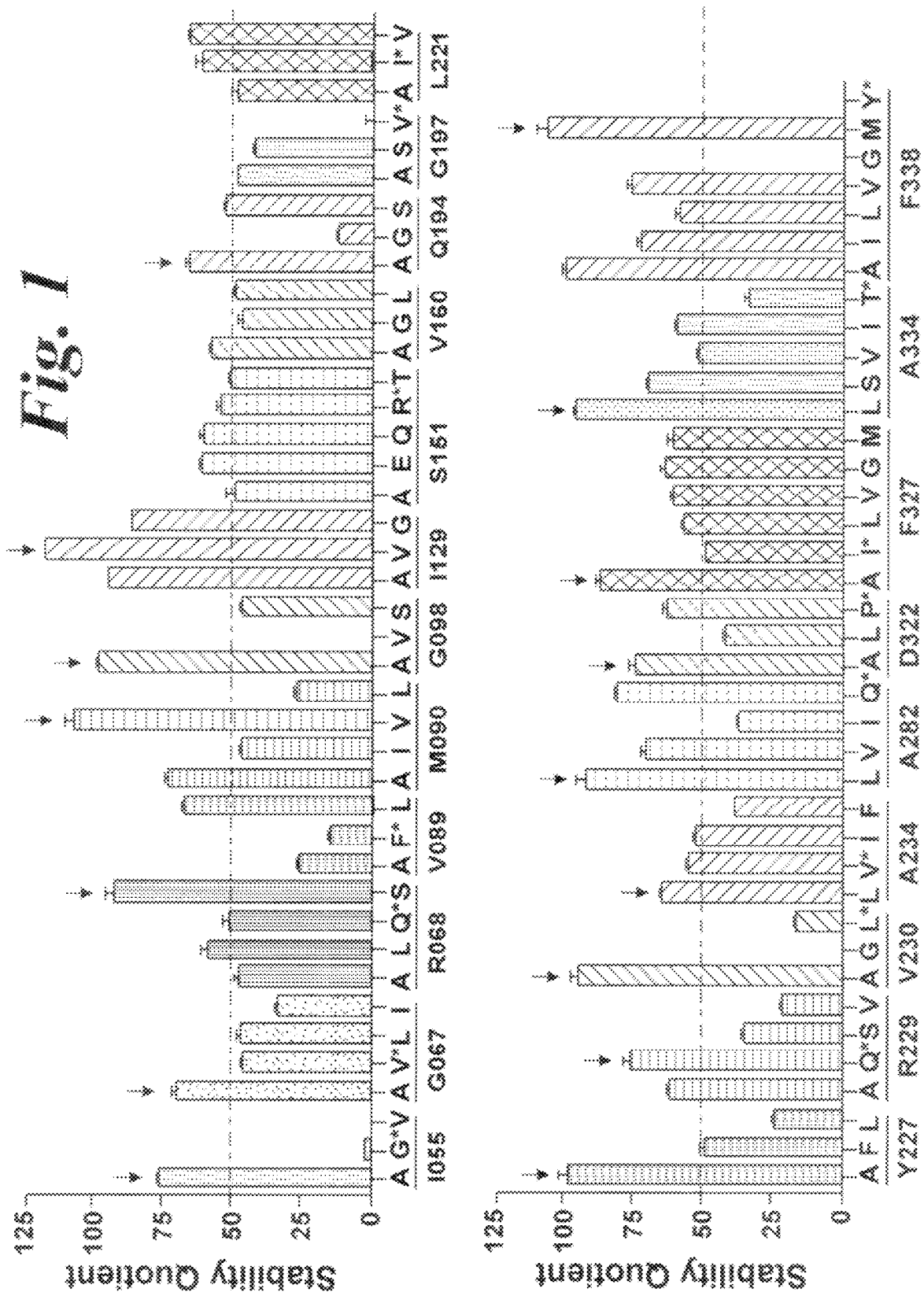

Specification includes a Sequence Listing.

(56) References Cited

U.S. PATENT DOCUMENTS

| | | |
|---|---|---|
| 2003/0096297 A1 | 5/2003 | Gilchrist et al. |
| 2003/0129649 A1 | 7/2003 | Kobilka et al. |
| 2003/0232331 A1 | 12/2003 | Gasman et al. |
| 2004/0157268 A1 | 8/2004 | Kobilka et al. |
| 2005/0136392 A1 | 6/2005 | Torres et al. |
| 2005/0143402 A1 | 6/2005 | Cheetham et al. |
| 2005/0287565 A1 | 12/2005 | Merchiers et al. |
| 2007/0154947 A1 | 7/2007 | Broach et al. |
| 2007/0196389 A1 | 8/2007 | Caligiuri et al. |
| 2010/0190188 A1 | 7/2010 | Henderson et al. |
| 2011/0027910 A1 | 2/2011 | Weir et al. |
| 2011/0028700 A1 | 2/2011 | Heal |
| 2011/0046351 A1 | 2/2011 | Weir et al. |
| 2011/0112037 A1 | 5/2011 | Warne et al. |
| 2012/0165507 A1 | 6/2012 | Jazayeri-Dezfuly et al. |
| 2012/0270230 A1 | 10/2012 | Henderson et al. |
| 2012/0288913 A1 | 11/2012 | Hanson et al. |
| 2013/0224238 A1 | 8/2013 | Hutchings et al. |
| 2014/0031525 A1 | 1/2014 | Robertson et al. |
| 2014/0315299 A1 | 10/2014 | Jazayeri-Dezful et al. |
| 2014/0316116 A1 | 10/2014 | Weir et al. |
| 2014/0357521 A1 | 12/2014 | Steyaert et al. |
| 2015/0147822 A1 | 5/2015 | Marshall et al. |
| 2015/0261911 A1 | 9/2015 | Bortolato et al. |
| 2016/0052991 A1 | 2/2016 | Henderson et al. |
| 2016/0327576 A1 | 11/2016 | Weir et al. |
| 2017/0145075 A1 | 5/2017 | Robertson et al. |
| 2018/0086814 A1 | 3/2018 | Henderson et al. |
| 2019/0094247 A1 | 3/2019 | Weir et al. |
| 2019/0112355 A1 | 4/2019 | Jazayeri-Dezfuly et al. |
| 2019/0241644 A1 | 8/2019 | Henderson et al. |
| 2021/0148939 A1 | 5/2021 | Weir et al. |

FOREIGN PATENT DOCUMENTS

| | | |
|---|---|---|
| EP | 0 397 834 B1 | 2/2000 |
| EP | 1 376 132 A1 | 1/2004 |
| EP | 1491207 A1 | 12/2004 |
| EP | 1 505 074 A1 | 2/2005 |
| GB | 2 188 638 A | 10/1987 |
| JP | 2002-510790 | 4/2002 |
| JP | 2004-238384 A | 8/2004 |
| JP | 2005-503124 A | 2/2005 |
| JP | 2005-515402 | 5/2005 |
| JP | 2006-506642 | 2/2006 |
| JP | 2006-340717 A | 12/2006 |
| JP | 2007-530919 | 11/2007 |
| JP | 2009-506336 A | 2/2009 |
| JP | 2011-224018 A | 11/2011 |
| JP | 2021-036901 A | 3/2021 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 95/32425 A1 | 11/1995 |
| WO | WO 97/35881 A2 | 10/1997 |
| WO | WO 99/51777 A2 | 10/1999 |
| WO | WO 00/22129 A1 | 4/2000 |
| WO | WO 2000/070343 A2 | 11/2000 |
| WO | WO 01/36471 A2 | 5/2001 |
| WO | WO 01/58916 A2 | 8/2001 |
| WO | WO 02/059346 A2 | 8/2002 |
| WO | WO 02/068600 A2 | 9/2002 |
| WO | WO 02/083736 A2 | 10/2002 |
| WO | WO 02/092833 A2 | 11/2002 |
| WO | WO 03/035693 A2 | 5/2003 |
| WO | WO 2004/046725 A2 | 6/2004 |
| WO | WO 2005/010532 A1 | 2/2005 |
| WO | WO 2005/121755 A1 | 12/2005 |
| WO | WO 2006/023248 A2 | 3/2006 |
| WO | WO 2008/068534 A2 | 6/2008 |
| WO | WO 2008/114020 A2 | 9/2008 |
| WO | WO 2009/051769 A1 | 4/2009 |
| WO | WO 2009/055512 A2 | 4/2009 |
| WO | WO 2009/071914 A2 | 6/2009 |
| WO | WO 2009/081136 A2 | 7/2009 |
| WO | WO 2012/030735 A1 | 3/2012 |
| WO | WO 2013/142278 A1 | 9/2013 |
| WO | WO 2014/028644 A1 | 2/2014 |

OTHER PUBLICATIONS

[No Author Listed] Guide to Pharmacology: G protein-coupled receptors. Last accessed from http://www.guidetopharmacology.org/GRAC/FamilyDisplayForward?familyId=694&familyType=GPCR on Apr. 12, 2018. 4 pages.

[No Author Listed] Heptares and Kymab enter Strategic Collaboration to Discover, Develop and Commercialise Novel Antibody Therapeutics. Press Release; Apr. 18, 2016. Last accessed from <https://www.heptares.com/index.php?mact=News,cntnl01,print,0&cntnt01articleid=269&cntnt01showtemplate=false&cntnt01returnid=74> on May 5, 2016.

[No Author Listed] Heptares Announces Publication in Nature of First Structure of Metabotropic Glutamate Receptor 5 Transmembrane Domain. Jul. 7, 2014. Last accessed at http://www.heptares.com/news/210/74/Heptares-Announces-Publication-In-Nature-Of-First-Structure-Of-Metabotropic-Glutamate-Receptor-5-Transmembrane-Domain.html on Jul. 31, 2014.

[No Author Listed] Heptares Awarded $5.5 Million Research & Development Grant from the US National Institute on Drug Abuse (NIDA). Press Release; Sep. 28, 2015. Last accessed from <https://www.heptares.com/index.php?mact=News,cntnl01,print,0&cntnt01articleid=252&cntnt01showtemplate=false&cntnt01returnid=74> on May 5, 2016.

[No Author Listed] Heptares Enters Strategic Drug Discovery Collaboration with Pfizer Inc. focused on GPCR Targets across Multiple Therapeutics Areas. Press Release; Nov. 30, 2015. Last accessed from <https://www.heptares.com/index.php?mact=News,cntnt01,print,0&cntnt01articleid=257&cntnt01showtemplate=false&cntnt01returnid=74> on May 5, 2016.

[No Author Listed] Heptares Press Release. Dec. 8, 2016. Heptares scientists solve structure of CCR9 chemokine receptor offering unique opportunity to apply structure-based design across chemokine receptor family. 2 pages.

[No Author Listed] Heptares Press Release. May 31, 2017. Heptares solves first full-length structure of GLP-1 receptor bound to peptide agonist. 2 pages.

[No Author Listed] Heptares Therapeutics press release. Jan. 23, 2015. Heptares Scientists to Receive the Malcolm Campbell Memorial Prize for 2015 in Recognition of Their Outstanding Contribution to GPCR Drug Discovery. 3 pages. Last accessed on Apr. 24, 2015 from http://www.prnewswire.com/news-releases/heptares-scientists-to-receive-the-malcolm-campbell-memorial-prize-for-2015-in-recognition-of-their-outstanding-contribution-to-gpcr-drug-discovery-289549371 .html.

[No Author Listed] Heptares Wins Best Established Biotech Company Award at OBN Annual Awards 2016. Press Release; Oct. 7, 2016. Last accessed from <https://www.heptares.com/index.php?mact=News,cntnt01,print,0&cntnt01articleid=278&cntnt01showtemplate=false&cntnt01returnid=74> on May 31, 2017.

[No Author Listed] IUPHAR database. G protein-coupled receptors. Available at http://www.iuphar-db.org/GPCR/ReceptorFamiliesForward. Downloaded Apr. 28, 2010.

[No Author Listed] Stephen White Laboratory at UC Irvine. Available at http://blanco.biomol.uci.edu. Downloaded May 29, 2012.

[No Author Listed] Teva and Heptares Enter Agreement to Discover and Develop Novel, Small-Molecule CGRP Antagonists for Treatment of Migraine. Press Release; Nov. 25, 2015. Last accessed from <https://www.heptares.com/index.php?mact=News,cntnt01,print,0&cntnt01articleid=256&cntnt01showtemplate=false&cntnt01returnid=74> on May 5, 2016.

[No Author Listed] The CCP4 suite: programs for protein crystallography. Collaborative Computational Project, No. 4. Acta Crystallogr. 1994. D50:760-763.

(56) References Cited

OTHER PUBLICATIONS

[No Author Listed] The Nobel Prize in Chemistry 2012. Press Release; Oct. 10, 2012. Last accessed from <https://www.nobelprize.org/nobe_prizes/chemistry/laureates/2012/press.html> on Nov. 29, 2012.
[No Author Listed] Uniprot Database Accession No. P43220. 1995.
Abagyan et al., High-throughput docking for lead generation. Curr. Opin. Chem. Biol. 2001. 5:375-382.
Abagyan et al., ICM—a new method for protein modelling and design. Applications to docking and structure prediction from the distorted native conformation. J. Comput. Chem. 1994. 15:488-506.
Adams et al., PHENIX: building new software for automated crystallographic structure determination. Acta Crystallogr. 2002. D58:1948-1954.
Afonine et al., The Phenix refinement framework. CCP Newsletter. 2005. Contribution 8.
Alberts et al., Solubilizing membrane proteins with a mild detergent. Molecular Biology of the Cell. 2002;4th Edition. New York: Garland Science. Figure 10-24.
Alexandrov et al., Microscale Fluorescent Thermal Stability Assay for Membrane Proteins; Structure; 2008;16:351-359.
Ali et al., Membrane Protein Crystallization in Lipidic Mesophases: Detergent Effects. Biophys. J. 2000.79:394-405.
Alkhatib et al., HIV coreceptors: from discovery and designation to new paradigms and promise. Eur. J. Med. Res. 2007 12(9):375-384.
Altschul et al., Basic local alignment search tool. J. Mol. Biol. 1990. 215:403-410.
Altschul et al., Gapped BLAST and PSI-BLAST: a new generation of protein database search programs. Nucl Acids Res. 1997 25:3389-3402.
Altschul et al., Local alignment statistics. Methods in Enzymology. 1996. 266:460-480.
Alves et al., Plasmon Resonance Methods in GPCR Signaling and Other Membrane Events. Curr. Prot. & Peptide Sci. 2005 6:293-312.
Artymiuk et al., Graph theoretic methods for the analysis of structural relationships in biological macromolecules. J Amer. Soc. Info. Sci Tech. 2005 56(5):518-528.
Ault et al., Creation of GPCR-based chemical sensors by directed evolution in yeast. Protein Eng Des Sel. Jan. 2006;19(1):1-8.
Avlani et al., Critical role for the second extracellular loop in the binding of both orthosteric and allosteric G protein-coupled receptor ligands. J Biol Chem. 2007. 282:25677-25686.
Babcook et al., A novel strategy for generating monoclonal antibodies from single, isolated lymphocytes producing antibodies of defined specificities. PNAS. 1996 93:7843-7848.
Baker, The selectivity of β-adrenoceptor antagonists at the human β1, β2 and β3 adrenoceptors. British J. Pharmacol. 2005. 144:317-322.
Bakker et al., Constitutively Active Mutants of the Histamine H1 Receptor Suggest a Conserved Hydrophobic Asparagine-Cage That Constrains the Activation of Class A G Protein-Coupled Receptors. Mol. Pharmacol. 2008. 73:94-103.
Balbes et al., A Perspective of Modern Methods in Computer-Aided Drug Design. Reviews in Computational Chemistry. 1994. 5:337-380.
Baldwin et al., An alpha-carbon template for the transmembrane helices in the rhodopsin family of G-proteincoupled receptors. J. Mol. Biol. 1997. 272:144-164.
Ballesteros et al., Activation of the beta 2-adrenergic receptor involves disruption of an ionic lock between the cytoplasmic ends of transmembrane segments 3 and 6. J. Biol. Chem. 2001. 276:29171-29177.
Ballesteros et al., Integrated methods for the construction of three-dimensional models and computational probing of structure-function relations in G-protein coupled receptors. Methods in Neurosciences. 1995 Sealfon, S.C.and Conn, P.M. (eds.). Academic Press San Diego, CA 366-428.
Ballesteros et al., Structural mimicry in GPCR: Implications of the high-resolution structure of rhodopsin for structure-function analysis of rhodopsin-like receptors. Mol. Pharmacology 60, 1-19, 2001.
Bamber et al., Yeast mitochondrial ADP ATP carriers are monomeric in detergents. PNAS. 2006 103:16224-16229.
Baneres et al., Molecular Characterization of a Purified 5-HT4 Receptor. J. Biol. Chem. 2005. 208:20253-20260.
Baranski et al., C5a Receptor Activation. J. Biol. Chem. 1999. 274(22):15757-15765.
Barbas et al., Assembly of combinatorial antibody libraries on phage surfaces: The gene III site. PNAS. 1991 88:7978-7982.
Baroni et al., A Common Reference Framework for Analyzing/Comparing Proteins and Ligands. Fingerprints for Ligands And Proteins (FLAP): Theory and Application. J. Chem Inf. Mod. 2007. 47:279-294.
Barroso et al., 2000, Identification of Residues Involved in Neurotensin Binding and Modeling of the Agonist Binding Site in Neurotensin Receptor 1, Journal of Biological Chemistry, 275(1):328-336.
Barroso et al., 2002, Constitutive activation of the neurotensin receptor 1 by mutation of Phe358 in Helix seven, British Journal of Pharmacology, 135:997-1002.
Barroso, Constitutive activation of the neurotensin receptor 1 by mutation of Phe(358) in Helix seven. Br J Pharmacol. Feb. 2002;135(4):997-1002.
Barry et al., Quantitative protein profiling using antibody arrays. Proteomics. 2004 4:3717-3726.
Bartlett et al., CAVEAT: A Program to Facilitate the Structure-Derived Design of Biologically Active Molecules. Molecular Recognition: Chemical and Biological Problems, 1989. S. M. Roberts, Editor, Royal Society of Chemistry. 78:182-196.
Bee et al., Functional analysis of transmembrane domain 2 of the M1 muscarinic acetylocholine receptor, J. Biol. Chem. 2007;282(44):32471-32479.
Behr et al., Novel mutants of the human β1-adrenergic receptor reveal amino acids relevant for receptor activation. J. Biol. Chem. 2006. 281(26):18120-18125.
Berchiche et al., Direct Assessment of CXCR4 Mutant Conformations Reveals Complex Link between Receptor Structure and G(alpha)(i) Activation. J. Biol. Chem. 2007. 282(8):5111-5115.
Besenicar et al., Surface plasmon resonance in protein-membrane interactions. Chem. Phys. Lipids. 2006 141:169-178.
Black, Drugs from Emasculated Hormones: The Principle of Syntopic Antagonism (Nobel Lecture). Angew Chem. Int. Edit. 1989. 28:886-894.
Blundell et al., Knowledge-based prediction of protein structures and the design of novel molecules. Nature. 1987. 326:347-352.
Blundell et al., Knowledge-based protein modelling and design; 18th Sir Hans Krebs Lecture Eur. J. Biochem. 1988. 173:513-520.
Bockaert et al., GPCR-GIP networks: a first step in the discovery of new therapeutic drugs? Curr Opin Drug Discov and Dev. 2004. 7:649-657.
Bockaert et al., Molecular tinkering of G protein-coupled receptors: an evolutionary success. EMBO J. 1999. 18:1723-1729.
Boehm et al., Chemical Probe Identification Platform for Orphan GPCRs Using Focused Compound Screening: GPR39 as a Case Example. ACS Med Chem Lett. Sep. 16, 2013;4(11):1079-84. doi: 10.1021/ml400275z. eCollection Nov. 14, 2013.
Bohm. The computer program LUDI: a new method for the de novo design of enzyme inhibitors. J. Comput. Aided Mol. Des. 1992. 6:61-78.
Bommarius et al., High-throughput screening for enhanced protein stability. Curr Opin Biotechnol. 2006. 17(6):606-610. Epub Oct. 17, 2006.
Bonner et al., Identification of a family of muscarinic acetylcholine receptor genes. Science. 1987. 237:527-532.
Boucard et al., Constitutive Activation of the Angiotensin II Type 1 Receptor Alters the Spatial Proximity of Transmembrane 7 to the Ligand-binding Pocket. J. Biol. Chem. 2003. 278(38):36628-36636. Epub Jul. 3, 2003.
Bowie, Stabilizing membrane proteins. Curr. Opin. Struct. Biol. 2001. 11(4):397-402.
Brenner et al., Encoded combinatorial chemistry. PNAS. 1992. 89:5381-5383.
Brodeur et al., Mouse-Human Myeloma Partners for the Production of Heterohybridomas. Mono. Antib. Prod. Tech. Apps. 1987. 51-63.

(56) References Cited

OTHER PUBLICATIONS

Brunger et al., Recent developments for the efficient crystallographic refinement of macromolecular structures. Curr. Opin. Struct. Biol. 1998. 8(5):606-611.
Bruns et al., Human glutathione transferase A4-4 crystal structures and mutagenesis reveal the basis of high catalytic efficiency with toxic lipid peroxidation products. J Mol Biol. 1999. 288:427-439.
Burstein et al., The second intracellular loop of the m5 muscarinic receptor is the switch which enables G-protein coupling. J Biol Chem. 1998. 273:24322-24327.
Caron et al., Affinity chromatography of the beta-adrenergic receptor. J. Biol. Chem.1979. 254:2923-2927.
Carrillo et al., The multiple sequence alignment problem in biology. SIAM J. Appl. Math. 1988;48:1073-1082.
Carson, Ribbons 2.0. Appl. Crystallogr. 1991. 24:958-961.
Chan et al., Allosteric modulation of the muscarinic M4 receptor as an approach to treating schizophrenia. PNAS. 2008. 105:10978-10983.
Chapple et al., Multiplexed expression and screening for recombinant protein production in mammalian cells. BMC Biotechnol. 2006. 22:6-49.
Cherezov et al., A robotic system for crystallizing membrane and soluble proteins in lipidic mesophases. Acta. Crystallogr. D. Biol. Crystallogr. 2004. 60(Pt 10):1795-1807. Epub Sep. 23, 2004.
Cherezov et al., Crystallization Screens: Compatibility with the Lipidic Cubic Phase for in Meso Crystallization of Membrane Proteins. Biophys. J. 2001. 81:225-242.
Cherezov et al., High Resolution Crystal Structure of an Engineered Human β2-Adrenergic G protein-Coupled Receptor. Science. 2007. 318(5854):1258-1265. Epub Oct. 25, 2007.
Cherezov et al., Room to Move: Crystallizing Membrane Proteins in Swollen Lipidic Mesophases. J. Mol. Biol. 2006. 357:1605-1618.
Christopoulos, Allosteric binding sites on cell-surface receptors: Novel targets for drug discovery. Nat. Rev. Drug Discov. 2002. 1:198-210.
Chun et al., Fusion Partner Toolchest for the Stabilization and Crystallization of G Protein-Coupled Receptors. Structure. Jun. 2012;20(6):967-76.
Chung et al., Orphan GPCR research. Br J Pharmacol. Mar. 2008;153 Suppl 1:S339-46. Epub Dec. 10, 2007.
Clackson et al., Making antibody fragments using phage display libraries. Nature. 1991. 352:624-628.
Claeysen et al., A single mutation in the 5-HT4 receptor (5-HT4-R D100(3.32)A) generates a Gs-coupled receptor activated exclusively by synthetic ligands (RASSL).J Biol Chem. Jan. 10, 2003;278(2):699-702. Epub Nov. 18, 2002.
Cohen et al., Molecular modeling software and methods for medicinal chemistry. J. Med. Chem. 1990. 33:883-894.
Conklin et al., Engineering GPCR signaling pathways with RASSLs. Nat Methods. Aug. 2008;5(8):673-8.
Cooper. Advances in membrane receptor screening and analysis. J. Mol. Recognit. 2004. 17(4):286-315.
Cooper. Non-optical screening platforms: the next wave in label-free screening? Drug Discov. Today. 2006. 11(23-24):1068-1074. Epub Oct. 20, 2006.
Cornell et al., A Second Generation Force Field for the Simulation of Proteins, Nucleic Acids, and Organic Molecules. JACS. 1995. 117(19):5179-5197.
D'Antona et al., A cannabinoid receptor 1 mutation proximal to the DRY motif results in constitutive activty and reveals intramolecular interactions involved in receptor activation. Brain Research. 2006 1108(1):1-11.
D'Antona et al., Mutations of CB1 T210 Produce Active and Inactive Receptor Forms: Correlations with Ligand Affinity, Receptor Stability, and Cellular Localization. Biochemistry. 2006. 45:5606-5617.
Day et al., A monoclonal antibody for G protein-coupled receptor crystallography. Nat Methods. 2007. 4(11):927-929.
Degrip. Thermal Stability of Rhodopsin and Opsin in Some Novel Detergents. Methods in Enzymology. 1982. 81:256-265.

Devereux et al., A comprehensive set of sequence analysis programs for the VAX; Nucl. Acids Rec. 12:387-395, 1984.
Dignam. Preparation of extracts from higher eukaryotes. Methods in Enzymology. 1990. 182:194-203.
Domazet et al., The second transmembrane domain of the human type 1 angiotensin II receptor participates in the formation of the ligand binding pocket and undergoes integral pivoting movement during the process of receptor activation. J Biol Chem. May 1, 2009 ;284(18):11922-9. Epub Mar. 9, 2009.
Doré et al., Structure of class C GPCR metabotropic glutamate receptor 5 transmembrane domain. Nature. Jul. 31, 2014;511(7511):557-62. doi: 10.1038/nature13396. Epub Jul. 6, 2014.
Doré et al., Structure of the adenosine A(2A) receptor in complex with ZM241385 and the xanthines XAC and caffeine. Structure. Sep. 7, 2011;19(9):1283-93. doi: 10.1016/j.str.2011.06.014.
Dupriez et al. Aequorin-based functional assays for G-protein-coupled receptors, ion channels and tyrosine kinase receptors. Receptors Channels. 2002. 8(5-6):319-330.
Duthey et al., A single subunit (GB2) is required for G-protein activation by the heterodimeric GABA(B) receptor. J Biol Chem. Feb. 1, 2002;277(5):3236-41. Epub Nov. 15, 2001.
Dyson et al., Identification of soluble protein fragments by gene fragmentation and genetic selection. Nucl. Acid Research. 2008. 36:e51.
Dyson et al., Production of soluble mammalian proteins in *Escherichia coli*: identification of protein features that correlate with successful expression. BMC Biotechnology. 2004. 4:32.
Eddy et al., Maximum Discrimination Hidden Markov Models of Sequence Consensus. J. Comput Biol. 1995. 2(1):9-23.
Eglen. Functional G protein-coupled receptor assays for primary and secondary screening. Comb. Chem. High Throughput Screen. 2005. 8(4):311-318.
Eisen et al., HOOK: a program for finding novel molecular architectures that satisfy the chemical and steric requirements of a macromolecule binding site. Proteins:Structure, Function and Genetics. 1994.19(3):199-221.
Eldridge et al., Empirical scoring functions: I. the development of a fast empirical scoring function to estimate the binding affinity of ligands in receptor complexes. J. Comp. Aided Mol. Des. 1997. 11(5):425-445.
Ernst et al., Intrinsic biophysical monitors of transducin activation: fluorescence, UV-visible spectroscopy, light scattering, and evanescent field techniques. Meth. Enzymol. 2000. 315:471-489.
Evans et al., An introduction to molecular replacement. Acta Crystallogr. 2008. D64:1-10.
Faham et al., Side-chain contributions to membrane protein structure and stability. J. Mol. Biol. 2004. 335:297-305.
Fanelli. Theoretical study on mutation-induced activation of the luteinizing hormone receptor. J. Mol. Biol. 2000. 296(5):1333-1351.
Fang et al., G protein-coupled receptor microarrays for drug discovery. Drug Discovery Today. 2003. 8:755-761.
Felix et al., Immunoadsorption as a new therapeutic principle for treatment of dilated cardiomyopathy. Eur. Heart J. Supplements. 2002. 4:I63-I68.
Ferracci et al., Real time analysis of intact organelles using surface plasmon resonance. Anal. Biochem. 2004. 334:367-375.
Ferro et al., A different best rigid body molecular fit routine. Acta Cryst. 1977. A33:345-347.
Fetrow et al., New programs for protein tertiary structure prediction. Biotechnology. 1993. 11(4):479-484.
Flanagan, A GPCR that is not "DRY". Mol Pharmacol. Jul. 2005;68(1):1-3. Epub Apr. 26, 2005.
Folkertsma et al., A family-based approach reveals the function of residues in the nuclear receptor ligand-binding domain. J. Mol. Biol. 2004. 341(2):321-335.
Foord et al., International Union of Pharmacology. XLVI. G Protein-Coupled Receptor List. Pharmacol. Rev. 2005. 57:279-288.
Foord et al., RAMPs: accessory proteins for seven transmembrane domain receptors, Trends Pharmacol Sci. 20(5):184-187 1999.
Frändberg et al., Cysteine Residues are Involved in Structure and Function of Melanocortin 1 Receptor: Substitution of a Cysteine

(56) References Cited

OTHER PUBLICATIONS

Residue in Transmembrane Segment Two Converts an Agonist to Antagonist. Biochem. Biophys. Res. Commun. 2001. 281(4):851-857.
Frielle et al., Cloning of the cDNA for the human-β-adrenergic receptor. PNAS. 1987. 84:7920-7924.
Fuchs et al., Targeting recombinant antibodies to the surface of *Escherichia coli*: fusion to a peptidglycan associated lipoprotein. Biotechnology. 1991. 9:1369-1372.
Gales et al., Real-time monitoring of receptor and G-protein interactions in living cells, Nat. Methods. 2(3):177-184 (2005).
Garcia-Lopez et al., Strategies for design of non peptide CCK1R agonist/antagonist ligands. Curr. Top. Med. Chem. 2007. 7(12):1180-1194.
Gardella et al., Transmembrane residues of the parathyroid hormone (PTH)/PTH-related peptide receptor that specifically affect binding and signaling by agonist ligands. J Biol Chem. May 31, 1996;271(22):12820-5.
Garippa et al., High-throughput confocal microscopy for beta-arrestin-green fluorescent protein translocation G protein-coupled receptor assays using the Evotec Opera Methods Enzymol. 2006;414:99-120.
Garrard et al., Fab assembly and enrichment in a monovalent phage display system. Biotechnology. 1991. 9:1373-1377.
Gerber et al., An Activation Switch in the Ligand Binding Pocket of the C5a Receptor. J. Biol. Chem. 2001. 276(5):3394-3400.
Gether et al., Structural Instability of a Constitutively Active G Protein-coupled Receptor Agonist-Independent Activation Due to Conformational Flexibility. J. Biol. Chem. 1997. 272:2587-2590.
Gether. Uncovering Molecular Mechanisms Involved in Activation of G Protein-Coupled Receptors. Endocr. Rev. 2000. 21:90-113.
Ghanouni et al., The effect of pH on beta(2) adrenoceptor function. Evidence for protonation-dependent activation. J Biol Chem. Feb. 4, 2000;275(5):3121-7.
Gillet et al., SPROUT—a program for structure generation. J. Comput. Aided Mol. Des.1993. 7:127-153.
Ginalski, Comparative modeling for protein structure prediction. Curr. Op. Struct. Biol. 2006. 16(2):172-177.
Gish et al., Identification of protein coding regions by database similarity search. Nature Genetics. 1993. 3:266-272.
Goding. Production of Monoclonal Antibodies: Principles and Practice. Academic Press. 1986. 59-103.
González et al., Cellular fluorescent indicators and voltage/ion probe reader (VIPR) tools for ion channel and receptor drug discovery. Receptors Channels. 2002;8(5-6):283-95.
Goodford. A Computational Procedure for Determining Energetically Favorable Binding Sites on Biologically Important Macromolecules. J. Med. Chem. 1985. 28:849-857.
Goodsell et al., Automated docking of substrates to proteins by simulated annealing. Proteins: Structure, Function and Genetics. 1990. 8:195-202.
Gram et al., In vitro selection and affinity maturation of antibodies from a naïve combinatorial immunoglobulin library. PNAS. 1992. 89:3576-3580.
Graneli et al., Characterization of a proton pumping transmembrane protein incorporated into a supported three-dimensional matrix of proteoliposomes. Anal. Biochem. 2007. 367:87-94.
Graneli et al., Utilizing adsorbed proteoliposomes trapped in a non-ruptured state on SiO2 for amplified detection of membrane proteins. Biosens. Bioelectron. 2004. 20:498-504.
Gray et al., Identification of Two Serine Residues Essential for Agonist-Induced 5-HT2a Receptor Desensitization. Biochemistry. 2003. 42(36):10853-10862.
Gray. High-resolution protein-protein docking. Curr. Opin. Struct. Biol. 2006. 16:183-193.
Greer et al., Application of the Three-Dimensional Structures of Protein Target Molecules in Structure-Based Drug Design. J. Med. Chem. 1994. 37:1035-1054.
Greer. Comparative modeling of homologous proteins. Methods in Enzymology. 1991. 202:239-252.
Greer. Model structure for the inflammatory protein C5a. Science. 1985. 228:1055-1060.
Griffiths et al. Human anti-self antibodies with high specificity from phage display libraries. EMBO J. 1993. 12:725-734.
Grindley et al., Identification of Tertiary Structure Resemblance in Proteins Using a Maximal Common Subgraph Isomorphism Algorithm. J. Mol. Biol. 1993. 229:707-721.
Grisshamer et al. Expression of a rat neurotensin receptor in *Escherichia coli*. Biochem J. 1993. 295(2):571-576.
Grisshammer et al., Overexpression of integral membrane proteins for structural studies. Q. Rev. Biophys. 1995. 28:315-422.
Groves et al., Supported planar bilayers in studies on immune cell adhesion and communication. Immunol. Meth. 2003. 278:19-32.
Groves. Membrane array technology for drug discovery. Curr. Op. Drug Discov. Develop. 2002. 5:606-612.
Gschwend et al., Orientational sampling and rigid-body minimization in molecular docking revisited: on-the-fly optimization and degeneracy removal. J. Comput. Aided Mol. Des. 1996. 10:123-132.
Guida. Software for structure-based drug design. Curr. Opin. Struct. Biol. 1994. 4:777-781.
Gupta et al., Conformation State-sensitive Antibodies to G-protein-coupled Receptors. J. Biol. Chem. 2007. 282(8): 5116-5124.
Gupta et al., The use of receptor-specific antibodies to study G-protein-coupled receptors. Mt. Sinai J. Med. 2006. 73(4):673-681.
Halperin et al., Principles of docking: An overview of search algorithms and a guide to scoring functions. Proteins. 2002. 47:409-443.
Hamuro et al., Hydrogen/deuterium-exchange (H/D-Ex) of PPARγ LBD in the presence of various modulators. Protein Science. 2006. 15(8):1883-1892.
Han et al., Constitutive activation of opsin by mutation of methionine 257 on transmembrane helix 6. Biochemistry. Jun. 2, 1998;37(22):8253-61.
Harding et al., Direct analysis of a GPCR-agonist interaction by surface plasmon resonance. Eur. Biophys. J. Biophys. Let. 2006. 35:709-712.
Hawkins et al., Selection of phage antibodies by binding affinity: mimicking affinity maturation. J. Mol. Biol. 1992. 226:889-896.
Hay et al., Bacteriophage Cloning and *Escherichia coli* Expression of a Human IgM Fab. Hum. Antibod. Hybridomas. 1992. 3:81-85.
Hendrickson. Transformations to optimize the superposition of similar structures. Acta Crystallogr. 1979. A35:158-163.
Henikoff et al., Amino acid substitution matrices from protein blocks. Proc Natl Acad Sci U.S.A. Nov. 15, 1992; 89(22):10915-10919.
Heydenreich et al., Stabilization of G protein-coupled receptors by point mutations. Front. Pharmacol. Apr. 20, 2015;6:82. doi: 10.3389/fphar.2015.00082. eCollection 2015.
Hoffmann et al., A FlAsH-based FRET approach to determine G protein-coupled receptor activation in living cells. Nat Methods. Mar. 2005;2(3):171-6. Epub Feb. 17, 2005.
Hohenstein et al., Structure of class B GPCR corticotropin-releasing factor receptor 1. Nature. Jul. 25, 2013;499(7459):438-43. doi: 10.1038/nature12357. Epub Jul. 17, 2013.
Holm et al., Dali/FSSP classification of three-dimensional protein folds. Nucl. Acids Res. 1997. 25:231-234.
Holm et al., Mapping the Protein Universe. Science. 1996. 273:595-602.
Hoogenboom et al., Multi-subunit proteins on the surface of filamentous phage: methodologies for displaying antibody (Fab) heavy and light chains. Nuc. Acid Res. 1991. 19:4133-4137.
Hopkins et al., The druggable genome. Nature Rev. Drug Discovery. 2002. 1:727-730.
Hoppe et al., Prediction of protein thermostability with a direction- and distance-dependent knowledge-based potential. Protein Science. 2005. 14:2682-2692.
Hu et al., Identification of Surrogate Agonists and Antagonists for Orphan G-Protein-Coupled Receptor GPR139. J Biomol Screen. Aug. 2009;14(7):789-97.
Huang et al., A probabilistic method to correlate ion pairs with protein thermostability. Applied Bioinformics. 2004. 3(1):21-29.

(56) References Cited

OTHER PUBLICATIONS

Huang et al., Discovery of human antibodies against the C5aR target using phage display technology. J Mol Recognit. Jul.-Aug. 2005;18(4):327-33.

Hubbell et al., Rhodopsin structure, dynamics, and activation: a perspective from crystallography, site-directed spin labeling, sulfhydryl reactivity, and disulfide cross-linking. Adv. Protein Chem. 2003. 63:243-290.

Hudson et al., High-content screening of known G protein-coupled receptors by arrestin translocation. Methods Enzymol. 2006;414:63-78.

Hulme et al., Purification of recombinant M1 muscarinic acetylcholine receptor. Biochemical Society Transactions. 1998. 26:S361.

Hulme et al., Phenotypic classification of mutants: a tool for understanding ligand binding and activation of muscarinic acetylcholine receptors. Biochem Soc Trans. Aug. 2007;35(Pt 4):742-5.

Hunte et al., Structure at 2.3 Å resolution of the cytochrome bc1 complex from the yeast *Saccharomyces cerevisiae* co-crystallized with an antibody Fv fragment. Structure. 2000. 8:669-684.

Hus et al. Assignment strategy of proteins with known structure. J. Magn. Reson. 2002. 157(1):119-123.

Huse et al., Generation of a large combinatorial library of the immunoglobulin repertoire in phage lambda. Science. 1989. 246:1275-1281.

Ikuta et al., Crystallographic Approach to Identification of Cyclin-dependent Kinase 4 (CDK4)-specific Inhibitors by Using CDK4 Mimic CDK2 Protein. J. Biol. Chem. 2001. 276:27548-27554.

Isogaya et al., Binding pockets of the β1 and β2 adrenergic receptors for subtype-selective agonists. Mol. Pharmacol. 1999. 56(5):875-885.

Isogaya et al., Identification of a Key Amino Acid of the β2-Adrenergic Receptor for High Affinity Binding of Salmeterol. Mol. Pharmacol. 1998. 54:616-622.

Jaakola et al., The 2.6 Å Crystal Structure of a Human A2A Adenosine Receptor Bound to an Antagonist. Science. 2008. 322:1211-1217.

Jacob et al., Virtual screening of GPCRs: An in silico chemogenomics approach. BMC Bioinformatics. Sep. 6, 2008;9:363. doi: 10.1186/1471-2105-9-363.

Jaenicke et al., The stability of proteins in extreme environments. Current Opinion in Structural Biology. 1998. 8:738-748.

Jahns et al., Direct evidence for a β1-adrenergic receptor-directed autoimmune attack as a cause of idiopathic dilated cardiomyopathy. J. Clinical Investigation. 2004. 113(10):1419-1429.

Jahns et al., Modulation of Beta1-Adrenoceptor Activity by Domain-Specific Antibodies and Heart Failure-Associated Autoantibodies. J. Am. Coll. Cardiol. 2000. 36(4):1280-1287.

Jameson et al., Real-time Detection of Basal and Stimulated G Protein GTPase Activity Using Fluorescent GTP Analogues. J. Biol. Chem. 2005. 280(9):7712-7719.

Jane-wit et al., β1-Adrenergic Receptor Autoantibodies Mediate Dilated Cardiomyopathy by Agonistically Inducing Cardiomyocyte Apoptosis. Circulation. 2007. 116(4):399-410. Epub Jul. 9, 2007.

Jap et al., 2D crystallization: from art to science; Ultramicroscopy. 1992. 46(1-4):45-84.

Jazayeri et al., Extra-helical binding site of a glucagon receptor antagonist. Nature. Apr. 25, 2016;533(7602):274-7. doi: 10.1038/nature17414.

Jerne et al., Plaque formation in agar in single antibody-producing cells. Science. 1963. 140:405.

Johnson et al., A 1,536-well 35S GTPgammaS scintillation proximity binging assay for ultra-high-throughput screening of an orphan galphai-coupled GPCR. Assay Drug Dev Technol 6, 327-337 (2008).

Johnson et al., Human antibody engineering. Curr. Op. Structural Biol. 1993. 3:564-571.

Johnson et al., Knowledge-based protein modeling. Crit Rev Biochem Mol Biol. 1994. 29:1-68.

Jones et al., Development and validation of a genetic algorithm for flexible docking. J Mol. Biol. 1997. 267:727-748.

Jones et al., Docking small-molecule ligands into active sites. Curr. Opin. Biotech. 1995. 6:652-656.

Jones et al., Improved methods for building protein models in electron density maps and the location of errors in these models. Acta Crystallogr. 1991. A47:110-119.

Jones et al., Molecular Recognition of Receptor Sites Using a Genetic Algorithm with a Description of Desolvation. J Mol Biol. 1995. 245:43-53.

Kabsch, A discussion of the solution for the best rotation to relate two sets of vectors. Acta Crystallogr. 1978. A34:827-828.

Kabsch., A solution of the best rotation to relate two sets of vectors. Acta Crystallogr. 1976. A32:922-23.

Karlin et al., Applications and statistics for multiple high-scoring segments in molecular sequences. PNAS. 1993. 90:5873-5877.

Karlsson et al., Flow-Mediated On-Surface Reconstitution of G-Protein Coupled Receptors for Applications in Surface Plasmon Resonance Biosensors. Anal. Biochem. 2002. 300(2):132-138.

Kearsley. On the orthogonal transformation used for structural comparisons. Acta Crystallogr. 1989. A45:208-210.

Kenakin et al., Protean agonists. Keys to active receptor states? Ann. N.Y. Acad. Sci. 1997. 812:116-125.

Kenakin. Inverse, protean, and ligand-selective agonism: matters of receptor conformation. FASEB J. 2001. 15(3):598-611.

Kent et al., Development of a Generic Dual-Reporter Gene Assay for Screening G-Protein-Coupled Receptors. J. Biomol. Screen. 2005. 10(5):437-446.

Kent et al., G-protein-coupled receptor heterodimerization: assay technologies to clinical significance. Curr. Opin. Drug Discov. Devel. 2007. 10(5):580-589.

Kerr et al., Encoded combinational peptide libraries containing non-natural amino acids. JACS. 1993. 115:2529-2531.

Kikkawa et al., The Role of the Seventh Transmembrane Region in High Affinity Binding of a b2-Selective Agonist TA-2005. Mol. Pharmacol. 1998. 53:128-134.

Kinoshita, [Application and development of structure-based drug design using X-ray analysis]. Nihon Yakurigaku Zasshi. Mar. 2007;129(3):186-90.

Kitabgi et al., Functional domains of the subtype 1 neurotensin receptor (NTS1).Peptides. Oct. 2006;27(10):2461-8. Epub Aug. 9, 2006.

Klabunde et al., Chemogenomics approaches to G-protein coupled receptor lead finding. Ernst Schering Res Found Workshop. 2006;58:31-46.

Klco et al., Essential role for the second extracellular loop in C5a receptor activation. Nat Struct Mol Biol. 2005. 12:320-326.

Kleywegt et al., A super position. CCP4/ESF-EACBM Newsletter on Protein Crystallography. 1994. 31:9-14.

Kobilka et al., Conformation complexity of G-protein coupled receptors. Trends in Pharmacological Sciences. 2007. 28(8):397-406.

Kobilka et al., New G-protein-coupled receptor crystal structures: insights and limitations. Trends Pharm. Sci. 2008. 29(2):79-83.

Köhler et al., Continuous cultures of fused cells secreting antibody of predefined specificity. Nature. 1975. 256:495-497.

Komolov et al., Surface Plasmon Resonance Study of G Protein/Receptor Coupling in a Lipid Bilayer-Free System. Anal. Chem. 2006. 78:1228-1234.

Kostenis, G Proteins in Drug Screening: From Analysis of Receptor-G Protein Specificity to Manipulation of GPCR-Mediated Signaling Pathways. Curr Pharm Des. 2006;12(14):1703-15.

Kozbor et al., A human hybrid myeloma for production of human monoclonal antibodies. J. Immunol. 1984. 133:3001-3005.

Kristiansen, Molecular mechanisms of ligand binding, signalling, and regulation within the superfamily of G-protein-coupled receptors: molecular modelling and mutagenesis approaches to receptor structure and function. Pharmacology and therapeutics. 2004. 103:21-80.

Kroeze et al., PRESTO-TANGO: an open-source resource for interrogation of the druggable human GPCR-ome. Nat Struct Mol Biol. May 2015;22(5):362-369. Author manuscript.

Kroon-batenburg et al., Experiences with making diffraction image data available: what metadata do we need to archive? Acta Crystal-

(56) References Cited

OTHER PUBLICATIONS logr D Biol Crystallogr. Oct. 2014;70(Pt 10):2502-9. doi: 10.1107/S1399004713029817. Epub Sep. 30, 2014.
Kuhlbrandt. Three-dimensional crystallization of membrane proteins. Q. Rev. Biophys. 1988. 21:429-477.
Kuhlbrandt. Two-dimensional crystallization of membrane proteins. Q. Rev. Biophys. 1992. 25(1):1-49.
Kukkonen et al., Muscarinic Toxin 7 Selectivity is Dictated by Extracellular Receptor Loops. J. Biol. Chem. 2004. 279:50923-50929.
Kuntz et al., A Geometric Approach to Macromolecule-Ligand Interactions. J. Mol. Biol. 1982. 161:269-288.
Kuroda et al., Systems for the detection and analysis of protein-protein interactions. Appl. Microbiol. Biotechnol. 2006. 71(2):127-136.
Kyte et al., A Simple Method for Displaying the Hydropathic Character of a Protein. J. Mol. Biol. 1982. 157:105-132.
Labbé-Jullié et al., 1998, Mutagenesis and Modeling of the Neurotensin Receptor NTR1, Journal of Biological Chemistry, 273(26):16351-16357.
Lamb et al., Modulation of the ligand binding properties of the transcription repressor NmrA by GATA-containing DNA and site-directed mutagenesis. Prot. Sci. 2004. 13(12):3127-3138.
Landau et al., Lipidic cubic phases: A novel concept for the crystallization of membrane proteins. PNAS USA. 1996. 93:14532-14535.
Lane et al., Protean agonism at the dopamine D2 receptor: (S)-3-(3-hydroxyphenyl)-N-propylpiperidine is an agonist for activation of Go1 but an antigonist/inverse agonist for Gi1, Gi2, and Gi3. Mil Pharmacol. 2007 71(5):1349-1359. Epub Feb. 7, 2007.
Lang et al., Structure-activity relationship studies: Methods and ligand design for g-protein coupled peptide receptors. Curr. Prot. Peptide Sci. 2006. 7:335-353.
Latronico et al., Gonadotropin-Independent Precocious Puberty Due to Luteinizing Hormone Receptor Mutations in Brazilian Boys: A Novel Constitutively Activating Mutation in the First Transmembrane Helix. J. Clin. Endocrinol. Metabl. 2000. 85(12):4799-4805.
Lattion et al., Constitutively active mutants of the β1-adrenergic receptor. FEBS Letters 1999 457(3):302-306.
Lattman. Use of Rotation and Translation Functions. Meth. Enzymol. 1985. 115:55-77.
Lau et al., Changing single side chains can greatly enhance the resistance of a membrane protein to irreversible inactivation. J. Mol. Biol. 1999. 290:559-564.
Lauri et al., CAVEAT: A Program to Facilitate the Design of Organic Molecules. J. Comp. Aided Mol. Design. 1994. 8:51-66.
Lee et al., Alanine scanning mutagenesis of conserved arginine/lysine-arginine/lysine-x-x-arginie/lysine G protein/activating motifs on M1 muscarinic acetylcholine receptors. Molecular Pharmacology. 1996 50(1):140-148.
Lee et al., Cell imaging assays for G protein-coupled receptor internalization: application to high-throughput screening. Methods Enzymol. 2006;414:79-98.
Lee et al., D2 Dopamine receptor homodimerization is mediated by multiple sites of interaction, including an intermolecular interaction involving transmembrane domain 4. Biochemistry. 2003. 42(37):11023-11031.
Lee et al., State of the art in studying protein folding and protein structure predictio using molecular dynamics methods. J. Mol. Graph & Modelling. 2001. 19(1):146-149.
Lefèvre et al., Alanine-stretch scanning mutagenesis: a simple and efficient method to probe protein structure and function. Nucl. Acids Res. 1997. 25(2):447-448.
Lehmann et al., The consensus concept for thermostability engineering of proteins. Biochim Biophys Acta. Dec. 29, 2000;1543(2):408-415.
Lehmann et al., The consensus concept for thermostability engineering of proteins: further proof of concept. Protein Engineering. 2002. 15(5):403-411.

Leifert et al., G-Protein-Coupled Receptors in Drug Discovery: Nanosizing Using Cell-Free Technologies and Molecular Biology Approaches. J. Biomol. Screening. 2005. 10:765-779.
Leroy et al., G Protein-coupled receptor-mediated ERK1/2 phosphorylation: towards a generic sensor of GPCR activation. J. Recept. Signal. Transduct. Res. 2007. 27(1):83-97.
Lewis et al., Adverse reactions with beta-adrenoceptor blocking drugs: an update. Drug Safety. 1993. 9:272-279.
Li et al., Distinct Structural Changes in a G Protein-coupled Receptor Caused by Different Classes of Agonist Ligands. J. Biol. Chem. 2007. 282(36):26284-26293.
Li et al., Random Mutagenesis of the M3 Muscarinic Acetylcholine Receptor Expressed in Yeast. J. Biol. Chem. 2005. 280:5664-5675.
Li et al., Structure of Bovine Rhodopsin in a Trigonal Crystal Form. J. Mol. Biol. 2004. 343:1409-1438.
Liu (ed), Cell Information and Regulation. China Union Medical University Press, Nov. 2003, pp. 188-189.
Liu et al., Analysis of the coupling of G12/13 to G protein-coupled receptors using a luciferase reporter assay. Methods Mol. Biol. 2004. 237:145-149.
Liu et al., Structural Basis for Allosteric Regulation of GPCRs by Sodium Ions. Science. Jul. 2012;337(6091):232-6.
Lohse et al. Kinetic analysis of G protein-coupled receptor signaling using fluorescence resonance energy transfer in living cells. Adv Protein Chem 2007 74:167-188.
Lu et al., Transmembrane domains 4 and 7 of the M(1) muscarinic acetylcholine receptor are critical for ligand binding and the receptor activation switch. J Biol Chem. Sep. 7, 2001;276(36):34098-104. Epub Jul. 5, 2001.
Luecke et al., Structure of bacteriorhodopsin at 1.55 A resolution. J. Mol. Biol. 1999. 291(4):899-911.
Mackrill, Generation, Use, and Validation of Receptor-Selective Antibodies. Methods in Molecular Biology. 2004;259:47-65.
Maclean et al., Encoded combinatorial chemistry: Synthesis and screening of a library of highly functionalized pyrrolidines. PNAS. 1997. 94:2805-2810.
Madabushi et al., Evolutionary Trace of G Protein-coupled Receptors Reveals Clusters of Residues That Determine Global and Class-specific Functions; J Biol Chem 2004 279(9):8126-8132.
Magnani et al., Co-evolving stability and conformational homogeneity of the human adenosine A2a receptor. PNAS. 2008. 105(31):10744-10749.
Makino et al., Automated flexible ligand docking method and its application for database search. J Comput. Chem. 1997. 18:1812-1825.
Marshall. Heterodimerization of G-protein-coupled receptors in the CNS. Curr. Opin. Pharmacol. 2001. 1(1):40-44.
Martin et al., A simple vector system to improve performance and utilisation of recombinant antibodies. BMC Biotechnology. 2006. 6:46.
Martin et al., Apolipoprotein A-I Assumes a "Looped Belt" Conformation on Reconstituted High Density Lipoprotein. J. Biol. Chem. 2006. 281(29):20418-20426.
Martin. 3D Database searching in drug design. J. Med. Chem. 1992. 35:2145-2154.
Martin-Garcia et al., Interaction with CD4 and Antibodies to CD4-Induced Epitopes of the Envelope gp120 from a Microglial Cell-Adapted Human Immunodeficiency Virus Type 1 Isolate. J. Virology. 2005. 79:6703-6713.
Mathew et al., Functional fusions of T4 lysozyme in the third intracellular loop of a G protein-coupled receptor identified by a random screening approach in yeast. Protein Eng Des and Sel. Oct. 2012;26(1):59-71.
Mathews et al., Comparison of Protein Structures. Methods of Enzymology. 1985. 115:397-420.
Matsui et al., Specific removal of β1-adrenoceptor autoantibodies by immunoabsorption in rabbits with autoimmune cardiomyopathy improved cardiac structure and function. J. Mol. Cell Cardiol. 2006. 41(1):78-85. epub Jun. 14, 2006.
McCafferty et al., Phage antibodies: filamentous phage displaying antibody variable domains. Nature. 1990. 348:552-554.
McCoy. Phaser crystallographic software. Acta Crystallogr. 2007. 40:658-674.

(56) References Cited

OTHER PUBLICATIONS

McCoy. Solving Structures of protein complexes by molecular replacement with Phaser. Acta Crystallogr. 2007. D63:32-41.
McLachlan. Gene duplications in the structural evolution of chymotrypsin. J. Mol. Biol. 1979. 128, 49-79.
Mehler et al., Ab initio computational modelling of loops in G-protein-coupled receptors: Lessons from the crystal structure of rhodopsin. Proteins Structures Function and Bioinformatics. 2006. 64(3):673-690.
Meng et al., Automated docking with grid-based energy evaluation. J. Comp. Chem. 1992. 13:505-524.
Mezzasalma et al., Enhancing recombinant protein quality and yield by protein stability profiling. J. Biolmol. Screening. 2007. 12(3):418-428.
Michaelson et al., Antibodies to muscarinic acetylcholine receptors in myasthenia gravis. Biochem. Biophys. Res. Commun. 1982. 104(1):52-57.
Miller et al., Engineering an ultra-thermostable β1-adrenoceptor. J Mol Biol. Oct. 28, 2011;413(3):628-638. Author manuscript (17 pages).
Milligan et al., Chimeric Gα proteins: their potential use in drug discovery. Trends Pharmacol Sci. Mar. 1999;20(3):118-124.
Milligan et al., Protein-protein interactions at G-protein-coupled receptors. Trends Pharmacol. Sci. 2001. 22:513-518.
Milligan. G protein-coupled receptor dimerisation: Molecular basis and relevance to function. Biochim. Biophys Acta. 2007. 1768(4):825-835.
Milstein et al., Hybrid hybridomas and their use in immunohistochemistry. Nature. 1983. 305:537-540.
Minic et al., Immobilization of native membrane-bound rhodopsin on biosensor surfaces. Biochim. Biophys. Acta-General Subjects. 2005. 1924:324-332.
Minneman et al., A Comparison of the Beta-Adrenergic Receptor of the Turkey Erythrocyte with Mammalian Beta1 and Beta2 Receptors. Mol. Pharmacol. 1980. 17:1-7.
Miranker et al., Functionality Maps of Binding Sites: A Multiple Copy Simultaneous Search Method Proteins: Structure, Function and Genetics. 1991. 11:29-34.
Mishina et al., Multiplex GPCR Assay in Reverse Transfection Cell Microarrays. J Biomol Screen. Apr. 2004;9(3):196-207.
Misquitta et al. Membrane Protein Crystallization in Lipidic Mesophases with Tailored Bilayers. Structure. 2004. 12:2113-2124.
Moran et al., Radio frequency tag encoded combinatorial library method for the discovery of tripeptide-substituted cinnamic acid inhibitors of the protein tyrosine phosphatase PTB1B. JACS. 1995. 117:10787-10788.
Morris et al., Automated docking using a Lamarckian genetic algorithm and an empirical binding free energy function. J. Comput. Chem. 1998. 19:1639-1662.
Morrison. Success in specification. Nature. 1994. 368:812-813.
Mozsolits et al., Surface plasmon resonance spectroscopy in the study of membrane-mediated cell signalling. J. Peptide Sci. 2003. 9:77-89.
Munson et al., Ligand: a versatile computerized approach for characterization of ligand-binding systems. Anal. Biochem. 1980. 107:220-239.
Murakami et al., Crystal structure of squid rhodopsin. Nature. May 15, 2008;453(7193):363-7.
Myburgh et al., A single amino acid substitution in transmembrane helix VI results in overexpression of the human GnRH receptor. Eur. J. Endocrinol. 1998. 139(4):438-447.
Navarro et al., Receptor-Dependent G-Protein activation in Lipidic Cubic phase. Biopolymers. 2002. 67:167-177.
Navaza. AMoRe: an Automated Package for Molecular Replacement. Acta Cryst. 1994. D50:157-163.
Navia et al., Use of structural information in drug design. Curr Opin Struc Biol. 1992. 2:202-210.
Navratilova et al., Analyzing ligand and small molecule binding activity of solubilized GPCRs using biosensor technology. Anal. Biochem. 2006. 355:132-139.
Nawaratne et al., New insights into the function of M4 muscarinic acetylcholine receptors gained using a novel allosteric modulator and a DREADD (designer receptor exclusively activated by a designer drug). Mol Pharmacol. Oct. 2008;74(4):1119-31. Epub Jul. 15, 2008.
Needleman et al., A general method applicable to the search for similarities in the amino acid sequence of two proteins. J Mol Biol Mar. 1970; 48(3):443-453.
Neubig et al., International Union of Pharmacology Committee on Receptor Nomenclature and Drug Classification. XXXVIII. Update on Terms and Symbols in Quantitative Pharmacology. Pharmacol. Rev. 2003. 55:597-606.
New et al., Chimeric and Promiscuous G Proteins in Drug Discovery and the Deorphanization of GPCRs. Drug Design Reviews—Online. 2005;2:66-79.
Newman-Tancredi et al., Agonist and inverse agonist efficacy at human recombinant serotonin 5-HT1A receptors as a function of receptor:G-protein stoichiometry. Neurophamacology. 1997. 36:451-459.
Ngo et al., Identifying ligands at orphan GPCRs: current status using structure-based approaches. Br J Pharmacol. Oct. 2016;173(20):2934-51. doi: 10.1111/bph.13452. Epub Mar. 5, 2016.
Nicolaou et al., Radiofrequency encoded combinatorial chemistry. Angew. Chem. Int. Ed. Engl. 1995. 34:2289-2291.
Nishihata et al., Automatic creation of drug candidate structures based on receptor structure. Starting point for artificial lead generation. Tetrahedron. 1991. 47:8985-8990.
Nunomura et al., Regulation of Protein 4.1R, p55, and Glycophorin C Ternary Complex in Human Erythrocyte Membrane. J. Biol. Chem. 2000. 275:24540-24546.
Ohlmeyer et al., Complex synthetic chemical libraries indexed with molecular tags. PNAS. 1993. 90:10922-10926.
Oldham et al., Mapping allosteric connections from the receptor to the nucleotide-binding pocket of heterotrimeric G proteins. PNAS. 2007. 104(19):7927-7932.
Omerovic et al., Induction of Cardiomyopathy in Immunodeficiency Mice by Transfer Patients with Idiopathic Dilated Cardiomyopathy. Autoimmunity. 2000. 32(4):271-280.
Osbourn et al., Directed selection of MIP-1 alpha neutralizing CCR5 antibodies from a phage display human antibody library. Nature Biotechnology. 1998. 16:778-781.
Ostermeier et al., Crystalization of Membrane Proteins. Curr. Opin. Struct. Biol. 1997. 7:697-701.
Ott et al., Engineering and functional immobilization of opioid receptors. Prot. Eng. Design & Selection. 2005. 18:153-160.
Overington et al., How many drug targets are there? Natur Rev. Drug Discovery. 2006. 5:993-996.
Palczewski et al., Crystal Structure of Rhodopsin: A G Protein-Coupled Receptor. Science. 2000. 289:739-745.
Palmer et al., Treatment of systemic lupus erythematosus by extracorporeal immunoadsorption. Lancet. 1988. 2(8605):272.
Pardo et al., The role of internal water molecules in the structure and function of the rhodopsin family of G protein-coupled receptors. Chembiochem. Jan. 2, 2007;8(1):19-24.
Park et al., Characterization of radioligand binding to a transmembrane receptor reconstituted into Lipobeads. FEBS Lett. 2004. 567:344-348.
Parker et al., Carboxyl terminal domains in the avian β1-adrenergic receptor that regulate agonist-promoted endocytosis. J. Biol. Chem. 1995. 270:6482-6487. Erratum in: J Biol Chem 1995. 270(17):10358.
Parker et al., Reconstitutively Active G Protein-coupled Receptors Purified from Baculovirus-infected Insect Cells. J. Biol. Chem. 1991. 266:519-527.
Parker et al., Truncation of the Extended Carboxyl-terminal Domain Increases the Expression and Regulatory Activity of the Avian, & Adrenergic Receptor. J. Biol. Chem. 1991. 266:9987-9996.
Parsons et al., Directing phage selections towards specific epitopes. Protein Engineering. 1996. 9:1043-1049.
Perez. From Plants to Man: The GPCR "Tree of Life". Mol. Pharmacol. 2005. 67:1383-1384.
Pin et al., Evolution, structure, and activation mechanism of family 3/C G-protein-coupled receptor, Pharm. & Ther. 2003 98 325-354.

(56) References Cited

OTHER PUBLICATIONS

Plant et al., Phospholipid/alkanethiol bilayers for cell-surface receptor studies by surface plasmon resonance. Analyt. Biochem. 1995. 226(2):342-348.
Pogozheva et al., Interactions of human melanocortin 4 receptor with nonpeptide and peptide agonists. Biochemistry. Aug. 30, 2005;44(34): 11329-41.
Ponsioen et al. Detecting cAMP-induced Epac activation by fluorescence resonance energy transfer: epac as a novel cAMP indicator, 2004 EMBO Rep.;5(12):1176-1180.
Privé, Detergents for the stabilization and crystallization of membrane proteins. Methods. Apr. 2007;41(4):388-97.
Qian et al., High-resolution structure prediction and the crystallographic phase problem. Nature. 2007. 450:259-264.
Quick et al., Monitoring the function of membrane transport proteins in detergent-solubilized form. PNAS. 2007. 104(9):3603-3608.
Rarey et al., A fast flexible docking method using an incremental construction algorithm. J. Mol. Biol. 1996. 261:470-489.
Rasmussen et al., Crystal structure of the human β2 adrenergic g-protein-coupled receptor. Nature. 2007. 450:383-387.
Rasmussen et al., Mutation of a Highly Conserved Aspartic Acid in the β2 Adrenergic Receptor: Constitutive Activation, Structural Instability, and Conformational Rearrangement of Transmembrane Segment 6. Molecular Pharmacol. 1999. 56:175-84.
Riekel et al., Protein crystallography microdiffraction. Curr. Opin. Struct. Biol. 2005. 15(5):556-562.
Rigaut et al., A generic protein purification method for protein complex characterization and proteome exploration. Nature Biotechnol. 1999. 17(10): 1030-1032.
Robas et al., Maximizing serendipity: strategies for identifying ligands for orphan G-protein-coupled receptors. Curr Opin Pharmacol. Apr. 2003;3(2):121-6.
Roberts et al., Mechanisms of inverse agonist action at D2 dopamine receptors. Br. J. Pharmacol. 2005. 145:34-42.
Robertson et al., The properties of thermostabilized G protein-coupled receptors (StaRs) and their use in drug discovery. Neuropharmacology 60: 36-44, 2011.
Robinson-Rechavi et al., Contribution of Electrostatic Interactions, Compactness and Quaternary Structure to Protein Thermostability: Lessons from Structural Genomics of Thermotoga maritima. J. Mol. Biol. 2006. 356:547-557.
Rodgers et al., Development of displacement binding and GTPγS scintillation proximity assays for the identification of antagonists of the μ-opiod receptor. Assay Drug Dev. Technol. 2003. 1(5):627-636.
Rosenbaum et al., GPCR Engineering Yields High-Resolution Structural Insights into b2-Adrenergic Receptor Function. Science. 2007. 318:1266-1273.
Rossmann et al., A Comparison of the Heme Binding Pocket in Globins and Cytochrome b. J. Biol. Chem. 1975. 250:7525-7532.
Roth et al., Stabilization of the β2-adrenergic Receptor 4-3-5 Helix Interface by Mutagenesis of Glu-1223.41, A Critical Residue in GPCR Structure. J. Mol. Biol. 2008. 376:1305-1319.
Rovati et al., The Highly Conserved DRY Motif of Class A G Protein-Coupled Receptors: Beyond the Ground State. Mol. Pharmacol. 2007. 71(4):959-964.
Rummel et al., Lipidic Cubic Phases: New Matrices for the Three-Dimensional Crystallization of Membrane Proteins. J. Struct. Biol. 1998. 121:82-91.
Sali et al., Comparative protein modelling of satisfaction by spatial restraints. J. Mol. Biol. 1993. 234(3):779-815.
Samama et al., A mutation-induced activated state of the β2-adrenergic receptor. J Biol Chem. 1993 268(7):4625-4636.
Sarkar et al., Directed evolution of a G protein-coupled receptor for expression, stability, and binding selectivity. PNAS. 2008. 105(39):14808-14813.
Savinainen et al., Identification of WIN55212-3 as a competitive neutral antagonist of the human cannabinoid CB2 receptor. Br. J. Pharmacol. 2005. 145:636-645.
Sayle et al., RASMOL: biomolecular graphics for all. Trends in Biochemical Sciences. 1995. 20:374-376.
Scarselli et al., Multiple Residues in the Second Extracellular Loop are Critical forM3 Muscarinic Acetylcholine Receptor Activation. J. Biol. Chem. 2007. 282:7385-7396.
Schaffner et al., A Rapid, Sensitive, and Specific Method for the Determination of Protein in Dilute Solution. Anal. Biochem. 1973. 56:502-514.
Schena et al., Quantitative monitoring of gene expression patterns with a complementary DNA microarray. Science. 1995. 270:467-470.
Schimerlik, Overview of membrane protein solubilization. Current Protocols in Neuroscience 2001;5.9.1-5.9.5. Abstract.
Schnare et al. Comprehensive comparison of structural characteristics in eukaryotic cytoplasmic large subunit (23S-like) ribosomal RNA. J. Mol. Biol. 1996. 256:701-719.
Schofield et al., Application of phage display to high throughput antibody generation and characterization. Genome Biology. 2007. 8(11):R254.
Schultz et al., Requirement of Specific Intrahelical Interactions for Stabilizing the Inactive Conformation of Glycoprotein Hormone Receptors. J. Biol. Chem. 2000. 275(48):37860-37869.
Scopes, 4.7 Precipitation by Selective Denaturation. General Principles. Purification: Principles and Practice. $3^{rd}$ Edition. 1994:95.
Screpanti et al., Crucial Steps in the Structure Determination of the Na+/H+ Antiporter NhaA in its Native Conformation. J. Mol. Biol. 2006. 362:192-202.
Sebestyen et al., Efficiency and limitations of the 'portioning-mixing' peptide synthesis. Pept. Proc. Eur. Pept. Symp. 22nd 1992. 1993. 63-64.
Sen et al., Functional studies with membrane-bound and detergent-solubilized alpha2-adrenergic receptors expressed in Sf9 cells. Biochim Biophys Acta. 2005 1712(1):62-70. Epub Apr. 26, 2005.
Shi et al., Beta2 adrenergic receptor activation. Modulation of the proline kink in transmembrane 6 by a rotamer toggle switch. J Biol Chem. Oct. 25, 2002;277(43):40989-96. Epub Aug. 6, 2002.
Shi et al., The second extracellular loop of the dopamine D2 receptor lines the binding-site crevice. PNAS 2004. 101:440-445.
Shibata et al. Thermostabilization of the Neurotensin Receptor NTS1, J. Mol. Biol. 2009 390(2):262-277.
Shiroishi, [Strategies for the structural determination of G protein-coupled receptors: from an example of histamine $H_1$ receptor]. Yakugaku Zasshi. 2013;133(5):539-47.
Shoichet et al., Structure-based drug screening for G-protein-coupled receptors. Trends in Pharma Science 33(5): 268-272, 2012.
Skerra. 'Anticalins': a new class of engineered ligand-binding proteins with antibody-like properties. J. Biotechnol. 2001. 74(4):257-275.
Sobek et al., Microarray technology as a universal tool for high-throughput analysis of biological systems. Combinat. Chem. & High Throughput Screening. 2006. 9:365-380.
Spalding et al., Structural Requirements of Transmembrane Domain 3 for Activation by the M1 Muscarinic Receptor Agonists AC-42, AC-260584, Clozapine, and N-Desmethylclozapine: Evidence for Three Distinct Modes of Receptor Activation. Mol. Pharmacol. 2006. 70:1974-1983.
Standfuss et al., Crystal Structure of a thermally stable rhodopsin mutant. J Mol Biol. 2007 372(5):1179-1188.
Steipe et al., Sequence statistics reliably predict stabilizing mutations in a protein domain. J. Mol. Biol. 1994. 240:188-192.
Stenlund et al., Capture and reconstitution of G protein-coupled receptors on a biosensor surface. Analytical Biochemistry. 2003. 316:243-250.
Stock et al., Robotic nanolitre protein crystallisation at the MRC Laboratory of Molecular Biology. Prog. Biophys. Mil. Biol. 2005. 88:311-327.
Sugimoto et al., Beta(1)-selective agonist (−)-1-(3,4-dimethoxyphenetylamino)-3-(3,4-dihydroxy)-2-propanol [(−)-RO363] differentially interacts with key amino acids responsible for beta(1)-selective binding in resting and active states. J Pharmacol Exp Ther. Apr. 2002;301(1):51-8.

(56) References Cited

OTHER PUBLICATIONS

Sung et al., Rhodopsin Mutations Responsible for Autosomal Dominant Retinitis Pigmentosa. J. Biol. Chem. 1993. 268(35):26645-26649.
Sutcliffe et al., Knowledge based modelling of homologous proteins, part I: three-dimensional frameworks derived from the simultaneous superposition of multiple structures. Protein Eng. 1987. 1:377-384.
Suwa, GPCR Proteome surveyed from genomic information analysis. Pharmacia. 2014;50(9):888-92.
Swaminath et al., Sequential Binding of Agonists to the 2 Adrenoceptor. J. Biol. Chem. 2004. 279(1):686-691.
Szklarz & Halpert. Use of homology modeling in conjunction with site-directed mutagenesis for analysis of structure-function relationships of mammalian cytochromes P450. Life Sci. 1997. 61:2507-2520.
Tan et al., FGF and stress regulate CREB and ATF-1 via a pathway involving p38 MAP kinase and MAPKAP kinase-2. EMBO J. 1996. 15(17):4629-4642.
Tao et al., Chimeras of the Rat and Human FSH Receptors (FSHRs) Identify Residues that Permit or Suppress Transmembrane 6 Mutation-Induced Constitutive Activation of the FSHR via Rearrangements of Hydrophobic Interactions Between Helices 6 and 7. Mol. Endocrinol. 2002. 16(8):1881-1892.
Tate, Baculovirus-Mediated Expression of Neurotransmitter Transporters. Methods Enzymol. 1998. 296:443-455.
Tate. Overexpression of mammalian integral membrane proteins for structural studies. FEBS Lett. 2001. 504:94-98.
Teng et al., Control of feeding behavior in C. elegans by human G protein-coupled receptors permits screening for agonist-expressing bacteria. PNAS. 2008. 105(39):14826-14831.
Teng et al., Expression of mammalian GPCRs in C. elegans generates novel behavioural responses to human ligands. BMC Biology. 2006. 4:22.
Themmen & Huhtaniemi. Mutations of Gonadotropins and Gonadotropin Receptors: Elucidating the Physiology and Pathophysiology of Pituitary-Gonadal Function. Endocr. Rev. 2000. 21(5):551-583.
Thompson et al., CLUSTAL W: improving the sensitivity of progressive multiple sequence alignment through sequence weighting, position-specific gap penalties and weight matrix choice Nucl. Acids Res. 1994. 22:4673-4680.
Topiol & Sabio. Use of the X-ray structure of the β2-adrenergic receptor for drug discovery. Bioorganic & Medicinal Chemistry. 2008. 18(5):1598-1602.
Traunecker et al., Bispecific single chain molecules (Janusins) target cytotoxic lymphocytes on HIV infected cells. EMBO J. 1991. 10:3655-3659.
Tucker & Grisshammer. Purification of a rat neurotensin receptor expressed in *Escherichia coli*. Biochem. J. 1996. 317(Pt. 3):891-899.
Urizar et al. An activation switch in the rhodopsin family of G protein-coupled receptors: The Thyrotropin receptor J. Biol Chem 2005 280( 17):17135-17141.
Vagin & Teplyakov. MOLREP: an automated program for molecular replacement. J. Appl. Cryst. 1997. 30:1022-1025.
Vakser. Evaluation of GRAMM low-resolution docking methodology on hemagglutinin-antibody complex. Proteins, Suppl. 1997. 1:226-230.
Venturi & Hunte. Monoclonal antibodies for the structural analysis of the Na+/H+ antiporter NhaA from *Escherichia coli*. Biochimica et aBiophysica Acta. 2003. 1610:46-50.
Voet et al., Protein Stability. Chapter 7: Three-Dimensional Structures of Proteins. Biochemistry $2^{nd}$ Edition. 1995. 179-180.
Vohra et al., Similarity between class A and class B G-protein-coupled receptors exemplified through calcitonin gene-related peptide receptor modelling and mutagenesis studies J R Soc Interface. Dec. 12, 2012;10(79):20120846. doi: 10.1098/rsif.2012.0846. Print Feb. 2013.
Walters et al., Virtual screening—an overview. Drug Discovery Today. 1998. 3(4): 160-178.

Wang (ed), Protein Engineering. Beijing Chemical Industry Press, May 2002, pp. 58-59.
Wang et al., Establishment of a chimeric reporting system for the universal detection and high-throughput screening of a G protein-coupled receptors. Biosens Bioelectron. Mar. 15, 2009;24(7):2298-304. doi: 10.1016/j.bios.2008.11.023. Epub Dec. 7, 2008.
Wang. Basic Amino Acids at the C-Terminus of the Third Intracellular Loop are Required for the Activation of Phospholipase C by Cholecystokinin-B Receptors. J. Neurochem. 1997. 68(4):1728-1735.
Warne et al., Structure of a β1-adrenergic G protein-coupled receptor. Nature. 2008. 454:486-491.
Warne et al., Expression and purification of truncated, non-glycosylated turkey beta-adrenergic receptors for crystallization. Biochim. Biophys. Acta. 2003. 1610:133-140.
Warne et al., The purification of G-protein coupled receptors for crystallization, Structural Biology of Membrane Proteins, Royal Society of Chemistry. 2006. 51-71.
Weber et al., A 1,536-Well cAMP Assay for Gs- and Gi-Coupled Receptors Using Enzyme Fragmentation Complementation. Assay Drug Dev. Technol. 2004. 2(1):39-49.
Weiss et al., Purification and characterization of the human adenosine A2a receptor functionally expressed in *Escherichia coli*. Eur. J. Biochem. 2002. 269:82-92.
Wess. Molecular Basis of Receptor/G-Protein-Coupling Selectivity. Pharmacol. Ther. 1998. 80:231-264.
White. The progress of membrane protein structure determination. Protein Science. 2004. 13:1948-1949.
Wiencek, New strategies for protein crystal growth. Annu Rev Biomed Eng. 1999;1:505-34.
Williams & Addona. The integration of SPR biosensors with mass spectrometry: possible applications for proteome analysis. Trends Biotechnol. 2000. 18(2):45-48.
Williams. Biotechnology match making: screening orphan ligands and receptors. Curr. Opin. Biotechnol. 2000. 11(1):42-46.
Winter & Milstein. Man-made antibodies. Nature. 1991. 349:293-299.
Winter et al., Surface binding affinity measurements from order transitions of lipid-membrane-coated colloidal particles. Anal. Chem. 2006. 78:174-180.
Wise et al., The Identification of Ligands at Orphan G-Protein Coupled Receptors. Annu Rev Pharmacol Toxicol. 2004;44:43-66.
Wurch et al., Chimeric Receptor Analysis of the Ketanserin Binding Site in the Human 5-Hydroxytryptamine1D Receptor: Importance of the Second Extracellular Loop and Fifth Transmembrane Domain in Antagonist Binding. Mol. Pharmacol. 1998. 54(6):1088-1096.
Wyckoff. Diffractometry. Methods in Enzymology. 1985. 114:330-386.
Xie et al., An opsin mutant with increased thermal stability. Biochemistry. Feb. 25, 2003 ;42(7):1995-2001.
Yano et al., Phe576 Plays an Important Role in the Secondary Structure and Intracellular Signaling of the Human Luteinizing Hormone/Chorionic Gonadotropin Receptor. J. Clin. Endocrinol. Metabl. 1997. 82(8):2586-2591.
Yao et al., Coupling ligand structure to specific conformational switches in the Pβ2-adrenoceptor. Nat. Chem. Biol. 2006. 2(8):417-422.
Yarden et al., The avian beta-adrenergic receptor: Primary structure and membrane topology. Proc. Natl. Acad. Sci. USA. 1986. 83:6795-6799.
Yohannan et al., The evolution of transmembrane helix kinks and the structural diversity of G protein-coupled receptors. PNAS. 2004. 101(4):959-963.
Yokogawa et al., Bead-linked Proteoliposomes: A Reconstitution Method for NMR Analyses of Membrane Protein-Ligand Interactions. J. Am. Chem. So. 2005. 127:12021-12027.
Yu et al., Introduction to Molecular Design. Beijing Higher Education Press; Germany Springer Press; Jul. 2000, pp. 130-135.
Zeitoun, O. et al., 2006, Mutagenesis within Helix 6 of the Human β1-Adrenergic Receptor Identifies Lysine324 as a Residue Involved in Imparting the High-Affinity Binding State of Agonists, Molecular Pharmacology, 70(3):838-850.

(56) References Cited

OTHER PUBLICATIONS

Zhai et al., Introduction to Modern Biotechnology. Beijing Higher Education Press; Germany Springer Press; Aug. 1998, pp. 123 (paragraph 3), 127 (last paragraph), 136-140.
Zhang et al., Adopting selected hydrogen bonding and ionic interactions from Aspergillus fumigatus phytase structure improves the thermostability of Aspergillus niger PhyA phytase. Appl Environ Microbiol. May 2007;73(9):3069-76. Epub Mar. 9, 2007.
Zhang et al., Agonist-bound structure of the human $P2Y_{12}$ receptor. Nature. May 2014;509(7498):119-22. Author Manuscript. 26 pages.
Zhang et al., Selection of Active ScFv to G-Protein-Coupled Receptor CCR5 Using Surface Antigen-Mimicking Peptides. Biochemistry. Oct. 5, 2004;43(39):12575-84.
Zhang et al., Structure modelling of all identified G-protein coupled receptors in the human genome. PloS Computational Biology. 2006. 2(2):88-99.
Zhao et al. A homogeneous enzyme fragment complementation-based {beta}-Arrestin translocation assay for high-throughput screening of G-Protein-Coupled receptors: J. Biomol Screen 2008;13(8):737-747; Epub 2008.
Zheng et al., An efficient one-step site-directed and site-saturation mutagenesis protocol. Nucl. Acids Res. 2004. 32:e115.
Zhou et al., Building a Thermostable Membrane Protein. J. Biol. Chem. 2000. 275:6975-6979.
Zurawski et al., A novel biosensor assay for screening peptide antagonism of the interaction between HIV-1 envelope, CD4 and membrane-embedded CCR5. Biopolymers. 2003. 71:388-389. Abstract P395.
Lebon et al., Thermostabilisation of an agonist-bound conformation of the human adenosine A2A receptor. J Mol Biol. Jun. 10, 2011;409(3):298-310. doi: 10.1016/j.jmb.2011.03.075. Epub Apr. 9, 2011.
EP 12192130.8, Feb. 27, 2013, Extended European Search Report.
PCT/GB2011/001177, Mar. 30, 2012, International Search Report and Written Opinion.
PCT/GB2011/001177, Mar. 7, 2013, International Preliminary Report on Patentability.
PCT/GB2013/051464, Jan. 14, 2014, International Search Report and Written Opinion.
PCT/GB2013/051464, Dec. 11, 2014, International Preliminary Report on Patentability.
PCT/GB2008/000740, Jul. 28, 2008, International Search Report and Written Opinion.
PCT/GB2008/000740, Sep. 7, 2010, International Preliminary Report on Patentability.
PCT/GB2008/000986, Jan. 19, 2009, International Search Report and Written Opinion.
PCT/GB2008/000986, Jul. 6, 2009, International Preliminary Report on Patentability.
PCT/GB2008/004032, Aug. 19, 2009, International Search Report and Written Opinion.
PCT/GB2008/004032, Jun. 8, 2010, International Preliminary Report on Patentability.
PCT/GB2008/004223, Aug. 19, 2009, International Search Report and Written Opinion.
PCT/GB2008/004223, Jun. 22, 2010, International Preliminary Report on Patentability.
PCT/GB2009/000310, Jun. 23, 2009, International Search Report and Written Opinion.
PCT/GB2009/000310, Aug. 26, 2010, International Preliminary Report on Patentability.
PCT/GB2010/001227, Jun. 20, 2011, International Search Report and Written Opinion.
PCT/GB2010/001227, Jan. 12, 2012, International Preliminary Report on Patentability.
PCT/GB2012/051940, Feb. 1, 2013, International Search Report and Written Opinion.
PCT/GB2012/051940, Feb. 20, 2014, International Preliminary Report on Patentability.
Office Communication dated Mar. 24, 2017 for Chinese Application No. 201310556727.3.
Office Communication dated Feb. 14, 2012 for U.S. Appl. No. 12/450,358.
Office Communication dated Sep. 11, 2012 for U.S. Appl. No. 12/450,358.
Office Communication dated Apr. 12, 2013 for U.S. Appl. No. 12/450,358.
Office Communication dated Sep. 27, 2013 for U.S. Appl. No. 12/450,358.
Office Communication dated Jan. 27, 2014 for U.S. Appl. No. 12/450,358.
Office Communication dated Jan. 16, 2013 for U.S. Appl. No. 13/493,898.
Office Communication dated Jul. 12, 2013 for U.S. Appl. No. 13/493,898.
Office Communication dated Feb. 7, 2014 for U.S. Appl. No. 13/493,898.
Office Communication dated Oct. 1, 2014 for U.S. Appl. No. 13/493,898.
Office Communication dated Aug. 8, 2018 for U.S. Appl. No. 15/716,302.
Office Communication dated Jul. 27, 2012 for U.S. Appl. No. 12/746,674.
Office Communication dated Apr. 4, 2013 for U.S. Appl. No. 12/746,674.
Office Communication dated Jan. 28, 2013 for U.S. Appl. No. 12/809,181.
Office Communication dated Jul. 10, 2013 for U.S. Appl. No. 12/809,181.
Office Communication dated Feb. 11, 2015 for U.S. Appl. No. 14/255,939.
Office Communication dated Jul. 12, 2017 for U.S. Appl. No. 14/989,744.
Notice of Allowance dated Jul. 5, 2018 for U.S. Appl. No. 14/989,744.
Office Communication dated Jan. 7, 2020 for U.S. Appl. No. 16/151,991.
Office Communication dated Sep. 5, 2012 for U.S. Appl. No. 12/866,594.
Office Communication dated Feb. 25, 2013 for U.S. Appl. No. 12/866,594.
Office Communication dated Jul. 22, 2013 for U.S. Appl. No. 12/866,594.
Office Communication dated Jan. 3, 2014 for U.S. Appl. No. 12/866,594.
Office Communication dated Jul. 28, 2014 for U.S. Appl. No. 12/866,594.
Office Communication dated Aug. 1, 2012 for U.S. Appl. No. 12/921,036.
Office Communication dated Feb. 15, 2013 for U.S. Appl. No. 12/921,036.
Office Communication dated Nov. 12, 2014 for U.S. Appl. No. 13/980,497.
Office Communication dated Jul. 2, 2015 for U.S. Appl. No. 13/980,497.
Office Communication dated Dec. 31, 2015 for U.S. Appl. No. 13/980,497.
Office Communication dated Nov. 20, 2017 for U.S. Appl. No. 15/197,575.
Office Communication dated Jul. 5, 2018 for U.S. Appl. No. 15/197,575.
Office Communication dated Dec. 4, 2015 for U.S. Appl. No. 14/237,678.
Office Communication dated Jun. 24, 2016 for U.S. Appl. No. 14/237,678.
Office Communication dated Apr. 5, 2017 for U.S. Appl. No. 14/237,678.
Office Communication dated Dec. 5, 2017 for U.S. Appl. No. 14/237,678.
Notice of Allowance dated Jun. 20, 2018 for U.S. Appl. No. 14/237,678.
Office Communication dated Jul. 18, 2019 for U.S. Appl. No. 16/137,421.

(56) References Cited

OTHER PUBLICATIONS

Office Communication dated Jun. 19, 2013 for U.S. Appl. No. 13/379,872.
Office Communication dated Mar. 24, 2016 for U.S. Appl. No. 14/404,768.
Office Communication dated Nov. 17, 2016 for U.S. Appl. No. 14/404,768.
Office Communication dated Jun. 30, 2017 for U.S. Appl. No. 14/404,768.
Office Communication dated May 9, 2018 for U.S. Appl. No. 14/404,768.
Office Communication dated Aug. 7, 2019 for U.S. Appl. No. 14/404,768.
Office Communication dated Oct. 31, 2013 for U.S. Appl. No. 13/817,858.
Office Communication dated Mar. 11, 2014 for U.S. Appl. No. 13/817,858.
Office Communication dated Oct. 13, 2015 for U.S. Appl. No. 14/210,266.
Office Communication dated Mar. 9, 2016 for U.S. Appl. No. 14/210,266.

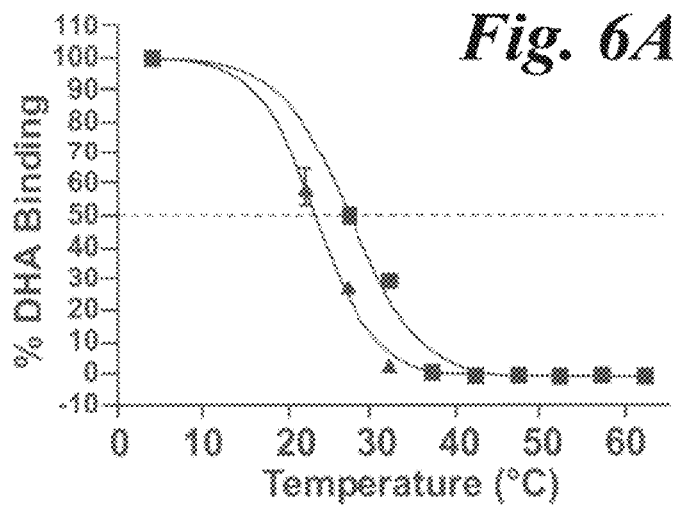
*Fig. 6A*
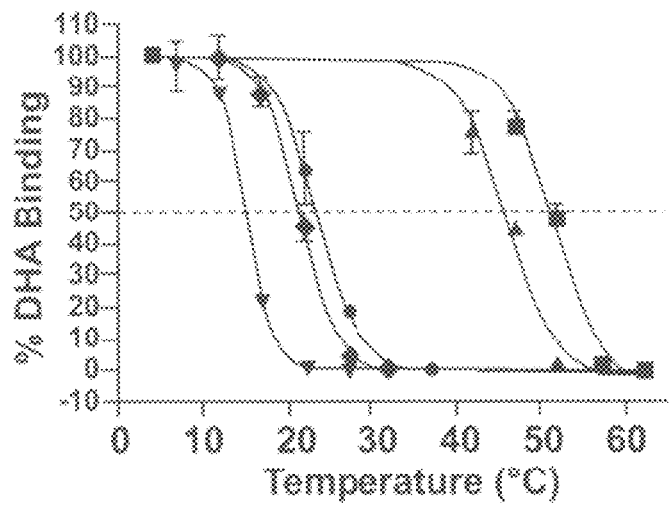
*Fig. 6B*
*Fig. 6C*
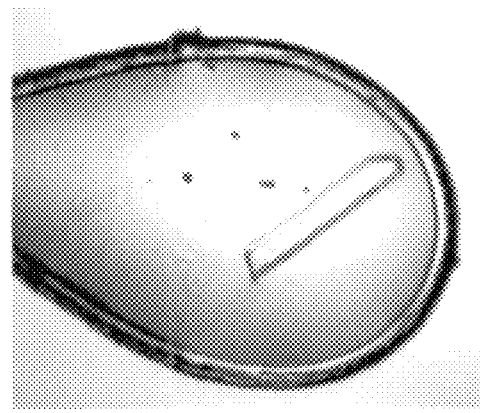

Alignment of the turkey β-adrenergic receptor with human β1, β2 and β3

```
adrb1_melga    1            MGDGWLPPDCGPHNRSGGGATAAPTGSR----------------  29
adrb1_human    1   MGAGVLVLGASE-------PGNLSSAAPLPDGAATAARLLVPASPPASLLP  44
adrb2_human    1            MGQ---------PGNGSAFLLAPNRSHAPD--------------  21
adrb3_human    1            MAPW--------PHENSSLAPWPDLPTLAP-------------N  23
                              *   * adrb1_melga   30  -QVSAEL-LSQQWEAGMSLLMALVVLLIVAGNVLVIAAIGRTQRLQTLTN  77
adrb1_human   45  PASESPEPLSQQWTAGMGLLMALIVLLIVAGNVLVIVAIAKTPRLQTLTN  94
adrb2_human   22  -HDVTQQ-RDEVWVVGMGIVMSLIVLAIVFGNVLVITAIAKFERLQTVTN  69
adrb3_human   24  TANTSGLPGVPWEAALAGALLALAVLATVGGNLLVIVAIAWTPRLQTMTN  73 adrb1_melga   78  LFITSLACADLVMGLLVVPFGATLVVRGTWLWGSFLCECWTSLDVLCVTA 127
adrb1_human   95  LFIMSLASADLVMGLLVVPFGATIVVWGRWEYGSFFCELWTSVDVLCVTA 144
adrb2_human   70  YFITSLACADLVMGLAVVPFGAAHILMKMWTFGNFWCEFWTSIDVLCVTA 119
adrb3_human   74  VFVTSLAAADLVMGLLVVPPAATLALTGHWPLGATGCELWTSVDVLCVTA 123 adrb1_melga  128  SIETLCVIAIDRYLAITSPFRYQSLMTRARAKVIICTVWAISALVSFLPI 177
adrb1_human  145  SIETLCVIALDRYLAITSPFRYQSLLTRARARGLVCTVWAISALVSFLPI 194
adrb2_human  120  SIETLCVIAVDRYFAITSPFKYQSLLTKNKARVIILMVWIVSGLTSFLPI 169
adrb3_human  124  SIETLCALAVDRYLAVTNPLRYGALVTKRCARTAVVLVWVVSAAVSFAPI 173 adrb1_melga  178  MMHWWRDEDP-QALKCYQDPGCCDFVTNRAYAIASSIISFYIPLLIMIFV 226
adrb1_human  195  LMHWWRAESD-EARRCYNDPKCCDFVTNRAYAIASSVVSFYVPLCIMAFV 243
adrb2_human  170  QMHWYRATHQ-EAINCYANETCCDFFTNQAYAIASSIVSFYVPLVIMVFV 218
adrb3_human  174  MSQWWRVGADAEAQRCHSNPRCCAFASNMPYVLLSSSVSFYLPLLVMLFV 223 adrb1_melga  227  YLRVYREAKEQIRKIDRCEGRFYGSQE-----QPQ--PPPLPQHQPILG- 268
adrb1_human  244  YLRVFREAQKQVKKIDSCERRFLGGPARPPSPSPSPVPAPAPPPGPPRPA 293
adrb2_human  219  YSRVFQEAKRQLQKIDKSEGRFHVQN-------------LSQVEQDGR- 253
adrb3_human  224  YARVFVVATRQLRLLRGELGRFPPEES-PPAPSRSLAPAPVGTCAPPE-- 270 adrb1_melga  269  ----------NGRASKRKTSRVMAMREHKALKTLGIIMGVFTLCWLPFFLV 309
adrb1_human  294  AAAATAPLANGRAGKRRPSRLVALREQKALKTLGIIMGVFTLCWLPFFLA 343
adrb2_human  254  -----------TGHGLRR--SSKFCLKEHKALKTLGIIMGTFTLCWLPFFIV 292
adrb3_human  271  ----------GVPACGRRPARLLPLREHRALCTLGLIMGTFTLCWLPFFLA 311 adrb1_melga  310  NIVNVFNR-DLVPDWLFVFFNWLGYANSAMNPIIYCRSPDFRKAFKRLLC 358
adrb1_human  344  NVVKAFHR-ELVPDRLFVFFNWLGYANSAFNPIIYCRSPDFRKAFQRLLC 392
adrb2_human  293  NIVHVIQD-NLIRKEVYILLNWIGYVNSGFNPLIYCRSPDFRIAFQELLC 341
adrb3_human  312  NVLRALGGPSLVPGPAFLALNWLGYANSAFNPLIYCRSPDFRSAFRRLLC 361
```

*Fig. 9A*

```
adrb1_melga  359 FPRKADRRLHAGGQPAPLPGGFISTLGSPEHSPGGTWSDCNGGTRGGSES 408
adrb1_human  393 CARRAARRRHATHGDRPR------------------ASGCLARPGPPPS 423
adrb2_human  342 LRRSSLKAYGNG------------YS------SNGNTGEQSG---      365
adrb3_human  362 RCGRRLP--------PEP------------------CAAARPALFPS   382 adrb1_melga  409 SLEERHSKTSRSESKMEREKNILATTRFYCTFLGNGDKAVFCTVLRIVKL 458
adrb1_human  424 PGAASDDDD----------DDVVGATPPARLLEPWAGCNGGAAADSDSSLDE 465
adrb2_human  366 -----YHVEQ------EKENK--------LLCEDLPGTEDFVGHQGTVPSDN 398
adrb3_human  383 GVPAARS---------------SPAQPRLCQRLDGASWGVS         408 adrb1_melga  459 FEDATCTCPHTRKLKMKWRFKQHQA 483
adrb1_human  466 PCRPGFASESKV             477
adrb2_human  399 IDSQGRNCSTNDSLL           413
adrb3_human  409                           408
```

SEE BELOW FOR KEY

Position of mutations in m23
Position of other thermostabilising mutations
Position of transmembrane domains
Position of helix 8

Where other amino acid substitutions gave significant thermostability, the position is labelled with a lower case letter and the mutations are listed below in order of decreasing thermostability.

a. R68S
b. V89L
c. M90V, A
d. I129V, A, C
e. S151E, Q
f. L221V, I
g. R229Q, A
h. A282L, V, Q
i. D322A, P
j. F327A, G, M, V
k. A334L, S, I
l. F338M, A, V, I

*Fig. 9B*

Alignment of human adenosine receptors

```
AA2AR_human    1            MPIMGSSVYITVELAIAVLAILGNVLVCWAVWLNSNLQNVTNYF   44
AA2BR_human    1           MLLETQDADYVALELVIAALSVAGNVLVCAAVGTANTLQTPTNYF   45
AA3R_human     1    MPNNSTALSLANVTYITMEIFIGLCAIVGNVLVICVVKLNPSLQTTTFYF   50
AA1R_human     1       MP---PSISAFQAAYIGIEVLIALVSVPGNVLVIWAVKVNQALRDATFCF   47

AA2AR_human   45   VVSLAAADIAVGVLAIPFAITISTGFCAACHGCLFIACFVLVLTQSSIFS   94
AA2BR_human   46   LVSLAAADVAVGLFAIPFAITISLGFCTDFYGCLFLACFVLVLTQSSIFS   95
AA3R_human    51   IVSLALADIAVGVLVMPLAIVVSLGITIHFYSCLFMTCLLLIFTHASIMS  100
AA1R_human    48   IVSLAVADVAVGALVIPLAILINIGPQTYFHTCLMVACPVLILTQSSILA   97

AA2AR_human   95   LLAIAIDRYIAIRIPLRYNGLVTGTRAKGIIAICWVLSFAIGLTPMLGWN  144
AA2BR_human   96   LLAVAVDRYLAICVPLRYKSLVTGTRARGVIAVLWVLAFGIGLTPFLGWN  145
AA3R_human   101   LLAIAVDRYLRVKLTVRYKRVTTHRRIWLALGLCWLVSFLVGLTPMFGWN  150
AA1R_human    98   LLAIAVDRYLRVKIPLRYKMVVTPRRAAVAIAGCWILSFVVGLTPMFGWN  147

AA2AR_human  145   --------NCGQPKEGKNHSQGCGEGQVACLFEDVVPMNYMVYFNFFACVL  187
AA2BR_human  146   SKDSATNNCTEPWDGTTNESCC---LVKCLFENVVPMSYMVYFNFFGCVL  192
AA3R_human   151   --------MKLTSEYHRNVT------FLSCQFVSVMRMDYMVYFSFLTWIF  187
AA1R_human   148   --------NLSAVERAWAANGSMGEPVIKCEFEKVISMEYMVYFNFFVWVL  190

AA2AR_human  188   VPLLLMLGVYLRIFLAARRQLKQMESQPLPGERARSTLQKEVHAAKSLAI  237
AA2BR_human  193   PPLLIMLVIYIKIFLVACRQLQRTELMDHS----RTTLQREIHAAKSLAM  238
AA3R_human   188   IPLVVMCAIYLDIFYIIRNKLSLNLSNSK---ETGAFYGREFKTAKSLFL  234
AA1R_human   191   PPLLLMVLIYLEVFYLIRKQLNKKVSASSG--DPQKYYGKELKIAKSLAL  238
```

*Fig. 10A*

```
AA2AR_human  238  IVGLFAICWLPLHIINCFTFFCPDCS-HAPLWLMYLAIVLSHTNSVVNPF  286
AA2BR_human  239  IVGIFALCWLPVHAVNCVTLFQPAQGKNKPKWAMNMAILLSHANSVVNPI  288
AA3R_human   235  VLFLFALSWLPLSIINCIIYFNG----EVPQLVLYMGILLSHANSMMNPI  280
AA1R_human   239  ILFLFALSWLPLHILNCITLFCPSC--HKPSILTYIAIFLTHGNSAMNPI  286

AA2AR_human  287  IYAYRIREFRQTFRKIIRSHVLRQQEPFKAAGTSARVLAAHGSDGEQVSL  336
AA2BR_human  289  VYAYRNRDFRYTFHKIISRYLLCQ----------ADVKSGNGQAGVQPAL  328
AA3R_human   281  VYAYKIKKFKETYLLILKACVVCHP---------SDSLDTSIEKNSE    318
AA1R_human   287  VYAFRIQKFRVTFLKIWNDHFRCQP---------APPIDEDLPEERPDD  326

AA2AR_human  337  RLNGHPPGVWANGSAPHPERRPNGYALGLVSGGSAQESQGNTGLPDVELL  386
AA2BR_human  329  GVGL                                               332
AA3R_human   319                                                     318
AA1R_human   327                                                     326

AA2AR_human  387  SHELKGVCPEPPGLDDPLAQDGAGVS  412
AA2BR_human  333                              332
AA3R_human   319                              318
AA1R_human   327                              326
```

 A  Mutations determined by agonist binding
X  Mutations determined by antagonist binding
▨  Position of transmembrane domains
▧  Position of helix 8

*Fig. 10B*

Alignment of neurotensin receptors

```
NTR1_rat     1   MHLNSSVPQGTPGEPDAQPFSGPQSEMEATFLALSLSNGSGNTSESDTAG            50
NTR1_human   1   MRLNSSAP-GTPGTPAADPFQRAQAGLEEALLAPGFGNASGNASERVLAA            49
NTR2_human   1   METSSP--RPPRPSSNPG---------------------------LS               18
                   *  *    *      *

NTR1_rat    51   PNSDLDVNTDIYSKVLFTAIYLALFVVGTVGNSVTAFTLARKKSLQSLQS           100
NTR1_human  50   PSSELDVNTDIYSKVLVTAVYLALFVVGTVGNTVTAFTLARKKSLQSLQS            99
NTR2_human  19   LDARLGVDTRLWAKVLFTALYALIWALGAAGNALSVHVVLKAR--AGRAG            66
                   *    *  *     *    *      *   *   *

NTR1_rat   101   TVHYHLGSLALSDLLILLLAMPVELYNFIWVHHPWAFGDAGCRGYYFLRD           150
NTR1_human 100   TVHYHLGSLALSDLLILLLAMPVELYNFIWVHHPWAFGDAGCRGYYFLRD           149
NTR2_human  67   RLRHHVLSLALAGLLLLLNGVPVELLYSFVWFHYPWVFGDLGCRGYYFLHE           116
                  *     *   *   *

NTR1_rat   151   ACTYATALNVASLSVERYLAICHPFKAKTLMSRSRTKKFISAIWLASALL           200
NTR1_human 150   ACTYATALNVASLSVERYLAICHPFKAKTLMSRSRTKKFISAIWLASALL           199
NTR2_human 117   LCAYATVLSVAGLSAERCLAVCQPLRARSLLTFRRTRWLVALSWAASLGL           166
                  * *     *           *     *

NTR1_rat   201   AIPMLFTMGLQNR--SGDG--THPGGLVCTPIVDTATVKVVIQVNTFMSFL           247
NTR1_human 200   AVPMLFTMGEQNR--SADG--QHAGGLVCTPTIHTATVKVVIQVNTFMSFI           246
NTR2_human 167   ALPMAVTMGQKHELETADGEPEPASRVCTVLVSRTALQVFIQVNVIVSFV           216
                  * *  *  *                  *                 **
```

*Fig. 11A*

```
NTR1_rat    248  FPMLFCYTSILNTVIANKLTVWVHQAEQ------G------RVCTVGTINGLEHS    289
NTR1_human  247  FPMMVTSYLNTTIANKLTVWVHQAEQ------G------QVCTVGG-----EHS    284
NTR2_human  217  LPLATAFLNGVTVSHLLALCLSQVPSTPGSSTPSRLELLSEEGLLSFI         266
                      *                   *

NTR1_rat    290  ---------PGRVQALRHGVLVLRAVIAFVCWLPYHVR             321
NTR1_human  285  ---------PGRVQALRHGVRLRAVVIAFVVCWLPYHVR            322
NTR2_human  267  VWRKTFTQSGQVSLVRHKDVRRIBSLQRSVQVIRAITVWMYVICWLPYHAR 316
                                    *  *****

NTR1_rat    328  RLMFCYISDEQWTTFLFDFYHYFYMLTNALFYVSSAINPILYNLVSANFR  377
NTR1_human  323  RLMFCYISDEQWTPFLYDFYHYFYMTNALFYVSSTINPILYNLVSANFR   372
NTR2_human  317  RLMKYCYPPDDAWTDPLYNFYHYFYMVCTNTLPYVSSAVTPLLYNAVSSSFR 366
                                *  **  ****** * *****

NTR1_rat    378  QVTLSTLACLCPGWRHRRKRPTFSRKPNSMSSNHAFSTSATRETLY  424
NTR1_human  373  HIFLALACLCPVWRRRRK-RPAFSRKADSVSSNHTLSSNATRETLY  418
NTR2_human  367  KLFLEAVSLC-GEHHPMKRLPPKPQSPTLMDTASGFGD--PPETR    409
                    *               *
```

(a) H103: Thermostability obtained with A, N, S, V, L, M only

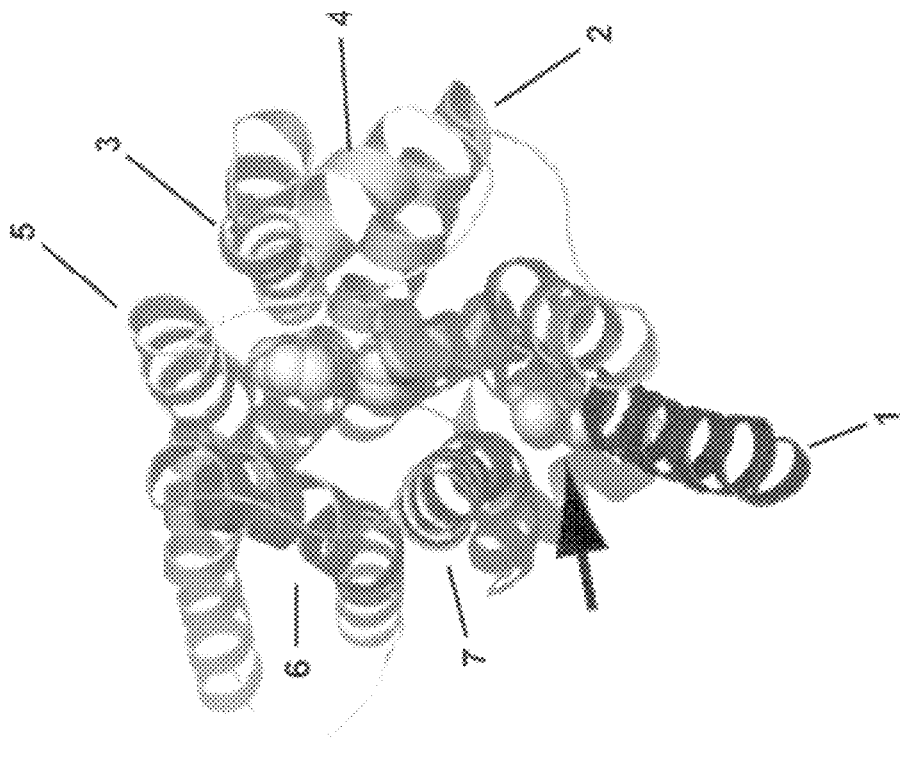
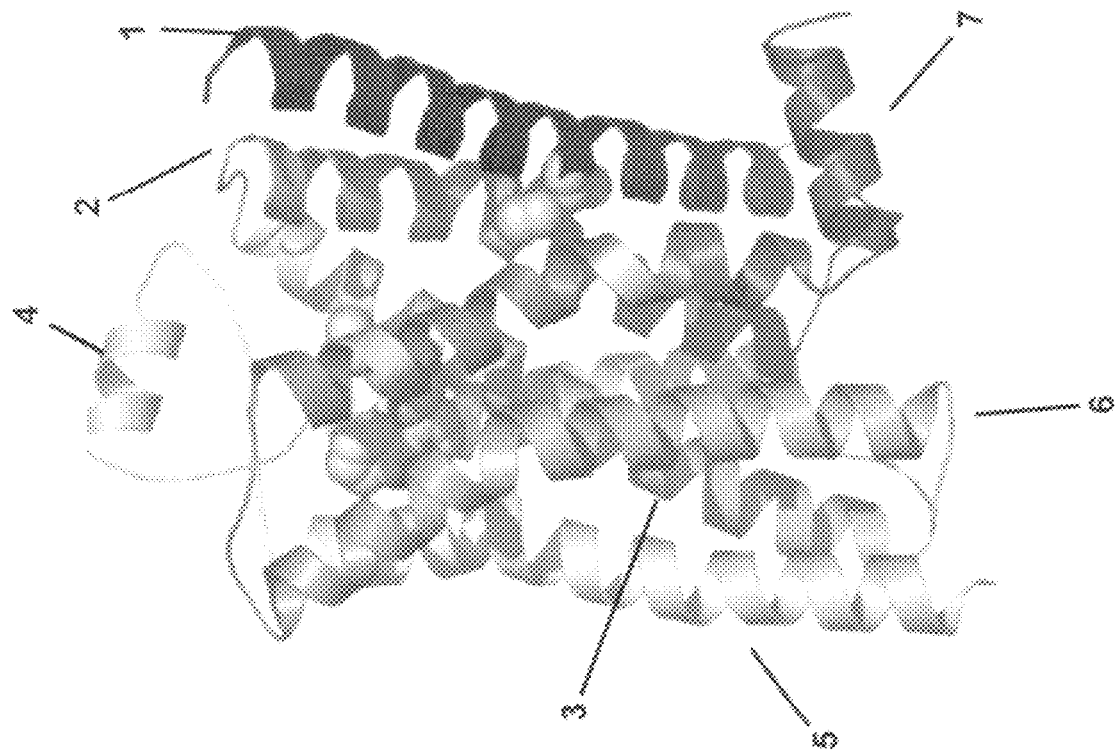
Fig. 18

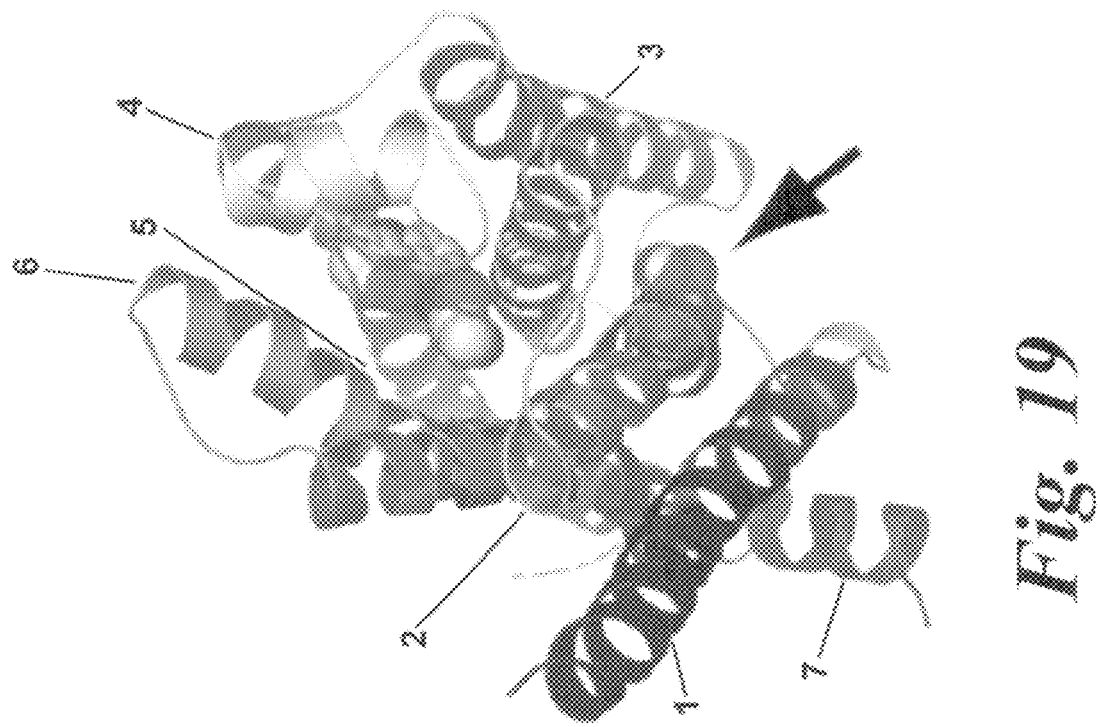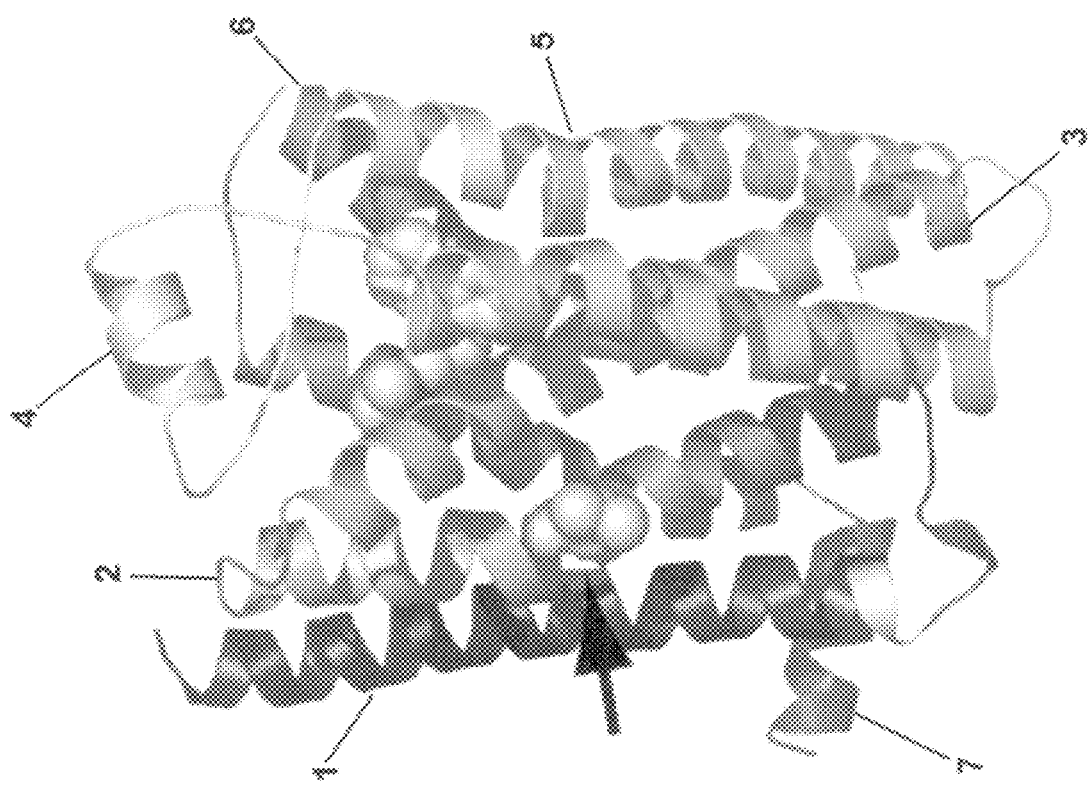
Fig. 19

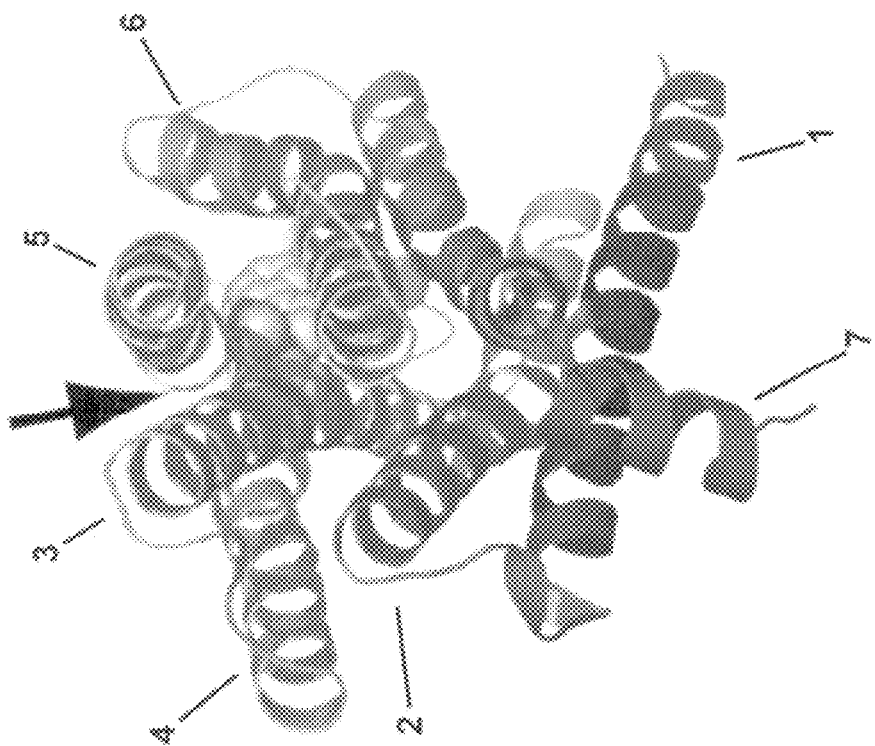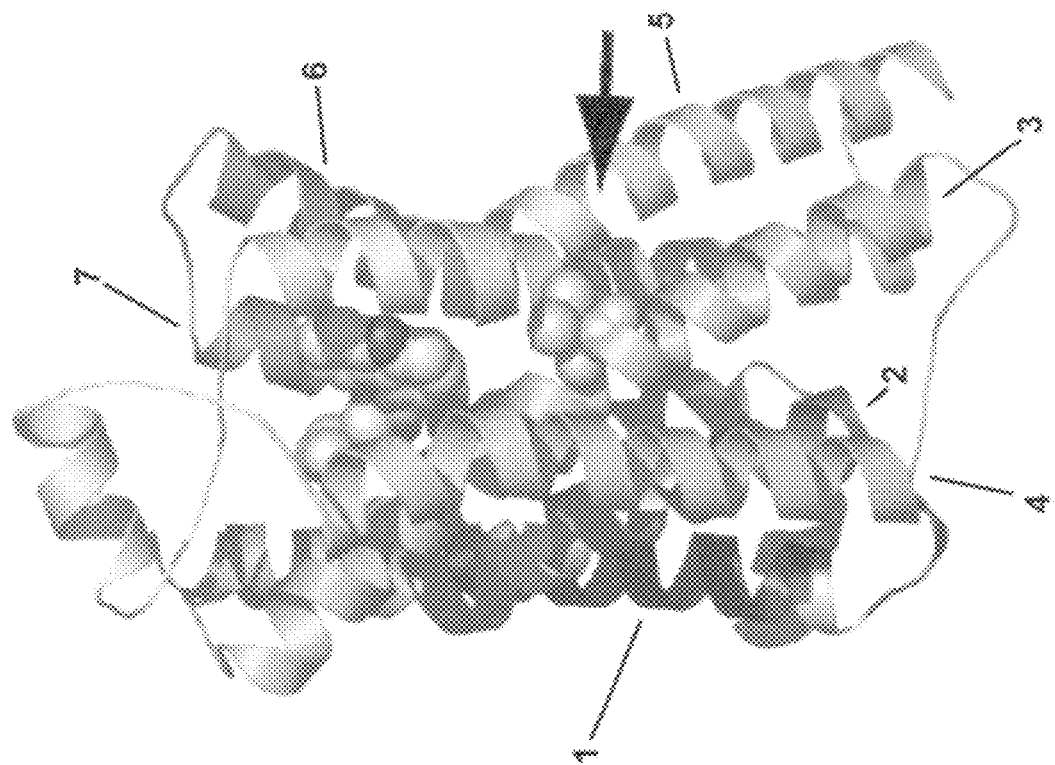
Fig. 21

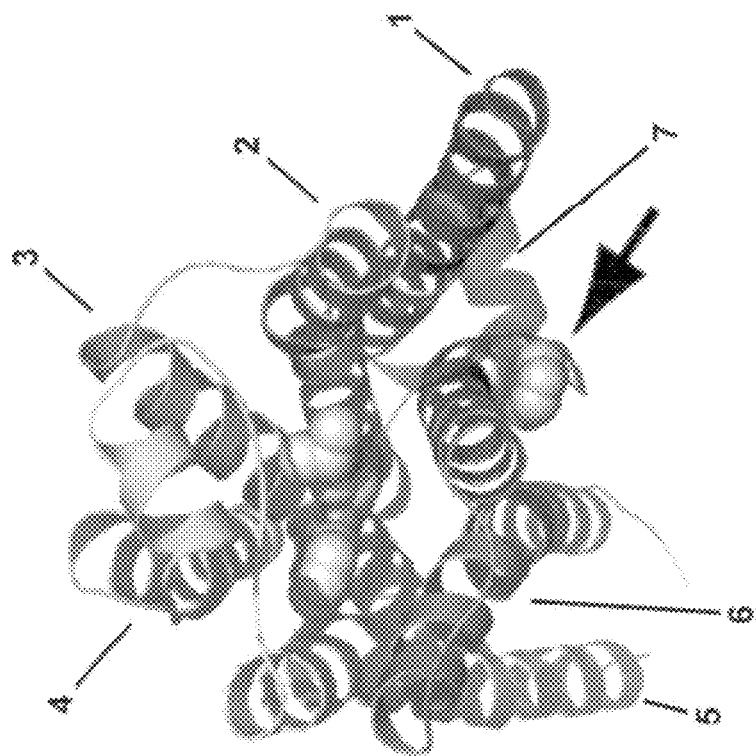
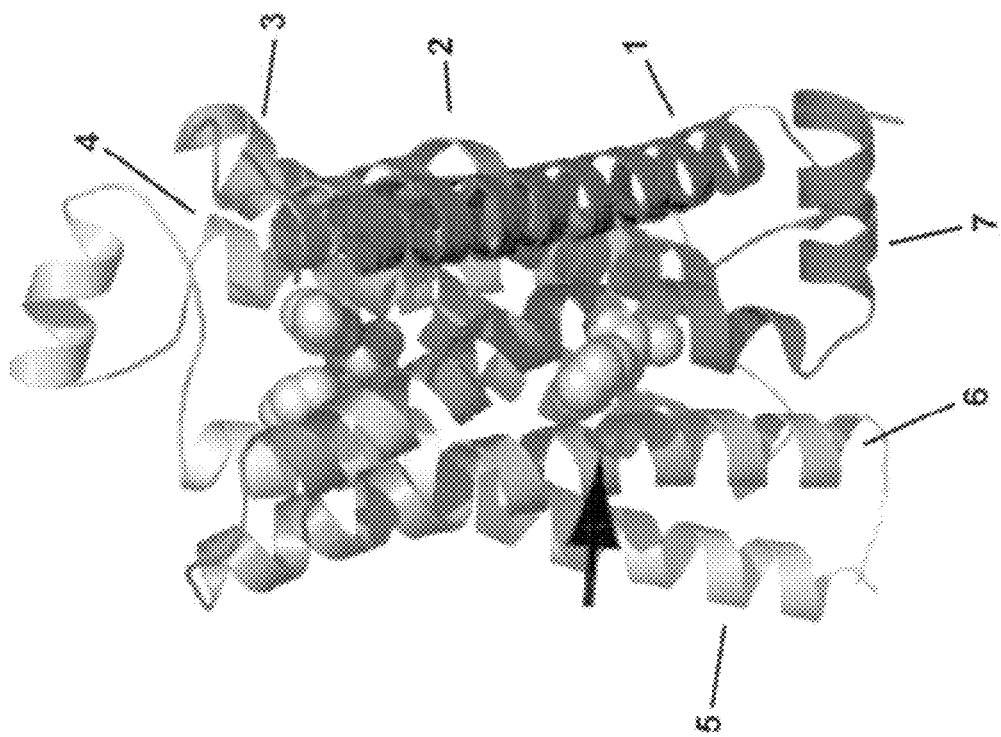
Fig. 22

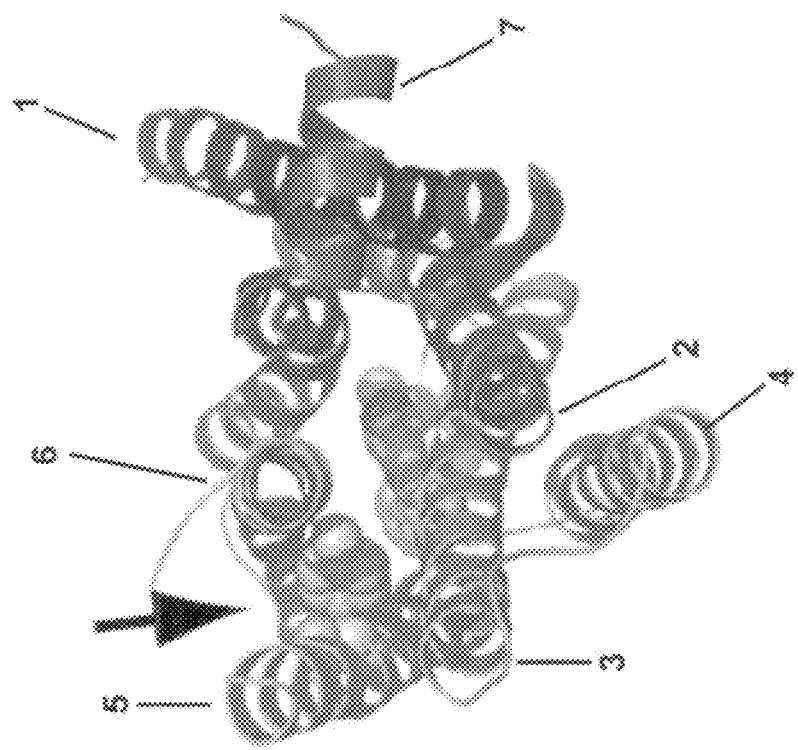
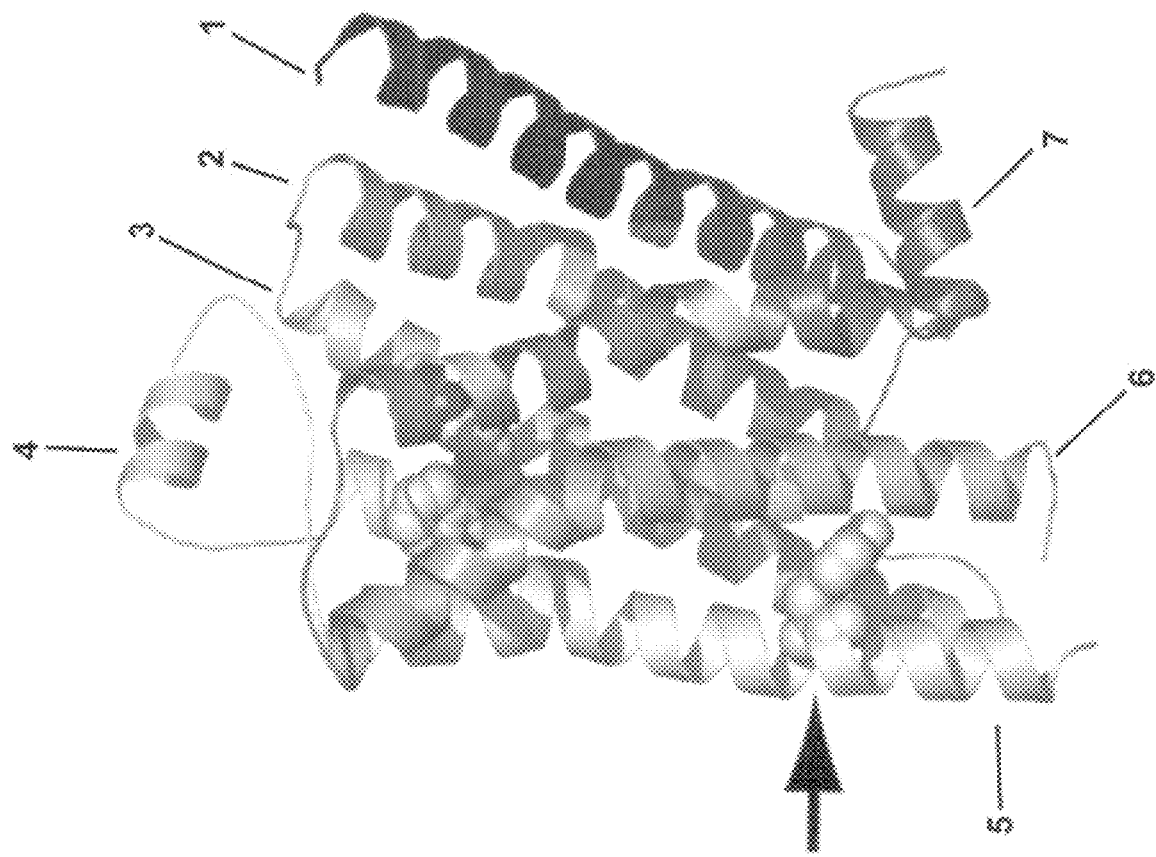
Fig. 23

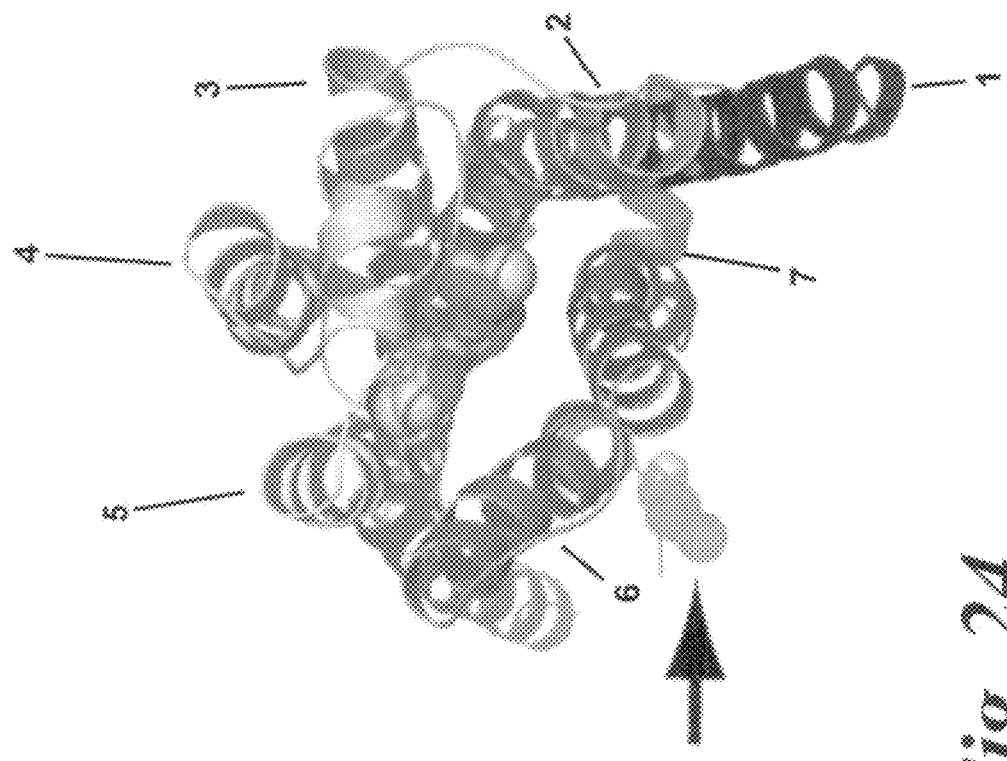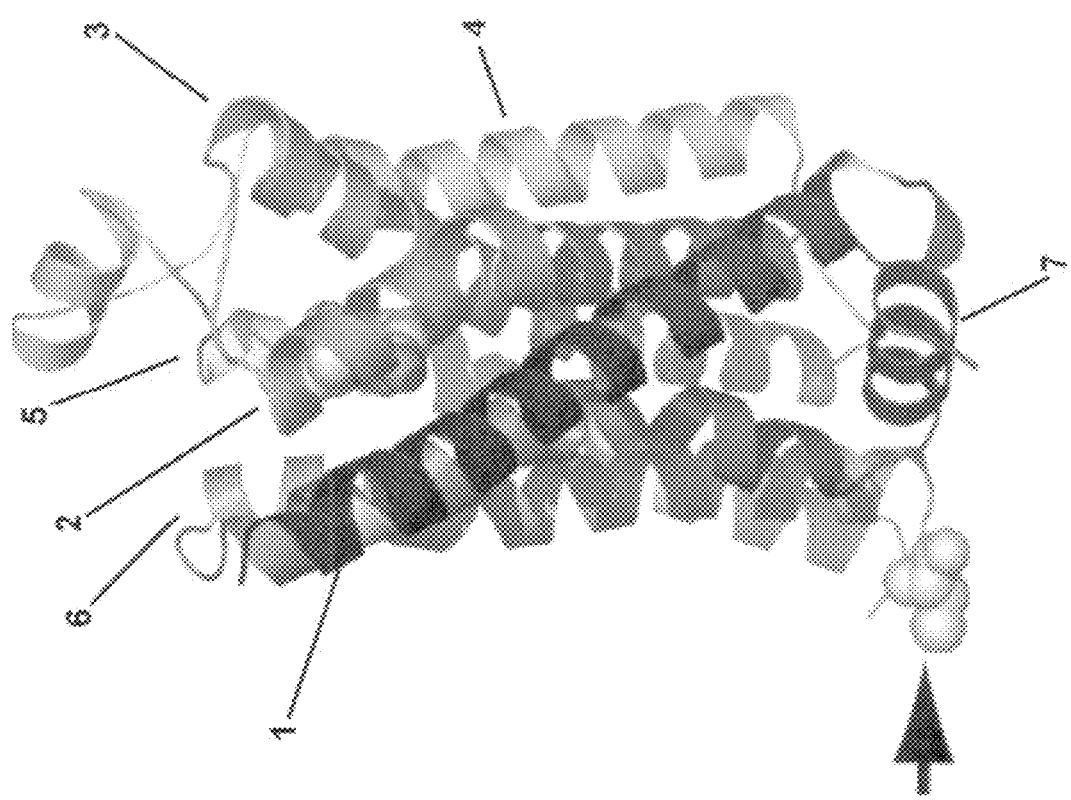
Fig. 24

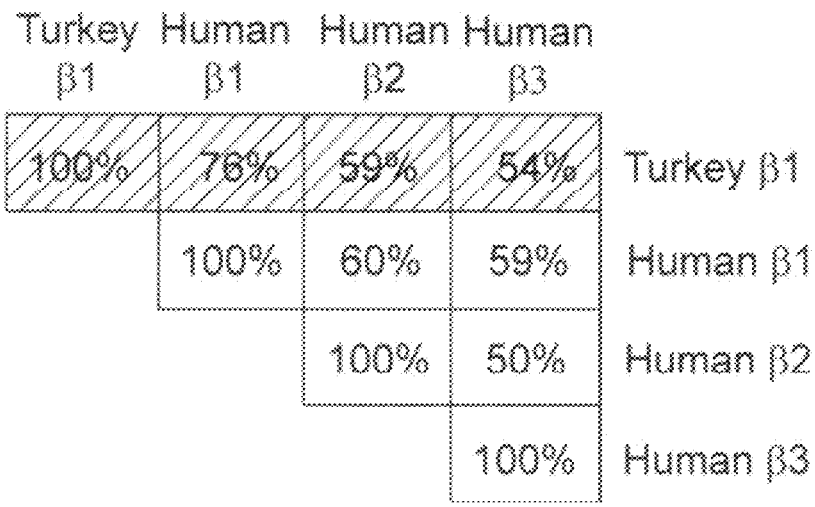
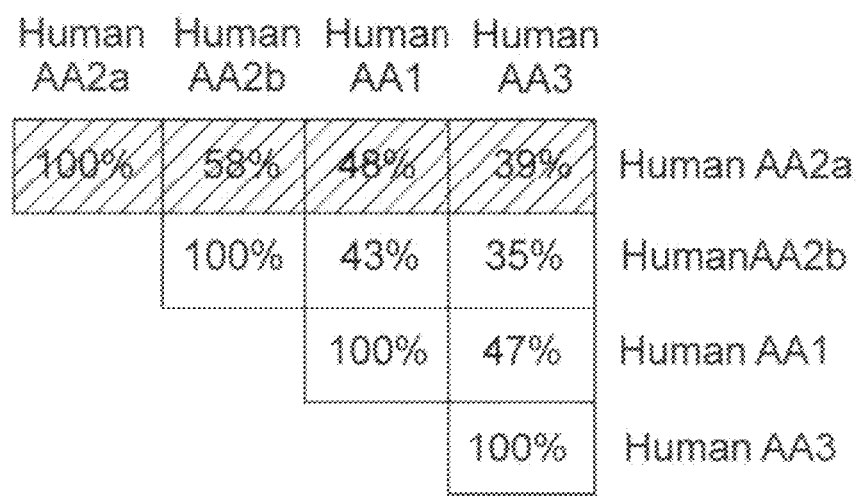
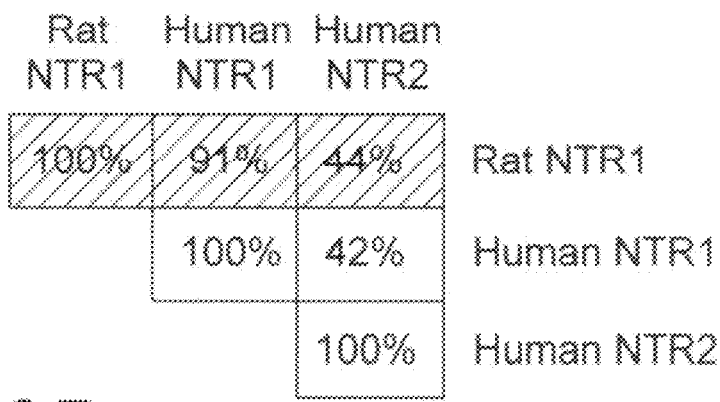
Fig. 27

Alignment of neurotensin receptors

```
NTR1_rat     1    MRLNSSVPGTPGTPGEPDAQPFSGPQSEMEATFLALSLSNGSGNTSESDTAG          50
NTR1_human   1    MRLNSSAP-GTPGTPAADPFQRAQAGLEEALLAPGFGNASGNASERVLAA            49
NTR2_human   1    METSSP--RPPRPSSNPG-----------------------------LS             18
                    * ***    * *  *       *     *       *

NTR1_rat     51   PNSDLDVNTDIYSKVLVTAIYLALFVVGTVGNSVTAFTLARKKSLQSLQS            100
NTR1_human   50   PSSELDVNTDIYSKVLVTAVYLALFVVGTVGNTVTAFTLARKKSLQSLQS             99
NTR2_human   19   LDARLGVDTRLMAKVIPTALYALIWALGAAGNALSVHVVLKAR--AGRAG             66
                    *  **   **  * *  * *    ** ** *

NTR1_rat     101  TVHYHLGSLALSDLLILLLAMPVELYNFIWVHHPWAFGDAGCRGYYFLRD            150
NTR1_human   100  TVHYHLGSLALSDLLILLTLAMPVELYNFIWVHHPWAFGDAGCRGYYFLRD           149
NTR2_human   67   RLRHHVLSLALAGLLLLVGVPVELYSFVWFHYPWVFGDLGCRGYYFVHE             116
                    *** **  ****     *  *   ***** ****  ** *****

NTR1_rat     151  ACTYATALNVASLSVERYLAICHPFKAKTLMSRSRTKKFISAIWLASALL            200
NTR1_human   150  ACTYATALNVASLSVERYLAICHPFKAKTLMSRSRTKKFISAIWLASALL            199
NTR2_human   117  LCAYATVLSVAGLSAERCLAVCQPLRARSLLTERTRWLVALSLVASCLGL             166

NTR1_rat     201  ALPMLFTMGLQNR--SGDG--THPGGLVCTPIVDTATVKVVIQVNTPMSPL           247
NTR1_human   200  AVPMLFTMGEQNR--SADG--QHAGGLVCTPTVHTATVKVVIQVNTPMSFL           246
NTR2_human   167  ALPMAVIMGQKHELFTADGEPEPASRVCTVLVSRTALQVFIQVNVLVSFV            216
                    * *           *  *
```

Fig. 28A

Table (i)

| Agonist | | | Antagonist | | |
|---|---|---|---|---|---|
| Mutation | Expression (%) | Stability (%) | Mutation | Expression (%) | Stability (%) |
| wt | 100 | 100 | wt | 100 | 100 |
| S090A | 151 | 151 | A054L | 90 | 140 |
| G114A | 62 | 143 | V057A | 44 | 144 |
| G118A | 71 | 151 | H075A | 82 | 152 |
| L167A | 41 | 174 | T088A | 67 | 230 |
| A184L | 140 | 150 | G114A | 73 | 153 |
| R199A | 73 | 202 | G118A | 84 | 148 |
| A203L | 42 | 172 | T119A | 90 | 148 |
| L208A | 276 | 215 | K122A | 52 | 153 |
| Q210A | 46 | 155 | G123A | 90 | 158 |
| S213A | 40 | 140 | P149A | 54 | 215 |
| E219A | 96 | 221 | E151A | 63 | 173 |
| R220A | 84 | 250 | G152A | 70 | 156 |
| S223A | 57 | 146 | A203L | 111 | 132 |
| T224A | 142 | 276 | A204L | 40 | 181 |
| Q226A | 119 | 217 | A231L | 90 | 148 |
| K227A | 87 | 222 | L235A | 85 | 140 |
| H230A | 57 | 154 | V239A | 91 | 134 |
| L241A | 139 | 156 | | | |
| P260A | 70 | 169 | | | |
| S263A | 60 | 158 | | | |
| L267A | 40 | 187 | | | |
| L272A | 34 | 157 | | | |
| T279A | 125 | 158 | | | |
| N284A | 64 | 151 | | | |
| Q311A | 49 | 164 | | | |
| P313A | 44 | 148 | | | |
| K315A | 64 | 186 | | | |

*Fig. 29*

MUTANT G-PROTEIN COUPLED RECEPTORS AND METHODS FOR SELECTING THEM

RELATED APPLICATIONS

This application is a continuation of U.S. patent application Ser. No. 16/215,533 filed Dec. 10, 2018, entitled "Mutant G-Protein Coupled Receptors and Methods For Selecting Them," which is a continuation of U.S. patent application Ser. No. 15/716,302 filed Sep. 26, 2017, entitled "Mutant G-Protein Coupled Receptors and Methods For Selecting Them," which is a continuation of U.S. patent application Ser. No. 14/836,820 filed Aug. 26, 2015, entitled "Mutant G-Protein Coupled Receptors and Methods For Selecting Them," which is a continuation of U.S. patent application Ser. No. 13/493,898, filed Jun. 11, 2012, entitled "Mutant G-Protein Coupled Receptors and Methods For Selecting Them," which is a continuation of U.S. patent application Ser. No. 14/450,358, filed Mar. 19, 2010, entitled "Mutant G-Protein Coupled Receptors and Methods For Selecting Them," now U.S. Pat. No. 8,785,135, which is a national stage filing under 35 U.S.C. § 371 of international application PCT/GB2008/000986, filed Mar. 20, 2008, which was published under PCT Article 21(2) in English and claims priority to UK Patent Application No. 0724052.6, filed Dec. 8, 2007, and UK Patent Application No. 0705450.5, filed Mar. 22, 2007, the entire disclosures of each of which are herein incorporated by reference in their entireties.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on May 11, 2020, is named H083070001US05-SEQ-SXT and is 38,471 bytes in size.

The present invention relates to mutant G protein coupled receptors (GPCRs) and methods for selecting those with increased stability. In particular, it relates to the selection and preparation of mutant GPCRs which have increased stability under a particular condition compared to their respective parent proteins. Such proteins are more likely to be crystallisable, and hence amenable to structure determination, than the parent proteins. They are also useful for drug discovery and development studies.

Over the past 20 years the rate of determination of membrane protein structures has gradually increased, but most success has been in crystallising membrane proteins from bacteria rather than from eukaryotes [1]. Bacterial membrane proteins have been easier to overexpress using standard techniques in *Escherichia coli* than eukaryotic membrane proteins [2,3] and the bacterial proteins are sometimes far more stable in detergent, detergent-stability being an essential prerequisite to purification and crystallisation. Genome sequencing projects have also allowed the cloning and expression of many homologues of a specific transporter or ion channel, which also greatly improves the chances of success during crystallisation. However, out of the 120 different membrane protein structures that have been solved to date, there are only seven structures of mammalian integral membrane proteins (blanco.biomol.uci.edu/); five of these membrane proteins were purified from natural sources and are stable in detergent solutions. Apart from the difficulties in overexpressing eukaryotic membrane proteins, they often have poor stability in detergent solutions, which severely restricts the range of crystallisation conditions that can be explored without their immediate denaturation or precipitation. Ideally, membrane proteins should be stable for many days in any given detergent solution, but the detergents that are best suited to growing diffraction-quality crystals tend to be the most destabilising detergents ie those with short aliphatic chains and small or charged head groups. It is also the structures of human membrane proteins that we would like to solve, because these are required to help the development of therapeutic agents by the pharmaceutical industry; often there are substantial differences in the pharmacology of receptors, channels and transporters from different mammals, whilst yeast and bacterial genomes may not include any homologous proteins. There is thus an overwhelming need to develop a generic strategy that will allow the production of detergent-stable eukaryotic integral membrane proteins for crystallisation and structure determination and potentially for other purposes such as drug screening, bioassay and biosensor applications.

Membrane proteins have evolved to be sufficiently stable in the membrane to ensure cell viability, but they have not evolved to be stable in detergent solution, suggesting that membrane proteins could be artificially evolved and detergent-stable mutants isolated [4]. This was subsequently demonstrated for two bacterial proteins, diacylglycerol kinase (DGK) [5,6] and bacteriorhodopsin [7]. Random mutagenesis of DGK identified specific point mutations that increased thermostability and, when combined, the effect was additive so that the optimally stable mutant had a half-life of 35 minutes at 80° C. compared with a half-life of 6 minutes at 55° C. for the native protein [6]. It was shown that the trimer of the detergent-resistant DGK mutant had become stable in SDS and it is thus likely that stabilisation of the oligomeric state played a significant role in thermostabilisation. Although the aim of the mutagenesis was to produce a membrane protein suitable for crystallisation, the structure of DGK has yet to be determined and there have been no reports of successful crystallization. A further study on bacteriorhodopsin by cysteine-scanning mutagenesis along helix B demonstrated that it was not possible to predict which amino acid residues would lead to thermostability upon mutation nor, when studied in the context of the structure, was it clear why thermostabilisation had occurred [7].

GPCRs constitute a very large family of proteins that control many physiological processes and are the targets of many effective drugs. Thus, they are of considerable pharmacological importance. A list of GPCRs is given in Foord et al (2005) *Pharmacol Rev.* 57, 279-288, which is incorporated herein by reference. GPCRs are generally unstable when isolated, and despite considerable efforts, it has not been possible to crystallise any except bovine rhodopsin, which naturally is exceptionally stable.

GPCRs are druggable targets, and reference is made particularly to Overington et al (2006) *Nature Rev. Drug Discovery* 5, 993-996 which indicates that over a quarter of present drugs have a GPCR as a target.

GPCRs are thought to exist in multiple distinct conformations which are associated with different pharmacological classes of ligand such as agonists and antagonists, and to cycle between these conformations in order to function (Kenakin T. (1997) *Ann NY Acad Sci* 812, 116-125).

It will be appreciated that the methods of the invention do not include a method as described in D'Antona et al., including binding of [$^3$H]CP55940 to a constitutively inactive mutant human cannabinoid receptor 1 (T210A) in which the Thr residue at position 210 is replaced with an Ala residue.

The listing or discussion of an apparently prior-published document in this specification should not necessarily be taken as an acknowledgement that the document is part of the state of the art or is common general knowledge.

We have realised that there are two serious problems associated with trying to crystallise GPCRs, namely their lack of stability in detergent and the fact that they exist in multiple conformations. In order to function GPCRs have evolved to cycle through at least two distinct conformations, the agonist-bound form and the antagonist-bound form, and changes between these two conformations can occur spontaneously in the absence of ligand. It is thus likely that any purified receptors populate a mixture of conformations. Just adding ligands to GPCRs during crystallisation trials has not resulted in their structure determination. To improve the likelihood of crystallisation, we therefore selected mutations that improved the stability of the GPCR and, in addition, preferentially locked the receptor in a specific biologically relevant conformation.

We decided to see whether stabilisation of a GPCR in a particular, biologically relevant conformation was possible and whether the effect was sufficiently great that it would significantly improve the chances of obtaining diffraction-quality crystals. In Example 1, the β1-adrenergic receptor (βAR) from turkey erythrocytes [8] was chosen as a test subject for this study for a number of reasons. The βAR is a G protein-coupled receptor (GPCR) that has well-developed pharmacology with many ligands commercially available and in a radiolabelled form. In addition, overexpression of βAR has been particularly successful using the baculovirus expression system and it can be purified in milligram quantities in a functional form [9]. In Example 2, a human adenosine receptor was used, and in Example 3, a rat neurotensin receptor was used.

Method for Selecting Mutant GPCRs with Increased Stability

A first aspect of the invention provides a method for selecting a mutant G-protein coupled receptor (GPCR) with increased stability, the method comprising
  (a) providing one or more mutants of a parent GPCR,
  (b) selecting a ligand, the ligand being one which binds to the parent GPCR when the GPCR is residing in a particular conformation,
  (c) determining whether the or each mutant GPCR has increased stability with respect to binding the selected ligand compared to the stability of the parent GPCR with respect to binding that ligand, and
  (d) selecting those mutants that have an increased stability compared to the parent GPCR with respect to binding of the selected ligand.

The inventors have appreciated that, in order to improve the likelihood of crystallisation of a GPCR in a biologically relevant form (which is therefore pharmacologically useful), it is desirable not only to increase the stability of the protein, but also for the protein to have this increased stability when in a particular conformation. The conformation is determined by a selected ligand, and is a biologically relevant conformation in particular a pharmacologically relevant conformation. Thus, the method of the invention may be considered to be a method for selecting mutants of a GPCR which have increased stability of a particular conformation, for example they may have increased conformational thermostability. The method may be used to create stable, conformationally locked GPCRs by mutagenesis. The selected mutant GPCRs are effectively purer forms of the parent molecules in that a much higher proportion of them occupies a particular conformational state. The deliberate selection of a chosen receptor conformation resolved from other conformations by use of a ligand (or ligands) that bind preferentially to this conformation is therefore an important feature of the invention. The method may also be considered to be a method for selecting mutant GPCRs which are more tractable to crystallisation.

Thus the invention includes a method for selecting a mutant G-protein coupled receptor (GPCR) with increased stability, the method comprising
  (a) providing one or more mutants of a parent GPCR,
  (b) selecting a ligand, the ligand being one which binds to the parent GPCR when the GPCR is residing in a particular conformation,
  (c) determining whether the or each mutant GPCR when residing in the particular conformation has increased stability with respect to binding the selected ligand compared to the stability of the parent GPCR when residing in the same particular conformation with respect to binding that ligand, and
  (d) selecting those mutants that have an increased stability compared to the parent GPCR with respect to binding of the selected ligand.

In a review of the druggable genome by Hopkins & Groom (2002) *Nature Rev. Drug Discovery* 1, 727-730, Table 1 contains a list of protein families many of which are GPCRs. Overington et al (2006) *Nature Rev. Drug Discovery* 5, 993-996 provides more details of drug targets, and FIG. 1 indicates that more than a quarter of current drugs target GPCRs. There are 52 GPCR targets for orally available drugs out of a total of 186 total targets in this category.

Suitable GPCRs for use in the practice of the invention include, but are not limited to β-adrenergic receptor, adenosine receptor, in particular adenosine $A_{2a}$ receptor, and neurotensin receptor (NTR). Other suitable GPCRs are well known in the art and include those listed in Hopkins & Groom supra. In addition, the International Union of Pharmacology produce a list of GPCRs (Foord et al (2005) *Pharmacol. Rev.* 57, 279-288, incorporated herein by reference and this list is periodically updated at www.iuphar-db.org/GPCR/ReceptorFamiliesForward. It will be noted that GPCRs are divided into different classes, principally based on their amino acid sequence similarities. They are also divided into families by reference to the natural ligands to which they bind. All GPCRs are included in the scope of the invention.

The amino acid sequences (and the nucleotide sequences of the cDNAs which encode them) of many GPCRs are readily available, for example by reference to GenBank. In particular, Foord et al supra gives the human gene symbols and human, mouse and rat gene IDs from Entrez Gene (www.ncbi.nlm.nih.gov/entrez). It should be noted, also, that because the sequence of the human genome is substantially complete, the amino acid sequences of human GPCRs can be deduced therefrom.

Although the GPCR may be derived from any source, it is particularly preferred if it is from a eukaryotic source. It is particularly preferred if it is derived from a vertebrate source such as a mammal or a bird. It is particularly preferred if the GPCR is derived from rat, mouse, rabbit or dog or non-human primate or man, or from chicken or turkey. For the avoidance of doubt, we include within the meaning of "derived from" that a cDNA or gene was originally obtained using genetic material from the source, but that the protein may be expressed in any host cell subsequently. Thus, it will be plain that a eukaryotic GPCR (such as an avian or mammalian GPCR) may be expressed in a prokaryotic host cell, such as *E. coli*, but be considered to be avian- or mammalian-derived, as the case may be.

In some instances, the GPCR may be composed of more than one different subunit. For example, the calcitonin gene-related peptide receptor requires the binding of a single transmembrane helix protein (RAMP1) to acquire its physiological ligand binding characteristics. Effector, accessory, auxiliary or GPCR-interacting proteins which combine with the GPCR to form or modulate a functional complex are well known in the art and include, for example, receptor kinases, G-proteins and arrestins (Bockaert et al (2004) *Curr Opinion Drug Discov and Dev* 7, 649-657).

The mutants of the parent GPCR may be produced in any suitable way and provided in any suitable form. Thus, for example, a series of specific mutants of the parent protein may be made in which each amino acid residue in all or a part of the parent protein is independently changed to another amino acid residue. For example, it may be convenient to make mutations in those parts of the protein which are predicted to be membrane spanning. The three-dimensional structure of rhodopsin is known (Li et al (2004) *J Mol Biol* 343, 1409-1438; Palczewski et al (2000) Science 289, 739-745), and it is possible to model certain GPCRs using this structure. Thus, conveniently, parts of the GPCR to mutate may be based on modelling. Similarly, computer programs are available which model transmembrane regions of GPCRs based on hydrophobicity (Kyle & Dolittle (1982) *J. Mol. Biol.* 157, 105-132), and use can be made of such models when selecting parts of the protein to mutate. Conventional site-directed mutagenesis may be employed, or polymerase chain reaction-based procedures well known in the art may be used. It is possible, but less desirable, to use ribosome display methods in the selection of the mutant protein.

Typically, each selected amino acid is replaced by Ala (ie Ala-scanning mutagenesis), although it may be replaced by any other amino acid. If the selected amino acid is Ala, it may conveniently be replaced by Leu. Alternatively, the amino acid may be replaced by Gly (ie Gly-scanning mutagenesis), which may allow a closer packing of neighbouring helices that may lock the protein in a particular conformation. If the selected amino acid is Gly, it may conveniently be replaced by Ala.

Although the amino acid used to replace the given amino acid at a particular position is typically a naturally occurring amino acid, typically an "encodeable" amino acid, it may be a non-natural amino acid (in which case the protein is typically made by chemical synthesis or by use of non-natural amino-acyl tRNAs). An "encodeable" amino acid is one which is incorporated into a polypeptide by translation of mRNA. It is also possible to create non-natural amino acids or introduce non-peptide linkages at a given position by covalent chemical modification, for example by post-translational treatment of the protein or semisynthesis. These post-translational modifications may be natural, such as phosphorylation, glycosylation or palmitoylation, or synthetic or biosynthetic.

Alternatively, the mutants may be produced by a random mutagenesis procedure, which may be of the whole protein or of a selected portion thereof. Random mutagenesis procedures are well known in the art.

Conveniently, the mutant GPCR has one replaced amino acid compared to the parent protein (ie it is mutated at one amino acid position). In this way, the contribution to stability of a single amino acid replacement may be assessed. However, the mutant GPCR assayed for stability may have more than one replaced amino acid compared to the parent protein, such as 2 or 3 or 4 or 5 or 6 replacements.

As is discussed in more detail below, combinations of mutations may be made based on the results of the selection method. It has been found that in some specific cases combining mutations in a single mutant protein leads to a further increase in stability. Thus, it will be appreciated that the method of the invention can be used in an iterative way by, for example, carrying it out to identify single mutations which increase stability, combining those mutations in a single mutant GPCRs which is the GPCR then provided in part (a) of the method. Thus, multiply-mutated mutant proteins can be selected using the method.

The parent GPCR need not be the naturally occurring protein. Conveniently, it may be an engineered version which is capable of expression in a suitable host organism, such as *Escherichia coli*. For example, as described in Example 1, a convenient engineered version of the turkey β-adrenergic receptor is one which is truncated and lacks residues 1-33 of the amino acid sequence (ie βAR$_{34-424}$). The parent GPCR may be a truncated form of the naturally occurring protein (truncated at either or both ends), or it may be a fusion, either to the naturally occurring protein or to a fragment thereof. Alternatively or additionally, the parent GPCR, compared to a naturally-occurring GPCR, may be modified in order to improve, for example, solubility, proteolytic stability (eg by truncation, deletion of loops, mutation of glycosylation sites or mutation of reactive amino acid side chains such as cysteine). In any event, the parent GPCR is a protein that is able to bind to the selected ligand which ligand is one which is known to bind the naturally occurring GPCR. Conveniently, the parent GPCR is one which, on addition of an appropriate ligand, can affect any one or more of the downstream activities which are commonly known to be affected by G-protein activation.

However, it will be appreciated that the stability of the mutant is to be compared to a parent in order to be able to assess an increase in stability.

A ligand is selected, the ligand being one which binds to the parent GPCR when residing in a particular conformation. Typically, the ligand will bind to one conformation of the parent GPCR (and may cause the GPCR to adopt this conformation), but does not bind as strongly to another conformation that the GPCR may be able to adopt. Thus, the presence of the ligand may be considered to encourage the GPCR to adopt the particular conformation. Thus, the method may be considered to be a way of selecting mutant GPCRs which are trapped in a conformation of biological relevance (eg ligand bound state), and which are more stable with respect to that conformation.

Preferably the particular conformation in which the GPCR resides in step (c) corresponds to the class of ligand selected in step (b).

Preferably the selected ligand is from the agonist class of ligands and the particular conformation is an agonist conformation, or the selected ligand is from the antagonist class of ligands and the particular conformation is an antagonist conformation.

Preferably the selected ligand is from the agonist class of ligands and the particular conformation in which the GPCR resides in step (c) is the agonist conformation. Preferably, the selected ligand binding affinity for the mutant receptor should be equal to or greater than that for the wild type receptor; mutants that exhibit significantly reduced binding to the selected ligand are typically rejected.

By "ligand" we include any molecule which binds to the GPCR and which causes the GPCR to reside in a particular conformation. The ligand preferably is one which causes more than half of the GPCR molecules overall to be in a particular conformation.

Many suitable ligands are known.

Typically, the ligand is a full agonist and is able to bind to the GPCR and is capable of eliciting a full (100%) biological response, measured for example by G-protein coupling, downstream signalling events or a physiological output such as vasodilation. Thus, typically, the biological response is GDP/GTP exchange in a G-protein, followed by stimulation of the linked effector pathway. The measurement, typically, is GDP/GTP exchange or a change in the level of the end product of the pathway (eg cAMP, cGMP or inositol phosphates). The ligand may also be a partial agonist and is able to bind to the GPCR and is capable of eliciting a partial (<100%) biological response.

The ligand may also be an inverse agonist, which is a molecule which binds to a receptor and reduces its basal (ie unstimulated by agonist) activity sometimes even to zero.

The ligand may also be an antagonist, which is a molecule which binds to a receptor and blocks binding of an agonist, so preventing a biological response. Inverse agonists and partial agonists may under certain assay conditions be antagonists.

The above ligands may be orthosteric, by which we include the meaning that they combine with the same site as the endogenous agonist; or they may be allosteric or allotopic, by which we include the meaning that they combine with a site distinct from the orthosteric site. The above ligands may be syntopic, by which we include the meaning that they interact with other ligand(s) at the same or an overlapping site. They may be reversible or irreversible.

In relation to antagonists, they may be surmountable, by which we include the meaning that the maximum effect of agonist is not reduced by either pre-treatment or simultaneous treatment with antagonist; or they may be insurmountable, by which we include the meaning that the maximum effect of agonist is reduced by either pre-treatment or simultaneous treatment with antagonist; or they may be neutral, by which we include the meaning the antagonist is one without inverse agonist or partial agonist activity. Antagonists typically are also inverse agonists.

Ligands for use in the invention may also be allosteric modulators such as positive allosteric modulators, potentiators, negative allosteric modulators and inhibitors. They may have activity as agonists or inverse agonists in their own right or they may only have activity in the presence of an agonist or inverse agonist in which case they are used in combination with such molecules in order to bind to the GPCR.

Neubig et al (2003) *Pharmacol. Rev.* 55, 597-606, incorporated herein by reference, describes various classes of ligands.

Preferably, the above-mentioned ligands are small organic or inorganic moieties, but they may be peptides or polypeptides. Typically, when the ligand is a small organic or organic moiety, it has a $M_r$ of from 50 to 2000, such as from 100 to 1000, for example from 100 to 500.

Typically, the ligand binds to the GPCR with a $K_d$ of from mM to pM, such as in the range of from μM (micromolar) to nM. Generally, the ligands with the lowest Kd are preferred.

Small organic molecule ligands are well known in the art, for example see the Examples below. Other small molecule ligands include 5HT which is a full agonist at the 5HT1A receptor; eltoprazine which is a partial agonist at the 5HT1A receptor (see Newman-Tancredi et al (1997) *Neurophamacology* 36, 451-459); (+)-butaclamol and spiperone are dopamine D2 receptor inverse agonists (see Roberts & Strange (2005) *Br. J. Pharmacol.* 145, 34-42); and WIN55212-3 is a neutral antagonist of CB2 (Savinainen et al (2005) *Br. J. Pharmacol.* 145, 636-645).

The ligand may be a peptidomimetic, a nucleic acid, a peptide nucleic acid (PNA) or an aptamer. It may be an ion such as $Na^+$ or $Zn^{2+}$, a lipid such as oleamide, or a carbohydrate such as heparin.

The ligand may be a polypeptide which binds to the GPCR. Such polypeptides (by which we include oligopeptides) are typically from $M_r$ 500 to $M_r$ 50,000, but may be larger. The polypeptide may be a naturally occurring GPCR-interacting protein or other protein which interacts with the GPCR, or a derivative or fragment thereof, provided that it binds selectively to the GPCR in a particular conformation. GPCR-interacting proteins include those associated with signalling and those associated with trafficking, which often act via PDZ domains in the C terminal portion of the GPCR.

Polypeptides which are known to bind certain GPCRs include any of a G protein, an arrestin, a RGS protein, G protein receptor kinase, a RAMP, a 14-3-3 protein, a NSF, a periplakin, a spinophilin, a GPCR kinase, a receptor tyrosine kinase, an ion channel or subunit thereof, an ankyrin and a Shanks or Homer protein. Other polypeptides include NMDA receptor subunits NR1 or NR2a, calcyon, or a fibronectin domain framework. The polypeptide may be one which binds to an extracellular domain of a GPCR, such as fibulin-1. The polypeptide may be another GPCR, which binds to the selected GPCR in a hetero-oligomer. A review of protein-protein interactions at GPCRs is found in Milligan & White (2001) *Trends Pharmacol. Sci.* 22, 513-518, or in Bockaert et al (2004) *Curr. Opinion Drug Discov. Dev.* 7, 649-657 incorporated herein by reference.

The polypeptide ligand may conveniently be an antibody which binds to the GPCR. By the term "antibody" we include naturally-occurring antibodies, monoclonal antibodies and fragments thereof. We also include engineered antibodies and molecules which are antibody-like in their binding characteristics, including single chain Fv (scFv) molecules and domain antibodies (dAbs). Mention is also made of camelid antibodies and engineered camelid antibodies. Such molecules which bind GPCRs are known in the art and in any event can be made using well known technology. Suitable antibodies include ones presently used in radioimmunoassay (RIAs) for GPCRs since they tend to recognise conformational epitopes.

The polypeptide may also be a binding protein based on a modular framework, such as ankyrin repeat proteins, armadillo repeat proteins, leucine rich proteins, tetratriopeptide repeat proteins or Designed Ankyrin Repeat Proteins (DARPins) or proteins based on lipocalin or fibronectin domains or Affilin scaffolds based on either human gamma crystalline or human ubiquitin.

In one embodiment of the invention, the ligand is covalently joined to the GPCR, such as a G-protein or arrestin fusion protein. Some GPCRs (for example thrombin receptor) are cleaved N-terminally by a protease and the new N-terminus binds to the agonist site. Thus, such GPCRs are natural GPCR-ligand fusions.

It will be appreciated that the use of antibodies, or other "universal" binding polypeptides (such as G-proteins which are known to couple with many different GPCRs) may be particularly advantageous in the use of the method on "orphan" GPCRs for which the natural ligand, and small molecule ligands, are not known.

Once the ligand has been selected, it is then determined whether the or each mutant GPCR has increased stability with respect to binding the selected ligand compared to the parent GPCR with respect to binding that ligand. It will be appreciated that this step (c) is one in which it is determined whether the or each mutant GPCR has an increased stability (compared to its parent) for the particular conformation which is determined by the selected ligand. Thus, the mutant GPCR has increased stability with respect to binding the selected ligand as measured by ligand binding or whilst binding the selected ligand. As is discussed below, it is particularly preferred if the increased stability is assessed whilst binding the selected ligand.

The increased stability is conveniently measured by an extended lifetime of the mutant under the imposed conditions which may lead to instability (such as heat, harsh detergent conditions, chaotropic agents and so on). Destabilisation under the imposed condition is typically determined by measuring denaturation or loss of structure. As is discussed below, this may manifest itself by loss of ligand binding ability or loss of secondary or tertiary structure indicators.

As is described with respect to FIG. 12 below (which depicts a particular, preferred embodiment), there are different assay formats which may be used to determine stability of the mutant GPCR.

In one embodiment the mutant GPCR may be brought into contact with a ligand before being subjected to a procedure in which the stability of the mutant is determined (the mutant GPCR and ligand remaining in contact during the test period). Thus, for example, when the method is being used to select for mutant GPCRs which in one conformation bind to a ligand and which have improved thermostability, the receptor is contacted with the ligand before being heated, and then the amount of ligand bound to the receptor following heating may be used to express thermostability compared to the parent receptor. This provides a measure of the amount of the GPCR which retains ligand binding capacity following exposure to the denaturing conditions (eg heat), which in turn is an indicator of stability.

In an alternative (but less preferred) embodiment, the mutant GPCR is subjected to a procedure in which the stability of the mutant is determined before being contacted with the ligand. Thus, for example, when the method is being used to select for mutant membrane receptors which in one conformation bind to a ligand and which have improved thermostability, the receptor is heated first, before being contacted with the ligand, and then the amount of ligand bound to the receptor may be used to express thermostability. Again, this provides a measure of the amount of the GPCR which retains ligand binding capacity following exposure to the denaturing conditions.

In both embodiments, it will be appreciated that the comparison of stability of the mutant is made by reference to the parent molecule under the same conditions.

It will be appreciated that in both of these embodiments, the mutants that are selected are ones which have increased stability when residing in the particular conformation compared to the parent protein.

The preferred route may be dependent upon the specific GPCR, and will be dependent upon the number of conformations accessible to the protein in the absence of ligand. In the embodiment described in FIG. 12, it is preferred if the ligand is present during the heating step because this increases the probability that the desired conformation is selected.

From the above, it will be appreciated that the invention includes a method for selecting a mutant GPCR with increased thermostability, the method comprising (a) providing one or more mutants of a parent GPCR, (b) selecting an antagonist or an agonist which binds the parent GPCR, (c) determining whether the or each mutant has increased thermostability when in the presence of the said antagonist or agonist by measuring the ability of the mutant GPCR to bind the selected said antagonist or agonist at a particular temperature and after a particular time compared to the parent GPCR and (d) selecting those mutant GPCRs that bind more of the selected said antagonist or agonist at the particular temperature and after the particular time than the parent GPCR under the same conditions. In step (c), a fixed period of time at the particular temperature is typically used in measuring the ability of the mutant GPCR to bind the selected said antagonist or agonist. In step (c), typically a temperature and a time is chosen at which binding of the selected said antagonist or agonist by the parent GPCR is reduced by 50% during the fixed period of time at that temperature (which is indicative that 50% of the receptor is inactivated; "quasi" Tm).

Conveniently, when the ligand is used to assay the GPCR (ie used to determine if it is in a non-denatured state), the ligand is detectably labelled, eg radiolabelled or fluorescently labelled. In another embodiment, ligand binding can be assessed by measuring the amount of unbound ligand using a secondary detection system, for example an antibody or other high affinity binding partner covalently linked to a detectable moiety, for example an enzyme which may be used in a colorimetric assay (such as alkaline phosphatase or horseradish peroxidase). FRET methodology may also be used. It will be appreciated that the ligand used to assay the mutant GPCR in determining its stability need not be the same ligand as selected in step (b) of the method.

Although it is convenient to measure the stability of the parent and mutant GPCR by using the ability to bind a ligand as an indicator of the presence of a non-denatured protein, other methods are known in the art. For example, changes in fluorescence spectra can be a sensitive indicator of unfolding, either by use of intrinsic tryptophan fluorescence or the use of extrinsic fluorescent probes such as 1-anilino-8-napthaleneulfonate (ANS), for example as implemented in the Thermofluor™ method (Mezzasalma et al, J Biomol Screening, 2007, April; 12(3):418-428). Proteolytic stability, deuterium/hydrogen exchange measured by mass spectrometry, blue native gels, capillary zone electrophoresis, circular dichroism (CD) spectra and light scattering may also be used to measure unfolding by loss of signals associated with secondary or tertiary structure. However, all these methods require the protein to be purified in reasonable quantities before they can be used (eg high pmol/nmol quantities), whereas the method described in the Examples makes use of pmol amounts of essentially unpurified GPCR.

In a preferred embodiment, in step (b) two or more ligands of the same class are selected, the presence of each causing the GPCR to reside in the same particular conformation. Thus, in this embodiment, one or more ligands (whether natural or non-natural) of the same class (eg full agonist or partial agonist or antagonist or inverse agonist) may be used. Including multiple ligands of the same class in this process, whether in series or in parallel, minimises the theoretical risk of inadvertently engineering and selecting multiply mutated receptor conformations substantially different to the parent, for example in their binding site, but still able, due to compensatory changes, to bind ligand. The following steps may be used to mitigate this risk:

1. Select a chemically distinct set (eg n=2-5) of ligands, in a common pharmacological class as evidenced by for example a binding or functional or spectroscopic assay. These ligands should be thought to bind to a common spatial region of the receptor, as evidenced for example by competitive binding studies using wild type and/or mutated receptors, and/or by molecular modelling, although they will not necessarily express a common pharmacophore.

2. Make single or multiple receptor mutants intended to increase stability, and assay for tight binding using the full set of ligands. The assays can be parallelised, multiplexed or run in series.

3. Confirm authenticity of stabilised receptor mutant by measurement for example of the binding isotherm for each ligand, and by measurement of the stability shift with ligand (the window should typically be narrowed compared to wild type).

In order to guard against changes in apparent affinity caused by perturbations to the binding site upon mutation, preferably ligands of the same pharmacological class, but different chemical class, should be used to profile the receptor. These should typically show similar shifts in affinity (mutant versus parent, e.g. wild type) in spite of having different molecular recognition properties. Binding experiments should preferably be done using labelled ligand within the same pharmacological class.

Nonetheless it should be recognised that conformational substrates may exist that are specific to chemical classes of ligand within the same pharmacological class, and these may be specifically stabilised in the procedure depending on the chemical class of the selected ligand.

Typically the selected ligand binds to the mutant GPCR with a similar potency to its binding to the parent GPCR. Typically, the $K_d$ values for the particular ligand binding the mutant GPCR and the parent GPCR are within 5-10 fold of each other, such as within 2-3 fold. Typically, the binding of the ligand to the mutant GPCR compared to the parent GPCR would be not more than 5 times weaker and not more than 10 times stronger.

Typically, mutant receptors which have been stabilised in the selected conformation should bind the selected ligand with approximately equal affinity (that is to say typically within 2-3 fold) or greater affinity than does the parent receptor. For agonist-conformation mutants, the mutants typically bind the agonists with the same or higher affinity than the parent GPCR and typically bind antagonists with the same or lower affinity than the parent GPCR. Similarly for antagonist-conformation mutants, the mutants typically bind the antagonists with the same or higher affinity than the parent GPCR and typically bind agonists with the same or lower affinity than the parent GPCR.

Mutants that exhibit a significant reduction (typically greater than 2-3 fold) in affinity for the selecting ligand are typically rejected.

Typically, the rank order of binding of a set of ligands of the same class are comparable, although there may be one or two reversals in the order, or there may be an out-lier from the set.

In a further embodiment, two or more ligands that bind simultaneously to the receptor in the same conformation may be used, for example an allosteric modulator and orthosteric agonist.

For the avoidance of doubt, and as is evident from the Examples, it is not necessary to use multiple ligands for the method to be effective.

In a further embodiment, it may be advantageous to select those mutant GPCRs which, while still being able to bind the selected ligand, are not able to bind, or bind less strongly than the parent GPCR, a second selected ligand which is in a different class to the first ligand. Thus, for example, the mutant GPCR may be one that is selected on the basis that it has increased stability with respect to binding a selected antagonist, but the mutant GPCR so selected is further tested to determine whether it binds to a full agonist (or binds less strongly to a full agonist than its parent GPCR). Mutants are selected which do not bind (or have reduced binding of) the full agonist. In this way, further selection is made of a GPCR which is locked into one particular conformation.

It will be appreciated that the selected ligand (with respect to part (b) of the method) and the further (second) ligand as discussed above, may be any pair of ligand classes, for example: antagonist and full agonist; full agonist and antagonist; antagonist and inverse agonist; inverse agonist and antagonist; inverse agonist and full agonist; full agonist and inverse agonist; and so on.

It is preferred that the mutant receptor binds the further (second) ligand with an affinity which is less than 50% of the affinity the parent receptor has for the same further (second) ligand, more preferably less than 10% and still more preferably less than 1% or 0.1% or 0.01% of affinity for the parent receptor. Thus, the $K_d$ for the interaction of the second ligand with mutant receptor is higher than for the parent receptor. As is shown in Example 1, the mutant β-adrenergic receptor βAR-m23 (which was selected by the method of the invention using an antagonist) binds an agonist 3 orders of magnitude more weakly than its parent (ie $K_d$ is 1000× higher). Similarly, in Example 2, the mutant adenosine A2a receptor Rant21 binds agonist 2-4 orders of magnitude more weakly than its parent.

This type of counter selection is useful because it can be used to direct the mutagenesis procedure more specifically (and therefore more rapidly and more efficiently) along a pathway towards a pure conformation as defined by the ligand.

Preferably, the mutant GPCR is provided in a suitable solubilised form in which it maintains structural integrity and is in a functional form (eg is able to bind ligand). An appropriate solubilising system, such as a suitable detergent (or other amphipathic agent) and buffer system is used, which may be chosen by the person skilled in the art to be effective for the particular protein. Typical detergents which may be used include, for example, dodecylmaltoside (DDM) or CHAPS or octylglucoside (OG) or many others. It may be convenient to include other compounds such as cholesterol hemisuccinate or cholesterol itself or heptane-1,2,3-triol. The presence of glycerol or proline or betaine may be useful. It is important that the GPCR, once solubilised from the membrane in which it resides, must be sufficiently stable to be assayed. For some GPCRs, DDM will be sufficient, but glycerol or other polyols may be added to increase stability for assay purposes, if desired. Further stability for assay purposes may be achieved, for example, by solubilising in a mixture of DDM, CHAPS and cholesterol hemisuccinate, optionally in the presence of glycerol. For particularly unstable GPCRs, it may be desirable to solubilise them using digitonin or amphipols or other polymers which can solubilise GPCRs directly from the membrane, in the absence of traditional detergents and maintain stability typically by allowing a significant number of lipids to remain associated with the GPCR. Nanodiscs may also be used for solubilising extremely unstable membrane proteins in a functional form.

Typically, the mutant GPCR is provided in a crude extract (eg of the membrane fraction from the host cell in which it has been expressed, such as *E. coli*). It may be provided in a form in which the mutant protein typically comprises at least 75%, more typically at least 80% or 85% or 90% or 95% or 98% or 99% of the protein present in the sample. Of course, it is typically solubilised as discussed above, and so the mutant GPCR is usually associated with detergent molecules and/or lipid molecules.

A mutant GPCR may be selected which has increased stability to any denaturant or denaturing condition such as to any one or more of heat, a detergent, a chaotropic agent or an extreme of pH.

In relation to an increased stability to heat (ie thermostability), this can readily be determined by measuring ligand binding or by using spectroscopic methods such as fluorescence, CD or light scattering at a particular temperature. Typically, when the GPCR binds to a ligand, the ability of the GPCR to bind that ligand at a particular temperature may be used to determine thermostability of the mutant. It may be convenient to determine a "quasi $T_m$" ie the temperature at which 50% of the receptor is inactivated under stated conditions after incubation for a given period of time (eg 30 minutes). Mutant GPCRs of higher thermostability have an increased quasi Tm compared to their parents.

In relation to an increased stability to a detergent or to a chaotrope, typically the GPCR is incubated for a defined time in the presence of a test detergent or a test chaotropic agent and the stability is determined using, for example, ligand binding or a spectroscopic method as discussed above.

In relation to an extreme of pH, a typical test pH would be chosen (eg in the range 4.5 to 5.5 (low pH) or in the range 8.5 to 9.5 (high pH)).

Because relatively harsh detergents are used during crystallisation procedures, it is preferred that the mutant GPCR is stable in the presence of such detergents. The order of "harshness" of certain detergents is DDM, $C_{11} \rightarrow C_{10} \rightarrow C_9 \rightarrow C_8$ maltoside or glucoside, lauryldimethylamine oxide (LDAO) and SDS. It is particularly preferred if the mutant GPCR is more stable to any of $C_9$ maltoside or glucoside, $C_8$ maltoside or glucoside, LDAO and SDS, and so it is preferred that these detergents are used for stability testing.

Because of its ease of determination, it is preferred that thermostability is determined, and those mutants which have an increased thermostability compared to the parent protein with respect to the selected condition are chosen. It will be appreciated that heat is acting as the denaturant, and this can readily be removed by cooling the sample, for example by placing on ice. It is believed that thermostability may also be a guide to the stability to other denaturants or denaturing conditions. Thus, increased thermostability is likely to translate into stability in denaturing detergents, especially those that are more denaturing than DDM, eg those detergents with a smaller head group and a shorter alkyl chain and/or with a charged head group. We have found that a thermostable GPCR is also more stable towards harsh detergents.

When an extreme of pH is used as the denaturing condition, it will be appreciated that this can be removed quickly by adding a neutralising agent. Similarly, when a chaotrope is used as a denaturant, the denaturing effect can be removed by diluting the sample below the concentration in which the chaotrope exerts its chaotropic effect.

In a particular embodiment of the invention, the GPCR is β-adrenergic receptor (for example from turkey) and the ligand is dihydroalprenolol (DHA), an antagonist.

In a further preferred embodiment of the invention, the GPCR is the adenosine $A_{2a}$ receptor ($A_{2a}R$) (for example, from man) and the ligand is ZM 241385 (4-[2-[[7-amino-2-(2-furyl) [1,2,4]-triazolo [2,3-a][1,3,5]triazin-5-yl]amino] ethyl]phenol), an antagonist or NECA (5'-N-ethylcarboxamido adenosine), an agonist.

In a still further preferred embodiment, the GPCR is the neurotensin receptor (NTR) (for example, from rat) and the ligand is neurotensin, an agonist.

A second aspect of the invention provides a method for preparing a mutant GPCR, the method comprising
(a) carrying out the method of the first aspect of the invention,
(b) identifying the position or positions of the mutated amino acid residue or residues in the mutant GPCR or GPCRs which has been selected for increased stability, and
(c) synthesising a mutant GPCR which contains a mutation at one or more of the positions identified.

As can be seen in the Examples, surprisingly, changes to a single amino acid within the GPCR may increase the stability of the protein compared to the parent protein with respect to a particular condition in which the protein resides in a particular conformation. Thus, in one embodiment of the method of the second aspect of the invention, a single amino acid residue of the parent protein is changed in the mutant protein. Typically, the amino acid residue is changed to the amino acid residue found in the mutant tested in the method of the first aspect of the invention. However, it may be replaced by any other amino acid residue, such as any naturally-occurring amino acid residue (in particular, a "codeable" amino acid residue) or a non-natural amino acid. Generally, for convenience, the amino acid residue is replaced with one of the 19 other codeable amino acids. Preferably, it is the replaced amino acid residue which is present in the mutant selected in the first aspect of the invention.

Also as can be seen in the Examples, a further increase in stability may be obtained by replacing more than one of the amino acids of the parent protein. Typically, each of the amino acids replaced is one which has been identified using the method of the first aspect of the invention. Typically, each amino acid identified is replaced by the amino acid present in the mutant protein although, as noted above, it may be replaced with any other amino acid.

Typically, the mutant GPCR contains, compared to the parent protein, from 1 to 10 replaced amino acids, preferably from 1 to 8, typically from 2 to 6 such as 2, 3, 4, 5 or 6 replaced amino acids.

It will be appreciated that the multiple mutants may be subject to the selection method of the first aspect of the invention. In other words, multiple mutants may be provided in step (a) of the method of the first aspect of the invention. It will be appreciated that by the first and/or second aspect of the invention multiply mutagenised GPCRs may be made, whose conformation has been selected to create a very stable multiple point mutant protein.

The mutant GPCRs may be prepared by any suitable method. Conveniently, the mutant protein is encoded by a suitable nucleic acid molecule and expressed in a suitable host cell. Suitable nucleic acid molecules encoding the mutant GPCR may be made using standard cloning techniques, site-directed mutagenesis and PCR as is well known in the art. Suitable expression systems include constitutive or inducible expression systems in bacteria or yeasts, virus expression systems such as baculovirus, semliki forest virus and lentiviruses, or transient transfection in insect or mammalian cells. Suitable host cells include E. coli, Lactococcus lactis, Saccharomyces cerevisiae, Schizosaccharomyces pombe, Pichia pastoris, Spodoptera frugiperda and Trichoplusiani cells. Suitable animal host cells include HEK 293, COS, S2, CHO, NSO, DT40 and so on. It is known that some GPCRs require specific lipids (eg cholesterol) to function. In that case, it is desirable to select a host cell which contains the lipid. Additionally or alternatively the lipid may be added during isolation and purification of the mutant protein. It will be appreciated that these expression systems and host cells may also be used in the provision of the mutant GPCR in part (a) of the method of the first aspect of the invention.

Molecular biological methods for cloning and engineering genes and cDNAs, for mutating DNA, and for expressing polypeptides from polynucleotides in host cells are well known in the art, as exemplified in "Molecular cloning, a laboratory manual", third edition, Sambrook, J. & Russell, D. W. (eds), Cold Spring Harbor Laboratory Press, Cold Spring Harbor, N.Y., incorporated herein by reference.

In a further embodiment of the first or second aspect of the invention it is determined whether the selected or prepared mutant GPCR is able to couple to a G protein. It is also preferred if it is determined whether the selected or prepared mutant GPCR is able to bind a plurality of ligands of the same class as the selecting ligand with a comparable spread and/or rank order of affinity as the parent GPCR.

A third aspect of the invention provides a mutant GPCR prepared by the method of the second aspect of the invention.

The invention includes mutant GPCRs with increased stability compared to their parent GPCRs, particularly those with increased thermostability.

Mutant β-adrenergic Receptor

β-adrenergic receptors are well known in the art. They share sequence homology to each other and bind to adrenalin.

A fourth aspect of the invention provides a mutant β-adrenergic receptor which, when compared to the corresponding wild-type β-adrenergic receptor, has a different amino acid at a position which corresponds to any one or more of the following positions according to the numbering of the turkey β-adrenergic receptor as set out in FIG. 9: Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338.

The mutant β-adrenergic receptor may be a mutant of any β-adrenergic receptor provided that it is mutated at one or more of the amino acid positions as stated by reference to the given turkey β-adrenergic receptor amino acid sequence.

It is particularly preferred if the mutant GPCR is one which has at least 20% amino acid sequence identity when compared to the given turkey β-adrenergic receptor sequence, as determined using MacVector and CLUSTALW (Thompson et al (1994) *Nucl. Acids Res.* 22, 4673-4680). More preferably, the mutant receptor has at least 30% or at least 40% or at least 50% amino acid sequence identity. There is generally a higher degree of amino acid sequence identity which is conserved around the orthosteric ("active") site to which the natural ligand binds.

As is described in Example 1 and FIG. 1 below, individual replacement of the following amino acid residues in the parent turkey β-adrenergic sequence (as shown in FIG. 9) lead to an increase in thermostability: Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338.

Thus, the invention includes mutant turkey β-adrenergic receptors in which, compared to its parent, one or more of these amino acid residues have been replaced by another amino acid residue. The invention also includes mutant β-adrenergic receptors from other sources in which one or more corresponding amino acids in the parent receptor are replaced by another amino acid residue. For the avoidance of doubt, the parent may be a β-adrenergic receptor which has a naturally-occurring sequence, or it may be a truncated form or it may be a fusion, either to the naturally occurring protein or to a fragment thereof, or it may contain mutations compared to the naturally-occurring sequenced provided that it retains ligand-binding ability.

By "corresponding amino acid residue" we include the meaning of the amino acid residue in another β-adrenergic receptor which aligns to the given amino acid residue in turkey β-adrenergic receptor when the turkey β-adrenergic receptor and the other β-adrenergic receptor are compared using MacVector and CLUSTALW.

FIG. 9 shows an alignment between turkey β-adrenergic receptor and human β1, β2 and β3 β-adrenergic receptors.

It can be seen that Ile 72 of human β1 corresponds to Ile 55 of turkey β-adrenergic receptor; Ile 47 of human β2 corresponds to Ile 55 of turkey β-adrenergic receptor; and Thr51 of human β corresponds to Ile 55 of turkey β-adrenergic receptor. Other corresponding amino acid residues in human β1, β2 and β3 can readily be identified by reference to FIG. 9.

It is preferred that the particular amino acid is replaced with an Ala. However, when the particular amino acid residue is an Ala, it is preferred that it is replaced with a Leu (for example, see turkey β-adrenergic Ala 234, Ala 282 and Ala 334 in FIG. 1).

It is preferred if the mutant β-adrenergic receptor has a different amino acid compared to its parent at more than one amino acid position since this is likely to give greater stability. Particularly preferred human β1 receptor mutants are those in which one or more of the following amino acid residues are replaced with another amino acid residue: K85, M107, Y244, A316, F361 and F372. Typically, the given amino acid residue is replaced with Ala or Val or Met or Leu or Ile (unless they are already that residue).

Mutant human β1 receptors which have combinations of 3 or 4 or 5 or 6 mutations as described above are prepared.

Particularly preferred human β2 receptor mutants are those in which one or more of the following amino acids are replaced with another amino acid residue: K60, M82, Y219, C265, L310 and F321. Typically, the given amino acid residue is replaced with Ala or Val or Met or Leu or Ile (unless they are already that residue).

Mutant human β2 receptors which have combinations of 3 or 4 or 5 or 6 mutations as described above are preferred.

Figure 26:
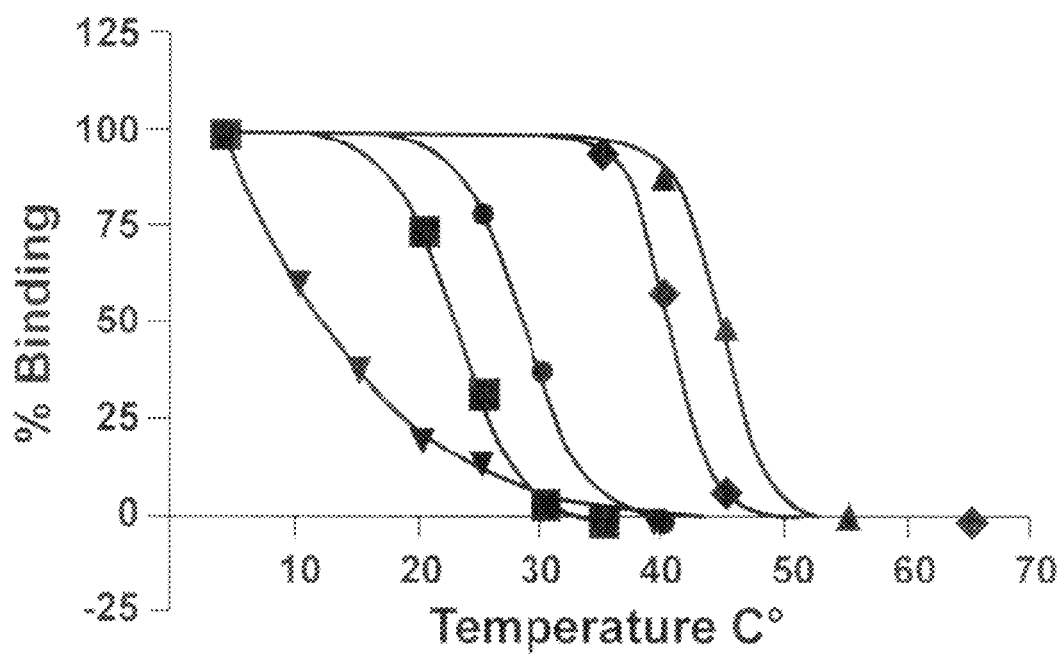

FIG. 26 shows the effect on thermostability when six thermostabilising mutations in β1-m23 (R68S, M90V, Y227A, A282L, F327A, F338M) were transferred directly to the human β2 receptor (equivalent mutations K60S, M82V, Y219A, C265L, L310A, F321M), making human β2-m23. The Tms for human β2 and β2-m23 were 29° C. and 41° C. respectively, thus exemplifying the transferability of thermostabilising mutations from one receptor to another receptor. Accordingly, a particularly preferred human β2 receptor mutant is one which comprises the mutations K60S, M82V, Y219A, C265L, L310A, F321M.

Particularly preferred human β3 receptor mutants are those in which one or more of the following amino acids are replaced with another amino acid residue: W64, M86, Y224, P284, A330 and F341. Typically, the given amino acid residue is replaced with Ala or Val or Met or Leu or Ile (unless they are already that residue).

Mutant human β3 receptors which have combinations of 3 or 4 or 5 or 6 mutations as described above are preferred.

Particularly preferred combinations of mutations are described in detail in Tables 1 and 2 in Example 1, and the invention includes the mutant turkey β-adrenergic receptors, and also includes mutant β-adrenergic receptors where amino acids in corresponding position have been replaced by another amino acid, typically the same amino acid as indicated in Tables 1 and 2 in Example 1.

Particularly preferred mutants are those which contain mutations in the amino acids which correspond to the given amino acid residue by reference to turkey β-adrenergic receptor: (R68S, Y227A, A282L, A334L) (see m6-10 in Table 2 below); (M90V, Y227A, F338M) (see m7-7 in Table 2 below); (R68S, M90V, V230A, F327A, A334L) (see m10-8 in Table 2 below); and (R68S, M90V, Y227A, A282L, F327A, F338M) (see m23 in Table 2 below).

Mutant Adenosine Receptor

Adenosine receptors are well known in the art. They share sequence homology to each other and bind to adenosine.

A fifth aspect of the invention provides a mutant adenosine receptor which, when compared to the corresponding wild-type adenosine, has a different amino acid at a position which corresponds to any one or more of the following positions according to the numbering of the human adenosine $A_{2a}$ receptor as set out in FIG. 10: Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315, Ala 54, Val 57, His 75, Thr 88, Gly 114, Gly 118, Thr 119, Lys 122, Gly 123, Pro 149, Glu 151, Gly 152, Ala 203, Ala 204, Ala 231, Leu 235, Val 239.

The mutant adenosine receptor may be a mutant of any adenosine receptor provided that it is mutated at one or more of the amino acid positions as stated by reference to the given human adenosine $A_{2a}$ receptor amino acid sequence.

It is particularly preferred if the mutant GPCR is one which has at least 20% amino acid sequence identity when compared to the given human adenosine $A_{2a}$ receptor sequence, as determined using MacVector and CLUSTALW. Preferably, the mutant GPCR has at least 30% or at least 40% or at least 50% or at least 60% sequence identity. Typically, there is a higher degree of sequence conservation at the adenosine binding site.

As is described in Example 2 below, individual replacement of the following amino acid residues in the human adenosine $A_{2a}$ receptor sequence (as shown in FIG. 10) lead to an increase in thermostability when measured with the agonist 5'-N-ethylcarboxamidoadenosine (NECA):

Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315.

Replacement of the following amino acid residues in the human $A_{2a}$ receptor sequence (as shown in FIG. 10) lead to an increase in thermostability when measured with the antagonist ZM 241385 (4-[2-[[7-amino-2-(2-furyl) [1,2,4]-triazolo[2,3-α][1,3,5[triazin-5-yl]amino]ethyl]phenol):

Ala 54, Val 57, His 75, Thr 88, Gly 114, Gly 118, Thr 119, Lys 122, Gly 123, Pro 149, Glu 151, Gly 152, Ala 203, Ala 204, Ala 231, Leu 235, Val 239.

Thus, the invention includes mutant human adenosine $A_{2a}$ receptors in which, compared to its parent, one or more of these amino acid residues have been replaced by another amino acid residue. The invention also includes mutant adenosine receptors from other sources in which one or more corresponding amino acids in the parent receptor are replaced by another amino acid residue. For the avoidance of doubt, the parent may be an adenosine receptor which has a naturally-occurring sequence, or it may be a truncated form or it may be a fusion, either to the naturally-occurring protein or to a fragment thereof, or it may contain mutations compared to the naturally-occurring sequence, provided that it retains ligand-binding ability.

By "corresponding amino acid residue" we include the meaning of the amino acid residue in another adenosine receptor which aligns to the given amino acid residue in human adenosine $A_{2a}$ receptor when the human adenosine $A_{2a}$ receptor and the other adenosine receptor are compared using MacVector and CLUSTALW.

FIG. 10 shows an alignment between human adenosine $A_{2a}$ receptor and three other human adenosine receptors (A2b, A3 and A1).

It can be seen that, for example, Ser 115 in the $A_{2b}$ receptor (indicated as AA2BR) corresponds to Gly 114 in the $A_{2a}$ receptor. Similarly, it can be seen that Ala 60 in the $A_3$ receptor (indicated as AA3R) corresponds to Ala 54 in the $A_{2a}$ receptor, and so on. Other corresponding amino acid residues in human adenosine receptors $A_{2b}$, $A_3$ and $A_1$ can readily be identified by reference to FIG. 10.

It is preferred that the particular amino acid in the parent is replaced with an Ala. However, when the particular amino acid residue in the parent is an Ala, it is preferred that it is replaced with a Leu.

It is preferred that the mutant adenosine receptor has a different amino acid compared to its parent at more than one amino acid position. Particularly preferred human adenosine A2b receptors are those in which one or more of the following amino acid residues are replaced with another amino acid residue: A55, T89, R123, L236 and V240. Typically, the given amino acid residue is replaced with Ala or Val or Met or Leu or Ile (unless they are already that residue).

Mutant human adenosine A2b receptors which have combinations of 3 or 4 or 5 mutations as described above are preferred.

Particularly preferred human adenosine A3 receptors are those in which one or more of the following amino acid residues are replaced with another amino acid residue: A60, T94, W128, L232 and L236. Typically, the given amino acid residue is replaced with Ala or Val or Met or Leu or Ile (unless they are already that residue).

Mutant human adenosine A3 receptors which have combinations of 3 or 4 or 5 mutations as described above are preferred.

Particular preferred human adenosine A1 receptors are those in which one or more of the following residues are replaced: A57, T91, A125, L236, and L240. Typically, the given amino acid residue is replaced with Ala or Val or Met or Leu or Ile (unless they are already that residue).

Particularly preferred combinations of mutations are described in detail in Example 2. The invention includes these mutant human adenosine $A_{2a}$ receptors, and also includes other mutant adenosine receptors where amino acids in corresponding positions have been replaced by another amino acid, typically the same amino acid as indicated in Example 2.

Particularly preferred adenosine receptor mutants are those which contain mutations in the amino acids which correspond to the given amino residue by reference to human adenosine A2a receptor: (A54L, K122A, L235A) (Rant 17); (A54L, T88A, V239A, A204L) (Rant 19); and (A54L, T88A, V239A, K122A) (Rant 21).

Mutant Neurotensin Receptor

Neurotensin receptors are known in the art. They share sequence homology and bind neurotensin.

A sixth aspect of the invention provides a mutant neurotensin receptor which, when compared to the corresponding wild-type neurotensin receptor, has a different amino acid at a position which corresponds to any one or more of the following positions according to the numbering of the rat neurotensin receptor as set out in FIG. 11: Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399.

It is particularly preferred if the mutant GPCR is one which has at least 20% amino acid sequence identity when compared to the given rat neurotensin receptor sequence, as determined using Mac Vector and CLUSTALW. Preferably, the mutant GPCR has at least 30% or at least 40% or at least 50% amino acid sequence identity.

The mutant neurotensin receptor may be a mutant of any neurotensin receptor provided that it is mutated at one or more of the amino acid positions as stated by reference to the given rat neurotensin receptor amino acid sequence.

As is described in Example 3 below, individual replacement of the following amino acid residues in the rat neurotensin receptor sequence (as shown in FIGS. 11 and 28) lead to an increase in thermostability when considered with respect to the absence of neurotensin. Leu 72, Ala 86, Ala 90, Ser 100, His 103, Ser 108, Leu 109, Leu 111, Asp 113, Ile 116, Ala 120, Asp 139, Phe 147, Ala 155, Lys 176, Thr 179, Met 181, Ser 182, Phe 189, Leu 205, Thr 207, Gly 209, Gly 215, Leu 256, Asn 262, Val 268, Met 293, Asp 345, Tyr 349, Tyr 351, Ala 356, Phe 358, Ser 362, Ala 385, Cys 386, Trp 391, Arg 392, His 393, Lys 397, Pro 399.

As is described in Example 3 below, individual replacement of the following amino acid residues in the rat neurotensin receptor sequence (as shown in FIGS. 11 and 28) lead to an increase in thermostability when considered with respect to the presence of neurotensin. Ala 69, Ala 73, Ala 86, Ala 90, His 103, Val 165, Glu 166, Ala 177, Arg 183, Gly 215, Val 229, Met 250, Ile 253, Ile 260, Thr 279, Thr 294, Gly 306, Leu 308, Val 309, Leu 310, Val 313, Phe 342, Phe 358, Val 360, Ser 362, Asn 370, Ser 373, Phe 380, Ala 385, Pro 389, Gly 390, Arg 395.

Thus, the invention includes mutant rat neurotensin receptor in which, compared to its parent, one or more of these amino acid residues have been replaced by another amino acid residue. The invention also includes mutant neurotensin receptors from other sources in which one or more corresponding amino acids in the parent receptor are replaced by another amino acid residue. For the avoidance of doubt the parent may be a neurotensin receptor which has a naturally-occurring sequence, or it may be a truncated form or it may be a fusion, either to the naturally-occurring protein or to a fragment thereof, or it may contain mutations compared to the naturally-occurring sequence, providing that it retains ligand-binding ability.

By "corresponding amino acid residue" we include the meaning of the amino acid residue in another neurotensin receptor which aligns to the given amino acid residue in rat neurotensin receptor when the rat neurotensin receptor and the other neurotensin receptor are compared using MacVector and CLUSTALW.

FIG. 11 shows an alignment between rat neurotensin receptor and two human neurotensin receptors 1 and 2. It can be seen, for example, that Ala 85 of the human neurotensin receptor 1 corresponds to Ala 86 of the rat neurotensin receptor, that Phe 353 of the human neurotensin receptor 1 corresponds to Phe 358 of the rat neurotensin receptor, and so on. Other corresponding amino acid residue in the human neurotensin receptors 1 and 2 can readily be identified by reference to FIG. 11.

It is preferred that the particular amino acid in the parent is replaced with an Ala. However, when the particular amino acid residue in the parent is an Ala, it is preferred that it is replaced with a Leu.

It is preferred that the mutant neurotensin receptor has a different amino acid compared to its parent at more than one amino acid position. Particularly preferred human neurotensin receptors (NTR1) are those in which one or more of the following amino acid residues are replaced with another amino acid residue: Ala 85, His 102, Ile 259, Phe 337 and Phe 353. Typically, the given amino acid residues is replaced with Ala or Val or Met or Leu or Ile (unless they are already that residue).

Mutant human neurotensin receptors (NTR1) which have combinations of 3 or 4 or 5 mutations as described above are preferred.

Particularly preferred human neurotensin receptors (NTR2) are those in which one or more of the following amino acid residues are replaced with another amino acid residue: V54, R69, T229, P331 and F347. Typically, the given amino acid residue is replaced with Ala or Val or Met or Leu or Ile (unless they are already that residue). Mutant human neurotensin receptors (NTR2) which have combinations of 3 or 4 or 5 mutations as described above are preferred.

Particularly preferred combinations of mutations are described in detail in Example 3. The invention includes these mutant rat neurotensin receptors, and also includes other mutant neurotensin receptors where amino acids in corresponding positions have been replaced by another amino acid, typically the same amino acid as indicated in Example 3.

Particularly preferred neurotensin receptor mutants are those which contain mutations in the amino acid residues which correspond to the given amino acid residue by reference to the rat neurotensin receptor: (F358A, A86L, I260A, F342A) (Nag7m); (F358A, H103A, I260A, F342A) (Nag7n).

Mutant Muscarinic Receptor

Muscarinic receptors are known in the art. They share sequence homology and bind muscarine.

A seventh aspect of the invention provides a mutant muscarinic receptor which, when compared to the corresponding wild-type muscarinic receptor, has a different amino acid at a position which corresponds to any one or more of the following positions according to the numbering of the human muscarinic receptor M1 as set out in FIG. 17: Leu 65, Met 145, Leu 399, Ile 383 and Met 384.

It is particularly preferred if the mutant GPCR is one which has at least 20% amino acid sequence identity when compared to the given human muscarinic receptor sequence, as determined using MacVector and CLUSTALW. Preferably, the mutant GPCR has at least 30% or at least 40% or at least 50% amino acid sequence identity.

The mutant muscarinic receptor may be a mutant of any muscarinic receptor provided that it is mutated at one or more of the amino acid positions as stated by reference to the given muscarinic receptor amino acid sequence.

Thus, the invention includes a mutant human muscarinic receptor in which, compared to its parent, one or more of these amino acid residues have been replaced by another amino acid residue. The invention also includes mutant muscarinic receptors from other sources in which one or more corresponding amino acids in the parent receptor are replaced by another amino acid residue. For the avoidance of doubt the parent may be a muscarinic receptor which has a naturally-occurring sequence, or it may be a truncated form or it may be a fusion, either to the naturally-occurring protein or to a fragment thereof, or it may contain mutations compared to the naturally-occurring sequence, providing that it retains ligand-binding ability.

By "corresponding amino acid residue" we include the meaning of the amino acid residue in another muscarinic receptor which aligns to the given amino acid residue in human muscarinic receptor when the human muscarinic receptor and the other muscarinic receptor are compared using MacVector and CLUSTALW.

It is preferred that the particular amino acid is replaced with an Ala. However, when the particular amino acid residue is an Ala, it is preferred that it is replaced with a Leu.

As shown in Examples 1-3 and described above, we have identified thermostabilising mutations scattered widely throughout the sequences of the turkey beta1 adrenergic receptor, human adenosine receptor, rat neurotensin receptor and human muscarinic receptor. FIG. 17 provides an alignment of these sequences with the sequence of the human beta-2AR such that when the thermostabilising mutations are positioned onto the sequences then, in 11 instances out of a total of 70, two sequences contain mutations at the same position (denoted in FIG. 17 with a star). Thus it will be appreciated that once one or more stabilising mutations have been identified in one GPCR, a further GPCR with increased stability can be generated by aligning the amino acid sequences of the GPCRs and making the same one or more mutations at the corresponding position or positions. This concept is clearly exemplified in FIG. 26 wherein the six thermostabilising mutations in turkey β1-m23 were transferred directly to the human β2 receptor. The resultant mutant, β2-m23, had a Tm 12° C. higher than that of the human β2 receptor.

Accordingly, an eighth aspect of the invention provides a method for producing a mutant GPCR with increased stability relative to its parent GPCR, the method comprising:
  (i) identifying in the amino acid sequence of one or more mutants of a first parent GPCR with increased stability relative to the first parent GPCR, the position or positions at which the one or more mutants have at least one different amino acid residue compared to the first parent GPCR, and
  (ii) making one or more mutations in the amino acid sequence that defines a second GPCR at the corresponding position or positions, to provide one or more mutants of a second parent GPCR with increased stability relative to the second parent GPCR.

The one or more mutants of a first parent GPCR may be selected or prepared according to the methods of the first or second aspects of the invention. Accordingly, it will be appreciated that the one or more mutants of a first parent GPCR may be any of the mutants of the third, fourth, fifth, sixth or seventh aspects of the invention. Hence, the method of the eighth aspect of the invention may be used to create stable, conformationally locked GPCRs by mutagenesis. For example, following the selection of mutant GPCRs which have increased stability in a particular conformation, the stabilising mutation can be identified and the amino acid at a corresponding position in a second GPCR replaced to produce a mutant GPCR with increased stability in a particular conformation relative to a second parent GPCR.

For the avoidance of doubt the first parent GPCR may be a GPCR which has a naturally-occurring sequence, or it may be a truncated form or it may be a fusion, either to the naturally-occurring protein or to a fragment thereof, or it may contain mutations compared to the naturally-occurring sequence, providing that it retains ligand-binding ability.

Typically, identifying the position or positions at which the one or more mutants have at least one different amino acid residue compared to the first parent GPCR involves aligning their amino acid sequences with that of the parent GPCR, for example using the Clustal W program (Thompson et al., 1994).

By "corresponding position or positions", we include the meaning of the position in the amino acid sequence of a second GPCR which aligns to the position in the amino acid sequence of the first GPCR, when the first and second GPCRs are compared by alignment, for example by using MacVector and Clustal W. For example, as shown in the alignment in FIG. 17, the six stabilising mutations in turkey β1-m23, R68S, M90V, Y227A, A282L, F327A and F338M, are at positions which correspond to residues K60, M82, Y219, C265, L310 and F321 respectively in the human β2 receptor.

Having identified the corresponding position or positions in the amino acid sequence of a second GPCR, the amino acids at those positions are replaced with another amino acid. Typically, the amino acids are replaced with the same amino acids which replaced the amino acids at the corresponding positions in the mutant of the first parent GPCR (unless they are already that residue). For example, at position 68 in turkey β1-m23 (R68S), an arginine residue was replaced with a serine residue. Therefore, at the corresponding position in the human β2 receptor, position 60 (K60), the lysine residue is preferably replaced with a serine residue.

Mutations can be made in an amino acid sequence, for example, as described above and using techniques well-established in the art.

It will be appreciated that the second GPCR may be any other GPCR. For example, stabilising mutations in a GPCR from one species may be transferred to a second GPCR from another species. Similarly, stabilising mutations in one particular GPCR isoform may be transferred to a second GPCR which is a different isoform. Preferably, the second parent GPCR is of the same GPCR class or family as the first parent GPCR. Phylogenetic analyses have divided GPCRs into three main classes based on protein sequence similarity, i.e., classes 1, 2, and 3 whose prototypes are rhodopsin, the secretin receptor, and the metabotropic glutamate receptors, respectively (Foord et al (2005) *Pharmacol. Rev.* 57, 279-288). Thus, the second GPCR may be a GPCR which is of the same GPCR class as the first parent GPCR. Similarly, GPCRs have been divided into families by reference to natural ligands such as glutamate and GABA. Thus, the second GPCR may be of the same GPCR family as the first parent GPCR. A list of GPCR classes and families has been produced by the International Union of Pharmacology (Foord et al (2005) *Pharmacol. Rev.* 57, 279-288) and this list is periodically updated at www.iuphar-db.org/GPCR/ReceptorFamiliesForward.

It will be appreciated that the second parent GPCR must be able to be aligned with the first parent GPCR such that the corresponding positions of the mutations in the first GPCR can be determined in the second GPCR. Thus typically, the second parent GPCR has at least 20% sequence identity to the first parent GPCR and more preferably at least 30%, 40%, 50%, 60%, 70%, 80% or 90% sequence identity to the first parent GPCR. However, some GPCRs have low sequence identity (e.g. family B and C GPCRs) and at the same time are very similar in structure. Thus the 20% sequence identity threshold is not absolute.

The inventors have reasoned that the identification of structural motifs in which the one or more mutations in a mutant GPCR with increased stability reside, will be useful in producing further mutant GPCRs with increased stability.

Accordingly, a ninth aspect of the invention provides a method for producing a mutant G-protein coupled receptor (GPCR) with increased stability relative to its parent GPCR, the method comprising:

(i) providing one or more mutants of a first parent GPCR with increased stability relative to the first parent GPCR (ii) identifying in a structural membrane protein model the structural motif or motifs in which the one or more mutants have at least one different amino acid residue compared to the first parent GPCR, and (iii) making one or more mutations in the amino acid sequence that defines a corresponding structural motif or motifs in a second parent GPCR, to provide one or more mutants of a second parent GPCR with increased stability relative to the second parent GPCR.

Mapping stabilising mutations onto one or more known structural models can be used to identify particular structural motifs in which such stabilising mutations reside. We have mapped stabilising mutations of the β1-adrenergic receptor onto structural models of the β2-adrenergic receptor (Rasmussen et al (2007) *Nature* 450, 383-387; Cherezov et al (2007) *Science* 318:1258-65; Rosenbaum et al (2007) *Science* 318:1266-1273) in order to identify such motifs. For example, Table (vi) lists the turkey β1-adrenergic receptor mutations which we have mapped onto the human β2-adrenergic receptor and describes the corresponding structural motifs in which they reside. As discussed in Example 4, mapping of the Y227A mutation (equivalent to Y219 in the human $β_2$ receptor) onto the human $β_2$-adrenergic receptor reveals its position at the interface between helices such that the mutation may improve packing at the helical interface (see FIGS. 15, 16 and 23). Similarly, mapping of the M90V mutation (equivalent to M82 in the human $β_2$ receptor) onto the human $β_2$-adrenergic receptor reveals it to be in helix 2 at a point where the helix is kinked (see FIGS. 15, 16 and 20). Other mutations were found to reside in further structural motifs including transmembrane helix surfaces pointing into the lipid bilayer, hydrophobic-hydrophilic boundary regions, protein binding pockets and loop regions (see Table (vi) and FIGS. 18-19, 21-22 and 24-25).

Such structural motifs, by virtue of them containing stabilising mutations, are important in determining protein stability. Therefore, targeting mutations to these motifs will facilitate the generation of stabilised mutant GPCRs. Indeed, there were several instances where more than one mutation mapped to the same structural motif. For example, the Y227A, V230A and A234L mutations in the turkey β1 adrenergic receptor mapped to the same helical interface, the V89L and M90V mutations mapped to the same helical kink and the F327A and A334L mutations mapped to the same helical surface pointing towards the lipid bilayer (Table (vi)). Thus, when one stabilising mutation has been identified, the determination of the structural motif in which that mutation is located will enable the identification of further stabilising mutations.

In an embodiment of the ninth aspect of the invention, the one or more mutants of a first parent GPCR are selected or prepared according to the methods of the first, second or eighth aspects of the invention. Accordingly, it will be appreciated that the one or more mutants of a first parent GPCR may be any of the mutants of the third, fourth, fifth, sixth or seventh aspects of the invention. Hence, the method of the ninth aspect of the invention may also be used to create stable, conformationally locked GPCRs by mutagenesis. For example, following the selection of mutant GPCRs which have increased stability in a particular conformation, the structural motifs in which such stabilising mutations reside can be identified. Making one or more mutations in the amino acid sequence that defines the corresponding structural motif in another GPCR can then be used to produce a mutant GPCR with increased stability in a particular conformation relative to its parent GPCR.

We have performed a multiple sequence alignment of the human beta-2AR, rat NTR1, turkey beta-1 AR, human Adenosine A2aR and human muscarinic M1 receptor amino acid sequences (FIG. 17) which shows that, when the thermostabilising mutations identified (see Examples 1-3) are positioned on the sequences then, in 11 instances out of a total of 70, two sequences contain mutations at the same position (denoted in FIG. 17 with a star). Without wishing to be bound by any theory, the inventors believe that thermostabilising mutations at these positions should be of enhanced transferability for mapping onto a structural membrane protein model. Thus in one embodiment, the mutant of the first parent GPCR is a mutant human beta-2AR, rat NTR1, turkey beta-1 AR, human Adenosine A2aR or human muscarinic M1 receptor which, when compared to its corresponding parent receptor, has a different amino acid at a position which corresponds to any one or more of the following positions according to the numbering of the human beta2 AR as set out in FIG. 17: Ala 59, Val 81, Ser 143, Lys 147, Val 152, Glu 180, Val 222, Ala 226, Ala 271, Leu 275 and Val 317.

In order to identify the structural motif or motifs, the stabilising mutations are mapped onto a known structure of a membrane protein.

By "membrane protein" we mean a protein that is attached to or associated with a membrane of a cell or organelle. Preferably, the membrane protein is an integral membrane protein that is permanently integrated into the membrane and can only be removed using detergents, non-polar solvents or denaturing agents that physically disrupt the lipid bilayer.

The structural model of a membrane protein may be any suitable structural model. For example, the model may be a known crystal structure. Examples of GPCR crystal structures include bovine rhodopsin (Palczewski, K. et al., Science 289, 739-745. (2000)) and human $β_2$ adrenergic receptor (Rasmussen et al, Nature 450, 383-7 (2007); Cherezov et al (2007) *Science* 318:1258-65; Rosenbaum et al (2007) *Science* 318:1266-1273). The coordinates for the human $\beta_2$ adrenergic receptor structure can be found in the RCSB Protein Data Bank under accession codes: 2rh1, 2r4r and 2r4s. Alternatively, the structural model may be a computer generated model based upon homology or using de novo structure prediction methods (Qian et al *Nature* (2007) 450: 259-64).

It will be appreciated that stabilising mutations of a given mutant GPCR can be mapped onto a structural model of any membrane protein which has sufficient structural similarity to the GPCR. In particular, the domain of the membrane protein must have sufficient structural similarity to the GPCR domain in which the stabilising mutation resides, for a given mutation to be transferable.

A protein domain is typically defined as a discretely folded assembly of secondary structure elements which may stand alone as a single protein or be part of a larger protein in combination with other domains. It is commonly a functional evolutionary unit.

GPCRs are essentially single domain proteins excluding those with large N-terminal domains. Therefore, typically, the structural model is of a membrane protein which comprises at least one domain that has sufficient structural similarity to the GPCR.

Structural similarity can be determined indirectly by the analysis of sequence identity, or directly by comparison of structures.

With regard to sequence identity, the amino acid sequence encoding the GPCR domain in which the mutant has at least one different amino acid residue compared to the first parent GPCR, is aligned with an amino acid sequence encoding a domain of a membrane protein for which a structural model is available. It will be appreciated that one or more of these sequences may contain an inserted sequence or N-terminal or C-terminal extensions which are additional to the core conserved domain. For optimal alignment, such sequences are removed so as not to skew the analysis. Membrane proteins with sufficient sequence identity across the domain in question may then be used as the structural model for mapping mutations. It has been shown for soluble protein domains that their 3D structure is broadly conserved above 20% sequence identity and well conserved above 30% identity, with the level of structural conservation increasing as sequence identity increases up to 100% (Ginalski, K. Curr Op Struc Biol (2006) 16, 172-177). Thus, it is preferred if the structural membrane protein model is a model of a membrane protein which contains a domain that shares at least 20% sequence identity with the mutant GPCR domain containing the at least one different amino acid residue compared to the first parent GPCR, and more preferably at least 30%, 40%, 50%, 60%, 70%, 80% or 90% sequence identity, and yet more preferably at least 95% or 99% sequence identity.

Sequence identity may be measured by the use of algorithms such as BLAST or PSI-BLAST (Altschul et al, NAR (1997), 25, 3389-3402) or methods based on Hidden Markov Models (Eddy S et al, J Comput Biol (1995) Spring 2 (1) 9-23). Typically, the percent sequence identity between two polypeptides may be determined using any suitable computer program, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., 1994). The parameters used may be as follows: Fast pairwise alignment parameters: K-tuple (word) size; 1, window size; 5, gap penalty; 3, number of top diagonals; 5. Scoring method: x percent. Multiple alignment parameters: gap open penalty; 10, gap extension penalty; 0.05. Scoring matrix: BLOSUM.

In addition to sequence identity, structural similarity can be determined directly by comparison of structural models. Structural models may be used to detect regions of structural similarity not evident from sequence analysis alone, and which may or may not be contiguous in the sequence. For example, family B and C GPCRs are thought to share similar structures; however, their sequence identity is very low. Similarly, the water transporting aquaporins spinach SoPip2, *E. coli* AqpZ, *Methanococcus* AqpM, rat Aqp4, human Aqp1 and sheep Aqp0 share low sequence identity but all have similar structures.

Structural models of high fidelity may be constructed for proteins of unknown structure using standard software packages such as MODELLER (Sali A and Blundell T, J Mol Biol (1993) 234(3) 779-815), wherein the structure is modelled on a known structure of a homologous protein. Such modelling improves with increasing sequence identity. Typically, the sequence identity between the sequence of unknown structure and a sequence of known 3D structure is more than 30% (Ginalski, K. Curr Op Struc Biol (2006) 16, 172-177). In addition, de novo structure prediction methods based on sequence alone may be used to model proteins of unknown structure (Qian et al, (2007) Nature 450:259-64). Once structures have been experimentally determined or derived by modelling, regions of structural similarity may be detected by direct comparison of two or more 3D structures. They may, for example, comprise secondary structure elements of a particular architecture and topology which can be detected by the use of software such as DALI (Holm, L and Sander, C (1996) Science 273, 595-603). They may comprise local arrangements of amino acid side chains and the polypeptide backbone, or specific sets of atoms or groups of atoms in a particular spatial arrangement, which may for example also be detected by the use of graph theoretical representations (Artymiuk,P et al, (2005) J Amer Soc Info Sci Tech 56 (5) 518-528). In this approach, the atoms or groups of atoms within the proteins or regions of proteins to be compared are typically represented as the nodes of a graph, with the edges of the graph describing the angles and distances between the nodes. Common patterns in these graphs indicate common structural motifs. This approach may be extended to include any descriptor of atoms or groups of atoms, such as hydrogen bond donor or acceptor, hydrophobicity, shape, charge or aromaticity; for example proteins may be spatially mapped according to such descriptors using GRID and this representation used as a basis for similarity searching (Baroni et al (2007) J Chem Inf Mod 47, 279-294). Descriptions of the methods, availability of software, and guidelines for user-defined selection of parameters, thresholds and tolerances are described in the references given above.

In a preferred embodiment, the structural membrane protein model is a structural GPCR model. It will be appreciated that the structural model of a GPCR may be a model of the first parent GPCR. For example, stabilising mutations within a mutant GPCR having increased stability can be directly mapped onto the first parent GPCR structure and the structural motifs in which such mutations are located, identified. Where the structure of the first parent GPCR is unknown, structural models of other GPCRs may be used. For example, stabilising mutations in a GPCR from one species may be mapped onto a known structural model of the same GPCR from another species. Similarly, stabilising mutations in one particular GPCR isoform may be mapped onto a known structural model of another GPCR isoform. Moreover, stabilising mutations from one GPCR may be mapped onto a GPCR of the same class or family. A list of GPCR classes and families has been produced by the International Union of Pharmacology (Foord et al (2005) *Pharmacol. Rev.* 57, 279-288) and this list is periodically updated at www.i-uphar-db.org/GPCR/ReceptorFamiliesForward.

As described above, it will be appreciated that the structural model may be of any GPCR provided it has sufficient structural similarity across the domain in which the mutant GPCR has at least one different amino acid compared to the first parent GPCR. Thus, it is preferred if the GPCR shares at least 20% sequence identity with the mutant of the first parent GPCR across the protein domain containing the at least one different amino acid residue compared to the first parent GPCR, and more preferably at least 30%, 40%, 50%, 60%, 70%, 80% or 90% sequence identity, and yet more preferably at least 95% or 99% sequence identity. However, the inventors recognise that the 20% sequence identity threshold is not absolute. GPCRs with less than 20% sequence identity to the first parent GPCR may also serve as a structural model to which stabilising mutations are transferred, wherein the low sequence identity is counterbalanced by other similarities, including, for example, the presence of the same sequence motifs, binding to the same G-protein or having the same function, or having substantially the same hydropathy plots compared to the first parent GPCR.

Mapping of stabilising mutations onto the structural model can be done using any suitable method known in the art. For example, typically, the amino acid sequence of the GPCR for which the structural model is available is aligned with the amino acid sequence of the mutant of the first parent GPCR. The position or positions of the at least one different amino acid residue in the mutant GPCR relative to the first parent GPCR can then be located in the amino acid sequence of the GPCR for which a structural model is available.

By 'structural motif' we include the meaning of a three dimensional description of the location in a GPCR structural model of a thermostabilising mutation. For example, the structural motif may be any secondary or tertiary structural motif within the GPCR. By 'tertiary structural motif' we include any descriptor of atoms or groups of atoms, such as hydrogen bond donor or acceptor, hydrophobicity, shape, charge or aromaticity. For example, proteins may be spatially mapped according to such descriptors using GRID and this representation used as a basis for defining a structural motif (Baroni et al (2007) J Chem Inf Mod 47, 279-294).

Table (vi) lists the structural motifs in which the turkey β1 adrenergic receptor stabilising mutations were found to reside. As seen from the table, the mutations are positioned in a number of distinct localities. Three mutations are in loop regions that are predicted to be accessible to aqueous solvent. Eight mutations are in the transmembrane α-helices and point into the lipid bilayer; three of these mutations are near the end of the helices and may be considered to be at the hydrophobic-hydrophilic boundary layer. Eight mutations are found at the interfaces between transmembrane α-helices, three of which are either within a kinked or distorted region of the helix and another two mutations occur in one helix but are adjacent to one or more other helices which contain a kink adjacent in space to the mutated residue. These latter mutations could affect the packing of the amino acids within the kinked region, which could result in thermostabilisation. Another mutation is in a substrate binding pocket.

Accordingly, in one embodiment, the structural motif is any of a helical interface, a Do helix kink, a helix opposite a helix kink, a helix surface pointing into the lipid bilayer, a helix surface pointing into the lipid bilayer at the hydrophobic-hydrophilic boundary layer, a loop region or a protein binding pocket.

Identifying a structural motif in which a stabilising mutation resides suggests the importance of that motif in protein stability. Therefore, making one or more mutations in the amino acid sequence that defines a corresponding structural motif or motifs in a second parent GPCR, should provide one or more mutants of a second parent GPCR with increased stability relative to the second parent GPCR.

The amino acid sequence which defines a structural motif is the primary amino acid sequence of the amino acid residues which combine in the secondary or tertiary structure of the protein to form the structural motif. It will be appreciated that such a primary amino acid sequence may comprise contiguous or non-contiguous amino acid residues. Thus, identifying the amino acid sequence which defines the structural motif will involve determining the residues involved and subsequently defining the sequence. Mutations can be made in an amino acid sequence, for example as described above and using techniques well-established in the art.

By "corresponding structural motif or motifs", we mean the analogous structural motif or motifs identified in the structural model which are present in the second parent GPCR. For example, if a helical interface was identified, the corresponding helical interface in the second parent GPCR would be the interface between the helices which are analogous to the helices present in the structural model. If a helical kink was identified, the corresponding helical kink would be the kink in the helix which is analogous to the kinked helix present in the structural model. An analogous structural motif or motifs in the second parent GPCR can be identified by searching for similar amino acid sequences in the sequence of the second parent GPCR which define the motif or motifs in the structural model, for example, by sequence alignment. Moreover, computer based algorithms are widely available in the art that can be used to predict the presence of protein motifs based on an amino acid sequence. Thus, based upon the relative position of a particular motif within the amino acid sequence and its position relative to other motifs, an analogous structural motif can readily be identified. It will be appreciated that if a structural model of the second parent GPCR is available, the analogous structural motif or motifs can be directly mapped onto the structure of the protein. Typically, the amino acid sequence defining the analogous structural motif has at least 20% sequence identity with the sequence defining the motif in the structural model, more preferably at least 30%, 40%, 50%, 60%, 70%, 80% and 90% sequence identity and yet more preferably 95% and 99% sequence identity.

In one embodiment, the second parent GPCR is the first parent GPCR. For the avoidance of doubt, the second parent GPCR may have the naturally-occurring sequence of the first parent GPCR, or it may be a truncated form or it may be a fusion, either to the naturally occurring protein or to a fragment thereof, or it may contain mutations compared to the naturally-occurring sequence, providing that it retains ligand-binding.

In an alternative embodiment, the second parent GPCR is not the first parent GPCR. For example, a mutant of a first parent GPCR may have been identified that has increased stability but it is desired to generate a mutant of a different GPCR with increased stability. Preferably, the second parent GPCR is of the same GPCR class or family as the first parent GPCR as described above. However, it will be appreciated that the second parent GPCR may be any known GPCR provided that it shares sufficient structural similarity with the first parent GPCR, such that it contains a corresponding structural motif in which the stabilising mutation of the mutant of the first parent GPCR resides. Thus typically, the second parent GPCR has at least 20% sequence identity to the first parent GPCR and more preferably at least 30%, 40%, 50%, 60%, 70%, 80% or 90% sequence identity. However, as mentioned above, some GPCRs have low sequence identity (e.g. family B and C GPCRs) but are similar in structure. Thus the 20% sequence identity threshold is not absolute.

Since there are potentially thousands of mutations that can be screened in a GPCR for increased stability, it is advantageous to target particular mutations which are known to be important in conferring stability. Therefore, it will be appreciated that the methods of the eighth and ninth aspects of the invention may be used in a method of selecting mutant GPCRs with increased stability. In particular, carrying out the methods of the eighth or ninth aspects of the invention can be used to target mutations to particular amino acid residues or to amino acid sequences which define structural motifs important in determining stability.

Accordingly, in one embodiment the methods of the eighth or ninth aspects further comprise:
(I) selecting a ligand, the ligand being one which binds to the second parent GPCR when the GPCR is residing in a particular conformation
(II) determining whether the or each mutant of the second parent GPCR when residing in a particular conformation has increased stability with respect to binding the selected ligand compared to the stability of the second parent GPCR when residing in the same particular conformation with respect to binding that ligand, and
(III) selecting those mutants that have an increased stability compared to the second parent GPCR with respect to binding the selected ligand.

It will be noted that steps (I), (II) and (III) correspond to steps (b), (c) and (d) of the method of the first aspect of the invention described above. Accordingly, preferences for the ligand and methods of assessing stability are as defined above with respect to the method of the first aspect of the invention.

A tenth aspect of the invention provides a mutant GPCR with increased stability relative to its parent GPCR produced by the method of the tenth aspect of the invention.

In one embodiment, the mutant GPCR of the tenth aspect of the invention is a mutant GPCR which has, compared to its parent receptor, at least one different amino acid at a position which corresponds to any one or more of the following positions: (i) according to the numbering of the turkey β-adrenergic receptor as set out in FIG. 9: Ile 55, Gly 67, Arg 68, Val 89, Met 90, Gly 67, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315, (iii) according to the numbering of the rat neurotensin receptor as set out in FIG. 11: Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399, and (iv) according to the numbering of the muscarinic receptor as set out in FIG. 17: Leu 65, Met 145, Leu 399, Ile 383 and Met 384.

Alignment of the turkey β1 AR, human adenosine receptor, rat neurotensin receptor and human muscarinic receptor amino acid sequences in FIG. 17, shows that in 11 instances out of 70, two sequences contain mutations art the same position, namely at the following positions according to the numbering of the human beta2 AR as set out in FIG. 17: Ala 59, Val 81, Ser 143, Lys 147, Val 152, Glu 180, Val 222, Ala 226, Ala 271, Leu 275 and Val 317. Therefore, in a preferred embodiment, the mutant GPCR of the tenth aspect of the invention is one which has, compared to its parent receptor, a different amino acid at any one of these positions.

In one embodiment the mutant GPCR of the tenth aspect of the invention is a mutant β-adrenergic receptor. For example, the mutant β-adrenergic receptor may have at least one different amino acid residue in a structural motif in which the mutant receptor compared to its parent receptor has a different amino acid at a position which corresponds to any of the following positions according to the numbering of the turkey β-adrenergic receptor as set out in FIG. 9: Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338.

In one embodiment the mutant GPCR of the tenth aspect of the invention is a mutant adenosine receptor. For example, the mutant adenosine receptor may have at least one different amino acid residue in a structural motif in which the mutant receptor compared to its parent receptor has a different amino acid at a position which corresponds to any of the following positions according to the numbering of the human adenosine Ata receptor as set out in FIG. 10: Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315.

In one embodiment the mutant GPCR of the tenth aspect of the invention is a mutant neurotensin receptor. For example, the mutant neurotensin receptor may have at least one different amino acid residue in a structural motif in which the mutant receptor compared to its parent receptor has a different amino acid at a position which corresponds to any of the following positions according to the numbering of the rat neurotensin receptor as set out in FIG. 11: Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399.

In one embodiment the mutant GPCR of the tenth aspect of the invention is a mutant muscarinic receptor. For example, the mutant muscarinic receptor may have at least one different amino acid residue in a structural motif in which the mutant receptor compared to its parent receptor has a different amino acid at a position which corresponds to any of the following positions according to the numbering of the human muscarinic receptor as set out in FIG. 17: Leu 65, Met 145, Leu 399, Ile 383 and Met 384.

It is preferred that the mutant GPCRs of the invention have increased stability to any one of heat, a detergent, a chaotropic agent and an extreme of pH.

It is preferred if the mutant GPCRs of the invention have increased thermostability.

It is preferred that the mutant GPCRs of the invention, including the mutant β-adrenergic, adenosine and neurotensin receptors, have an increased thermostability compared to its parent when in the presence or absence of a ligand thereto. Typically, the ligand is an antagonist, a full agonist, a partial agonist or an inverse agonist, whether orthosteric or allosteric. As discussed above, the ligand may be a polypeptide, such as an antibody.

It is preferred that the mutant GPCRs of the invention, for example a mutant β-adrenergic receptor or a mutant adenosine receptor or a mutant neurotensin receptor is at least 2° C. more stable than its parent preferably at least 5° C. more stable, more preferably at least 8° C. more stable and even more preferably at least 10° C. or 15° C. or 20° C. more stable than its parent. Typically, thermostability of the parent and mutant receptors are measured under the same conditions. Typically, thermostability is assayed under a condition in which the GPCR resides in a particular conformation. Typically, this selected condition is the presence of a ligand which binds the GPCR.

It is preferred that the mutant GPCRs of the invention, when solubilised and purified in a suitable detergent has a similar thermostability to bovine rhodopsin purified in dodecyl maltoside. It is particularly preferred that the mutant GPCR retains at least 50% of its ligand binding activity after heating at 40° C. for 30 minutes. It is further preferred that the mutant GPCR retains at least 50% of its ligand binding activity after heating at 55° C. for 30 minutes.

The mutant GPCRs disclosed herein are useful for crystallisation studies and are useful in drug discovery programmes. They may be used in biophysical measurements of receptor/ligand kinetic and thermodynamic parameters eg by surface plasmon resonance or fluorescence based techniques. They may be used in ligand binding screens, and may be coupled to solid surfaces for use in high throughput screens or as biosensor chips. Biosensor chips containing the mutant GPCRs may be used to detect molecules, especially biomolecules.

The invention also includes a polynucleotide which encodes a mutant GPCR of the invention. In particular, polynucleotides are included which encode the mutant β-adrenergic receptor or the mutant adenosine receptors or the mutant neurotensin receptors of the invention. The polynucleotide may be DNA or it may be RNA. Typically, it is comprised in a vector, such as a vector which can be used to express the said mutant GPCR. Suitable vectors are ones which propagate in and/or allow the expression in bacterial or mammalian or insect cells.

The invention also includes host cells, such as bacterial or eukaryotic cells, which contain a polynucleotide which encodes the mutant GPCR. Suitable cells include *E. coli* cells, yeast cells, mammalian cells and insect cells.

The invention will now be described in more detail with respect to the following Figures and Examples wherein:

FIG. 1 Amino acid changes in βAR that lead to thermostability. Stability quotient indicates the % remaining binding activity of the mutants after heating the sample for 30 min at 32° C. All values are normalized to $βAR_{34-424}$ (50%, showed as a discontinuous line) to remove any experimental variability between assays. Bars show the stability for each mutant. The letters on the x-axis indicate the amino acid present in the mutant. The original amino acid and its position in $βAR_{34-424}$ is indicated below. Bars corresponding to the same amino acid in $βAR_{34-424}$ are in the same colour with arrows indicating the best mutations. Errors were calculated from duplicate measurements; the best mutants were subsequently re-assayed to determine the Tm for each individual mutation and to give an accurate rank order of stability for each mutant (see Example 1).

Figure 2:
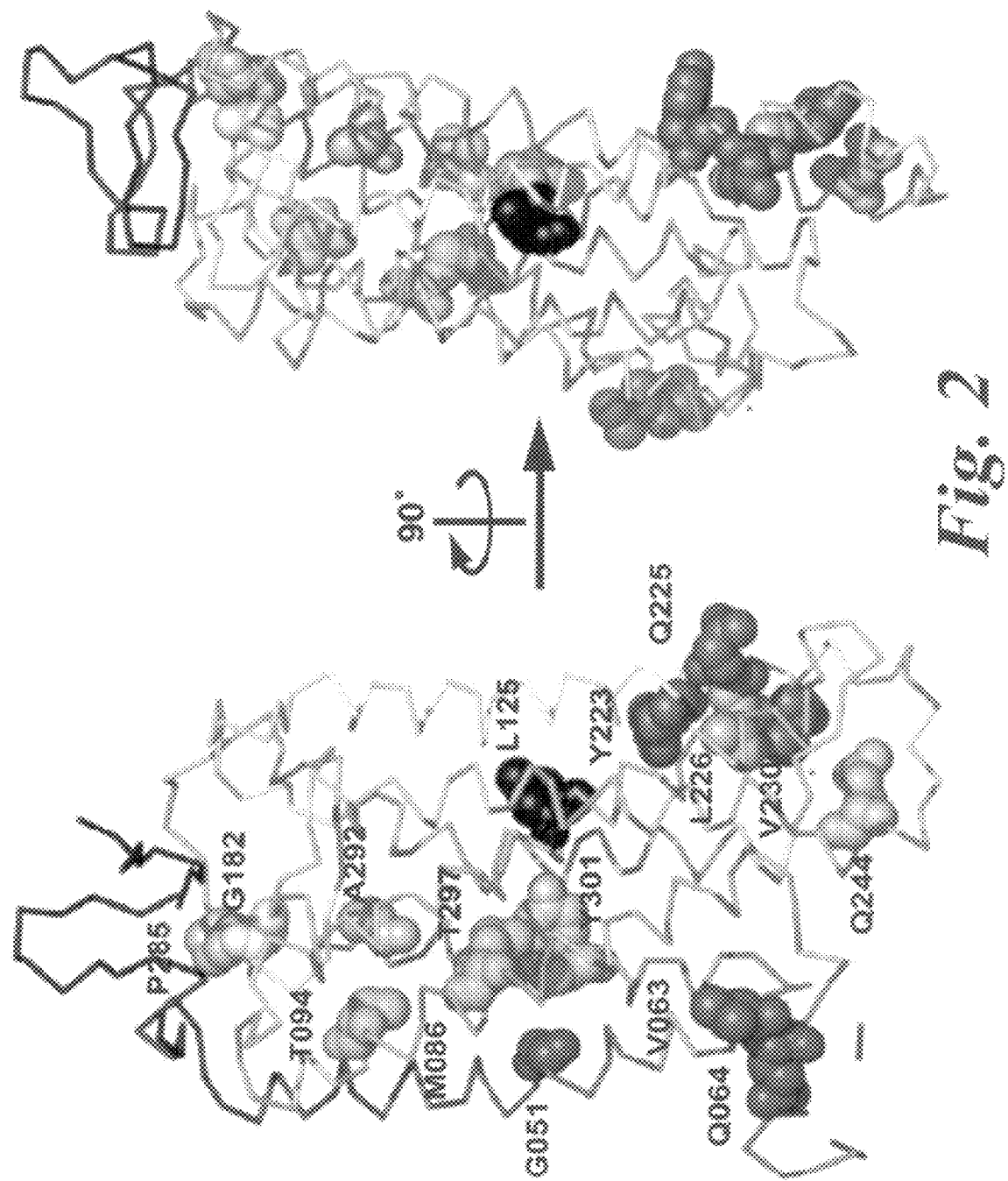

FIG. 2 Side chains in rhodopsin that are at equivalent positions to the thermostable mutations in $βAR_{34-424}$. The equivalent amino acid residues in rhodopsin to the amino acid residues mutated in $βAR_{34-424}$ were located in the rhodopsin structure, based upon an alignment among rhodopsin, β1 adrenergic receptor, neurotensin receptor, and adenosine $A_{2a}$ receptor (data not shown). Side chains in the same transmembrane helix are shown as space filling models in the same colour. The name and position of the amino acid residues are those in rhodopsin.

Figure 3:
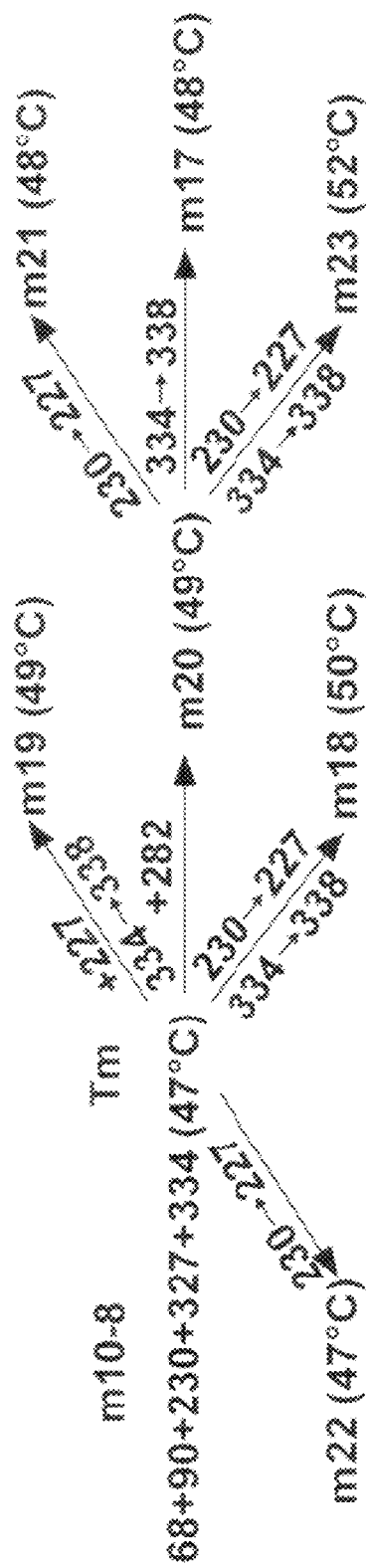

FIG. 3 Evolution of thermostability in βAR. Starting from βAR-m10-8, combinations of mutations were rearranged systematically to find the optimum combination of mutations (see also Table 2).

Figure 4:
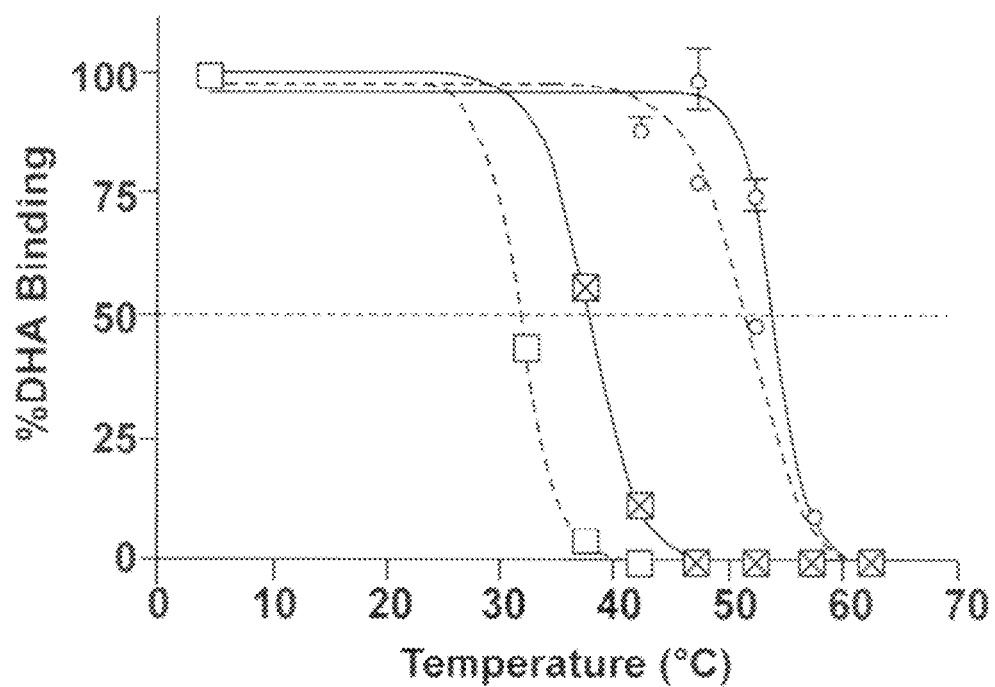

FIG. 4 Stability of βAR-m23 and $βAR_{34-424}$ in the apo-state or containing the bound antagonist [$^3$H]-DHA. To determine Tm in the absence of ligand (apo-state, discontinuous lines), detergent-solubilised receptors were incubated for 30 minutes at the temperatures indicated before carrying out the binding assay. For the Tm determination of the antagonist-bound form (continuous lines), detergent-solubilised receptors were pre-incubated with [$^3$H]-DHA, followed by incubation at the temperatures indicated. βAR-m23 (circles), and $βAR_{34-424}$ (squares). Data points are from duplicates measurements in a representative experiment.

Figure 5A:
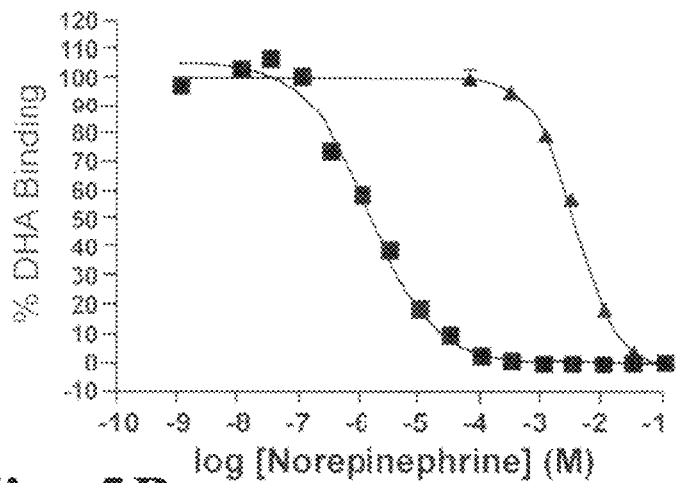
Figure 5B:
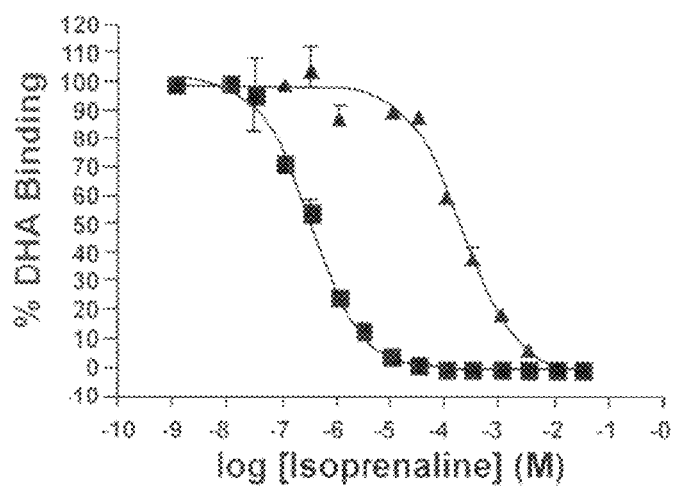
Figure 5C:
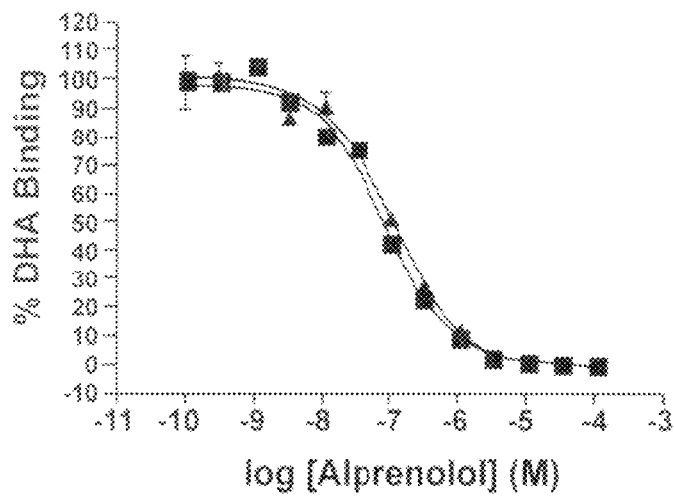

FIGS. 5a-c Competition binding of agonists to βAR-m23 and $βAR_{34-424}$. Binding assays were performed on receptors partially purified in DDM; βAR-m23 (triangles) and $βAR_{34-424}$ (squares). [$^3$H]-DHA was used at a concentration three times greater than the $K_D$ of partially purified receptor (see Methods). [$^3$H]-DHA binding was competed with increasing concentrations of the agonists, norepinephrine (FIG. 5a) and isoprenaline (FIG. 5b), or with an antagonist, alprenolol (FIG. 5c). Log $EC_{50}$ and corresponding $EC_{50}$ values for the different ligands were calculated by nonlinear regression using GraphPad Prism software and the error for log $EC_{50}$s were lower than 10%. The $EC_{50}$s for ligand binding to $βAR_{34-424}$ and βAR-m23 are: norepinephrine, $βAR_{34-424}$ 1.5 μM, βAR-m23 3.7 mM; isoprenaline, $βAR_{34-424}$ 330 nM, βAR-m23 20 μM; alprenolol, βAR 78 nM, βAR-m23 112 nM.

FIGS. 6a-c Stability of βAR-m23 and $βAR_{34-424}$ in five different detergents. Samples of $βAR_{34-424}$ (FIG. 6a), and βAR-m23 (FIG. 6b) solubilized in DDM were partially purified on Ni-NTA agarose columns allowing the exchange into various different detergents: DDM (squares), DM (triangles), OG (inverted triangles), LDAO (diamonds) and NG (circles). βAR is so unstable in OG, NG and LDAO that it was not possible to measure any activity after purification at 6° C. Assays were carried out as described in the Methods and the Tm is shown at the intersection between the curves and the discontinuous line. Results are from duplicate measurements in a representative experiment performed in parallel. (FIG. 6c) Photomicrograph of a crystal of βAR-m23 mutant, which showed good order by X-ray diffraction.

Figure 7:
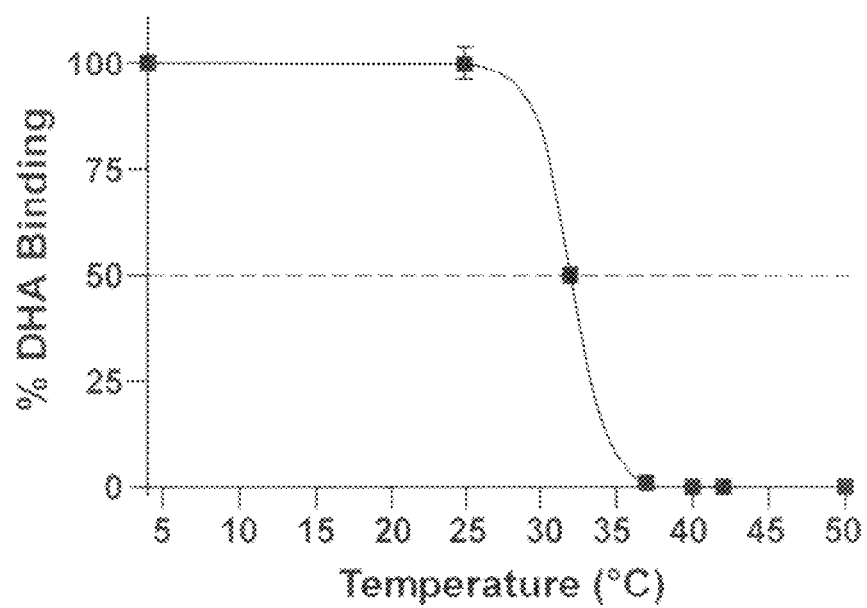

FIG. 7 Curve of thermostability of $βAR_{34-424}$ (Tm). Binding assays were performed using [$^3$H]-dihydroalprenolol (DHA) as radioligand as described under "Methods". Samples were heated for 30 minutes at different temperatures before the assay. Tm represents the temperature at which the binding decreased to the 50%, value showed as a discontinuous line. Data points are from duplicates of one single experiment. This experiment has been repeated several times with similar results.

Figure 8A:
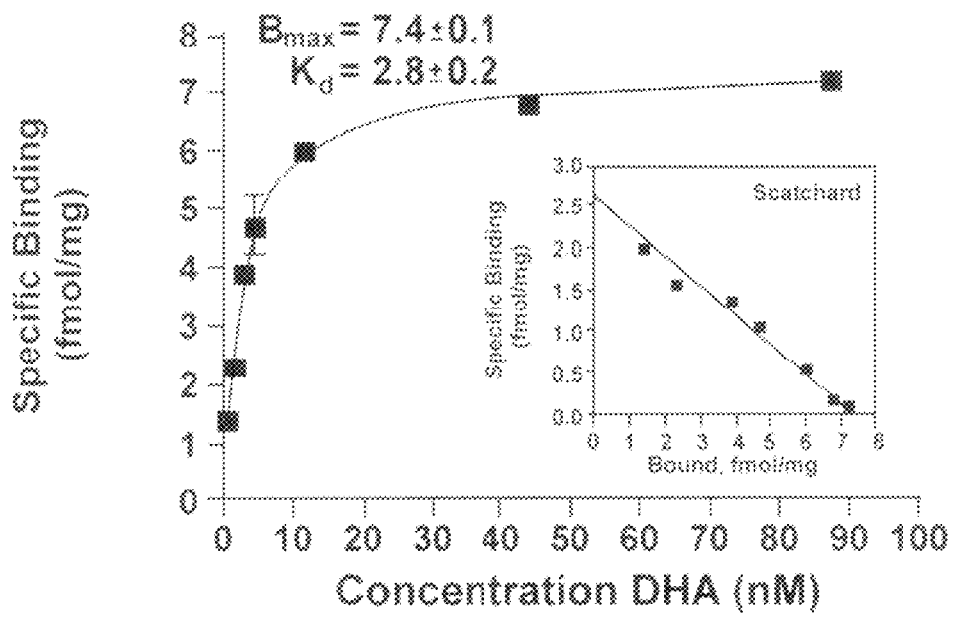
Figure 8B:
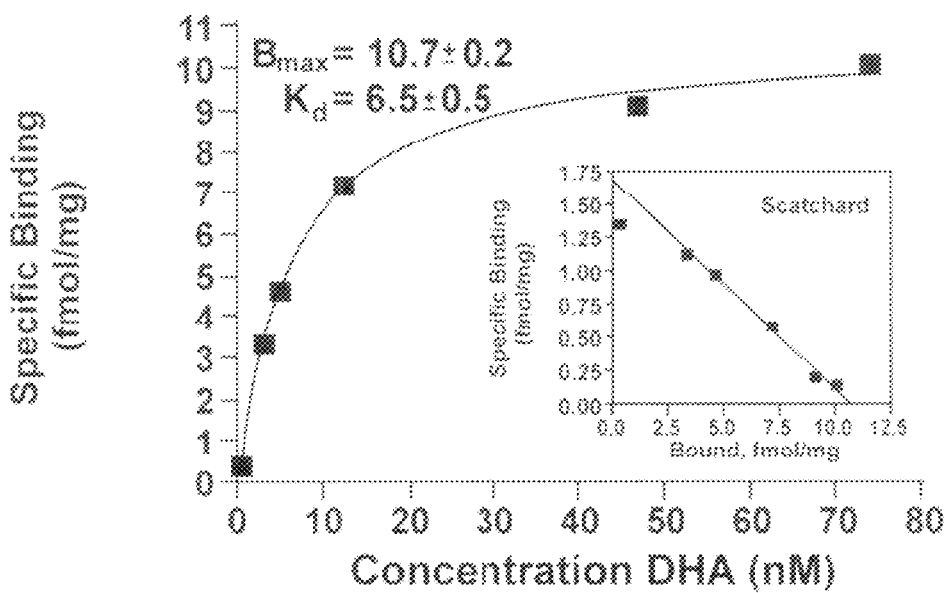

FIGS. 8a-b Saturation binding assays of membranes of $\beta AR_{34-424}$ and $\beta AR$-m23. Binding assays were performed as described in "Methods" using [$^3$H]-dihydroalprenolol (DHA) as radioligand; $\beta AR_{34-424}$ (FIG. 8a) and $\beta AR$-m23 (FIG. 8b). Scatchard plots are shown as insets along with the corresponding values for $B_{max}$ and $K_D$. Data points are from duplicates of two independent experiments for each protein. Data were analyzed by nonlinear regression using Prism software (GraphPad).

FIGS. 9A-B Alignment of the turkey β-adrenergic receptor with human β1, β2 and β3 receptors.

FIGS. 10A-B Alignment of human adenosine receptors.

FIGS. 11A-B Alignment of neurotensin receptors.

Figure 12:
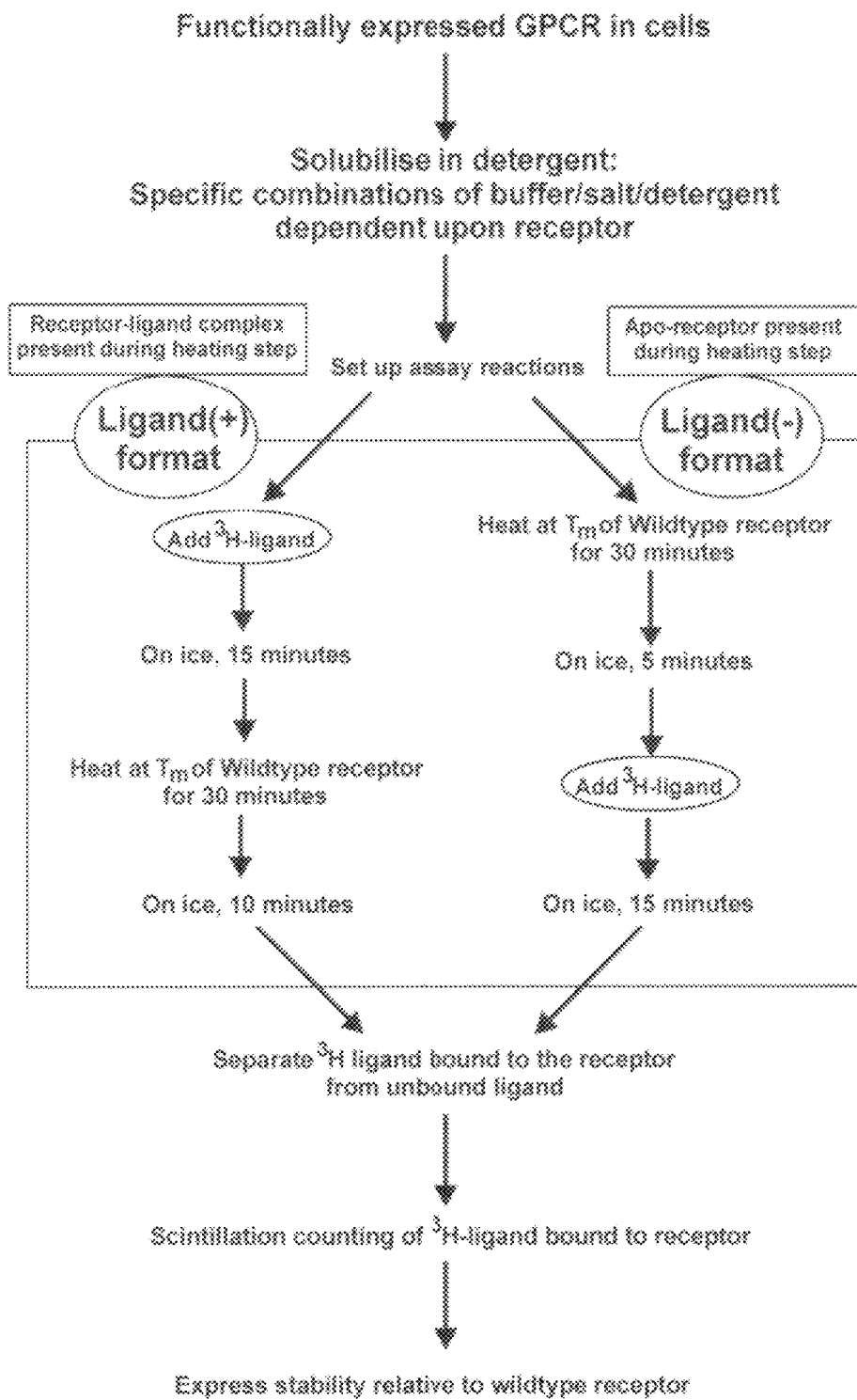
Figure 13A:
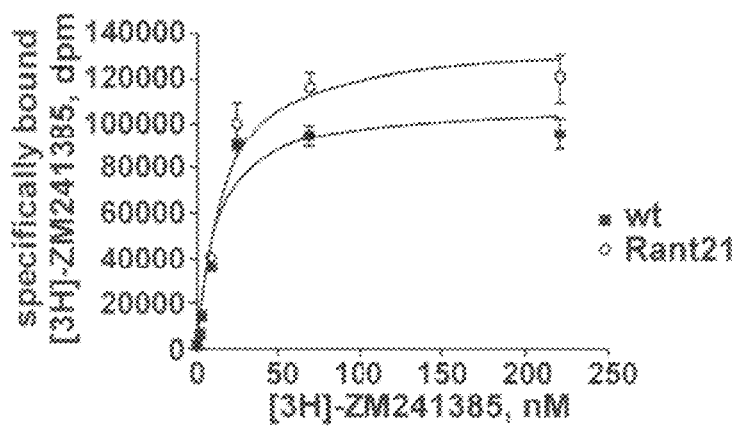
Figure 13B:
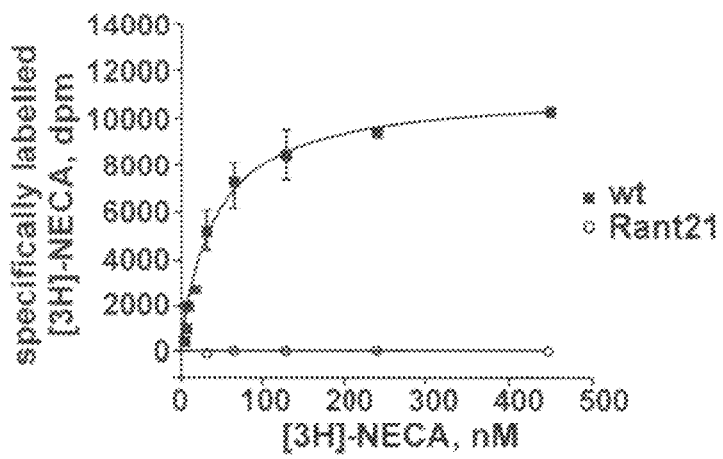
Figure 13C:
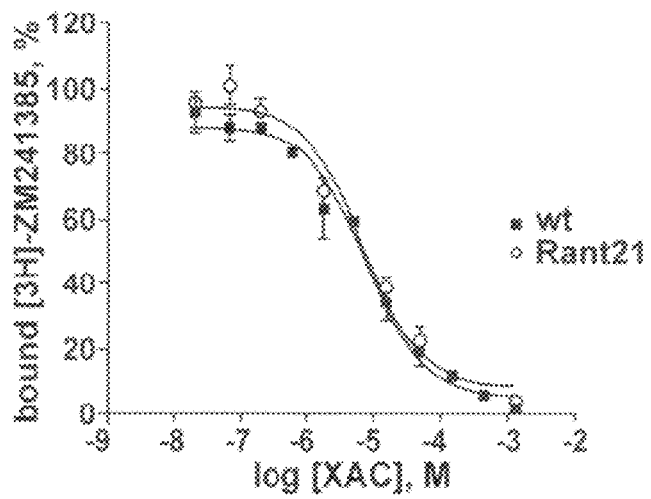
Figure 13D:
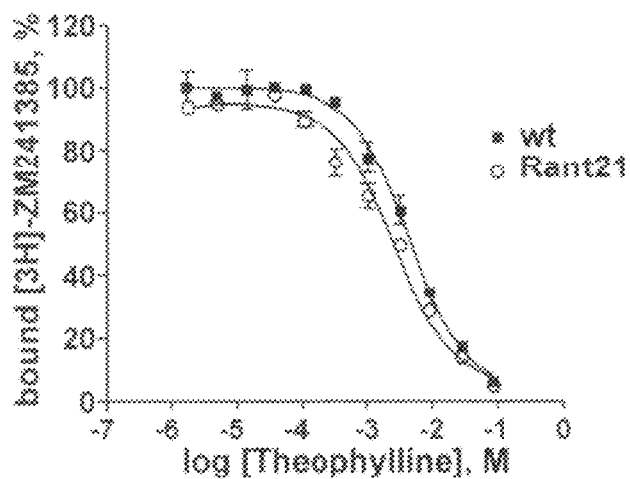
Figure 13E:
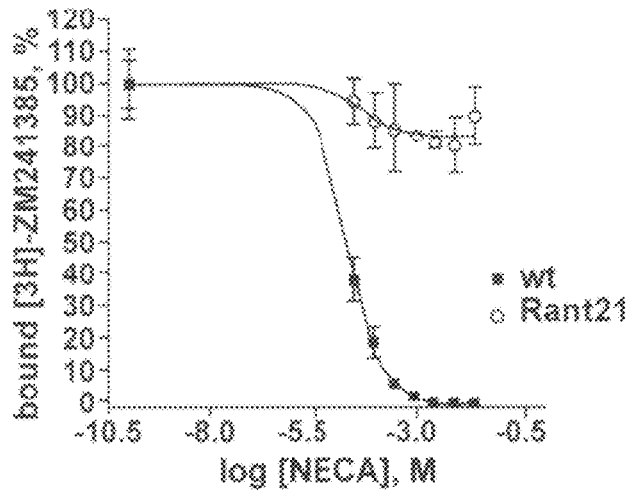
Figure 13F:
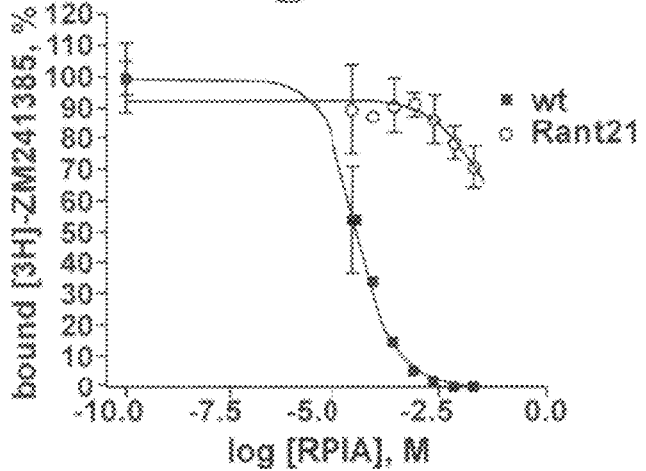

FIG. 12 Flow chart showing the two different assay formats of ligand (+) and ligand (−) used to determine receptor thermostability.

FIGS. 13A-F Pharmacological profile of thermostable mutant adenosine A2a receptor, Rant21. Saturation binding of (FIG. 13A) antagonist and (FIG. 13B) agonist to solubilised receptors. (FIGS. 13C-F) Inhibition of [$^3$H]ZM241385 binding by increasing concentrations of antagonists (FIG. 13C) XAC and (FIG. 13D) Theophylline, and agonists (FIG. 13E) NECA and (FIG. 13F) R-PIA; binding of [$^3$H]ZM241385 (10 nM) in the absence of unlabelled ligand was set to 100%. Each solubilised receptor was incubated with ligands for one hour on ice in binding buffer (50 mM Tris pH7.5 and 0.025% DDM) containing 400 mM NaCl (FIG. 13A, FIG. 13C-F). Data shown are from two independent experiments with each data point measured in triplicate. $K_D$ and $K_i$ values are given in Table (iii).

Figure 14A:
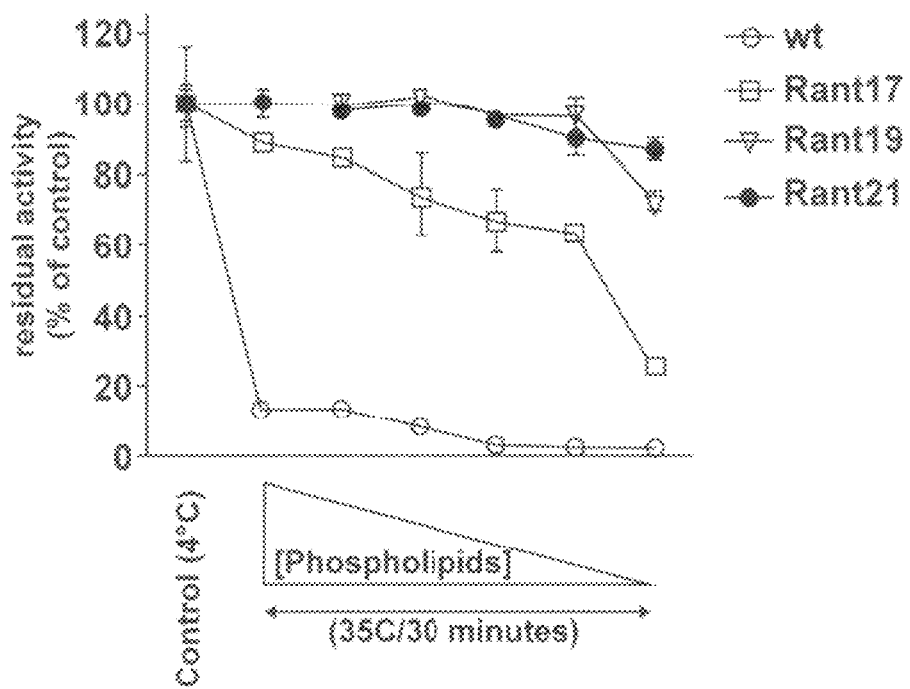
Figure 14B:
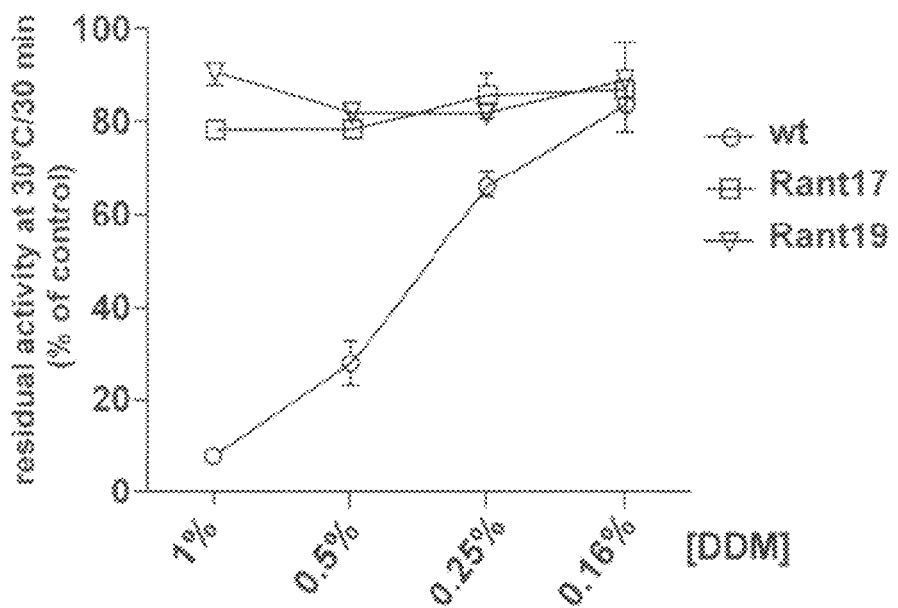

FIGS. 14A-B Thermostable mutants show a decreased dependence on lipids (FIG. 14A) and an increased survival at higher concentration of DDM (FIG. 14B) upon heating compared to the wild-type receptor. Receptors were solubilised in 1% DDM (diluted in 50 mM Tris pH7.5 and 400 mM NaCl) and immobilised on Ni-NTA agarose for the IMAC step. Exchange of buffer containing the appropriate concentration of DDM and/or lipids was performed during washes and elution from the Ni-NTA beads.

Figure 15:
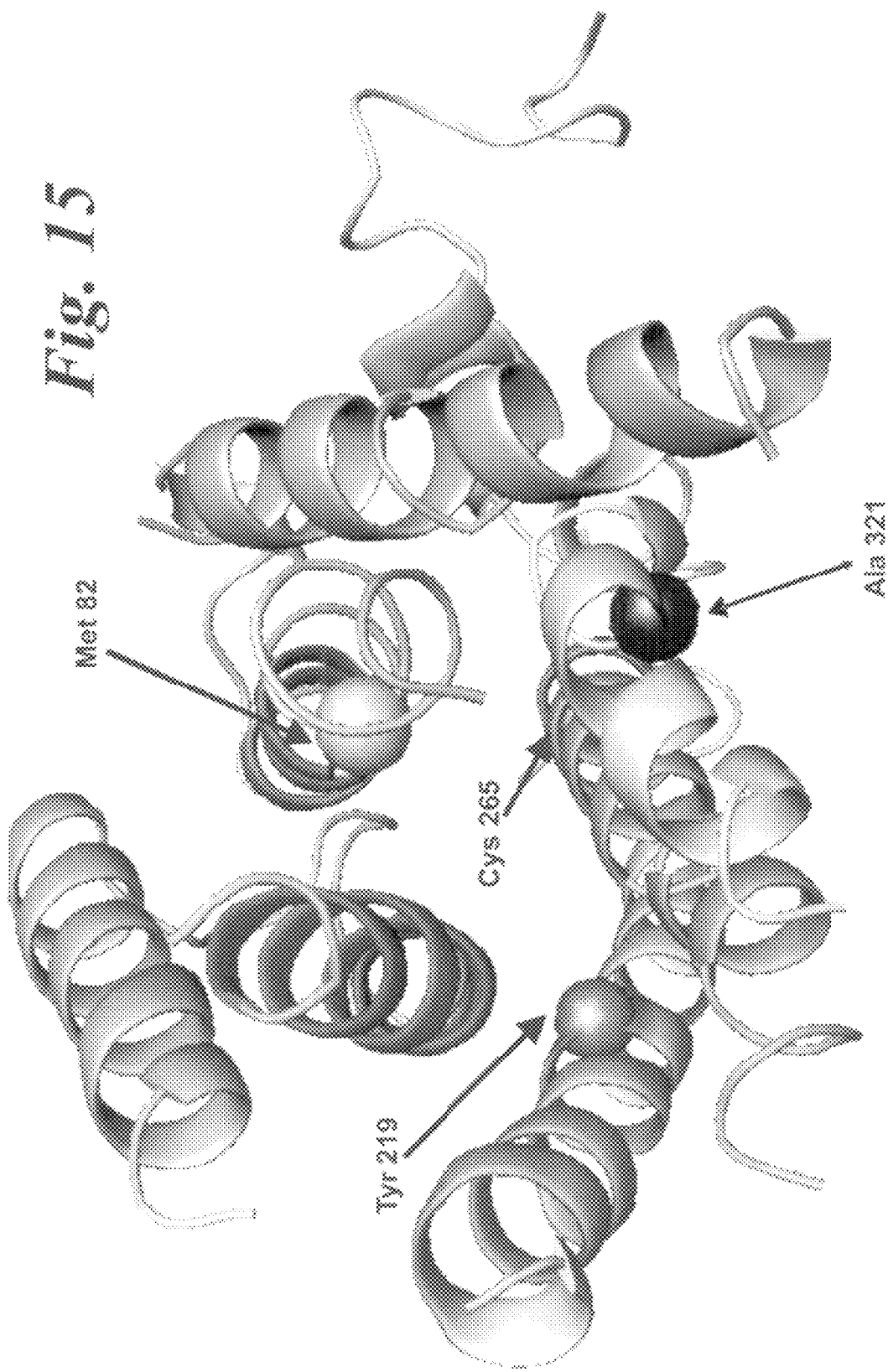

FIG. 15 Mapping of the M90V, Y227A, A282L and F338M m23 mutations in turkey beta1 adrenergic receptor onto homologous residues (M82, Y219, C265 and A321 respectively) in the human beta2 adrenergic receptor structure (Rasmussen et al (2007) Nature 15; 383-387; pdb accession codes 2R4R and 2R4S) reveals their position at a helical interface and helical kink respectively. Amino acid residues in equivalent positions to the thermostabilising mutations in the turkey β1 adrenergic receptor are shown as labelled space filling models.

Figure 16:
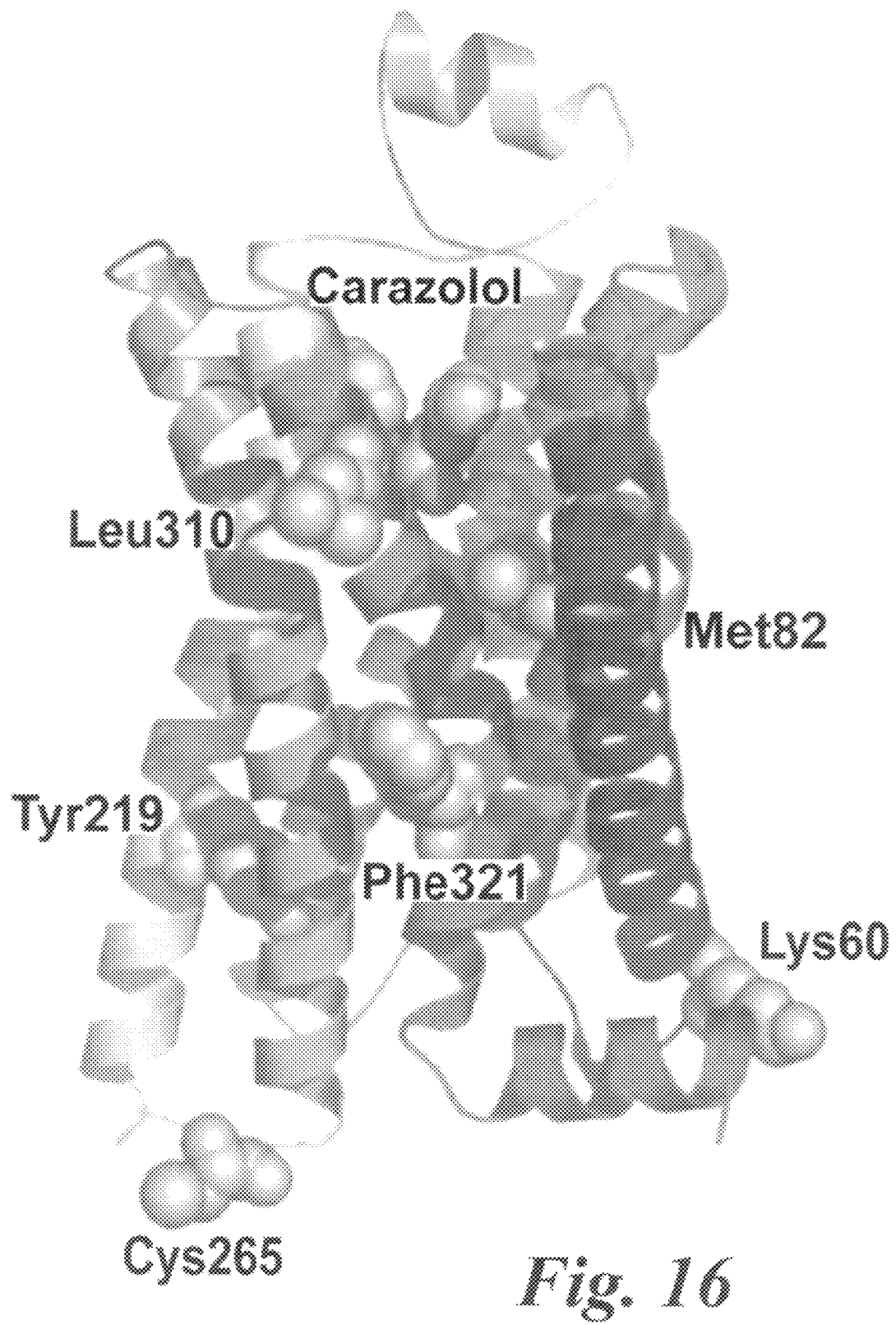

FIG. 16 Mapping of m23 mutations in turkey beta1 adrenergic receptor onto homologous residues in the human beta2 adrenergic receptor structure (Cherezov et al (2007) Science, 318:1258-65; pdb accession code 2RH1). The Cα trace of the β2AR is shown with the fusion moiety (T4 lysozyme) removed. The six mutations in PAR-m23 (R68S, M90V, Y227A, A282L, F327A, F338M) are equivalent to amino acid residues K60, M82, Y219, C265, L310, F321 in the human β2AR. Lys60 is on the intracellular end of Helix 1 and points into the lipid-water interface. Met82 is near the middle of Helix 2 and points into the ligand binding pocket; the nearest distance between the substrate carazolol and the Met side chain is 5.7 Å. Tyr219 is towards the intracellular end of helix 5 and is at the helix5-helix 6 interface. Cys265 is at the end of the loop region between helices 5 and 6 and points away from the transmembrane regions. Leu310 and Phe321 are both in helix 7 and both point out into the lipid bilayer.

Figure 17A:
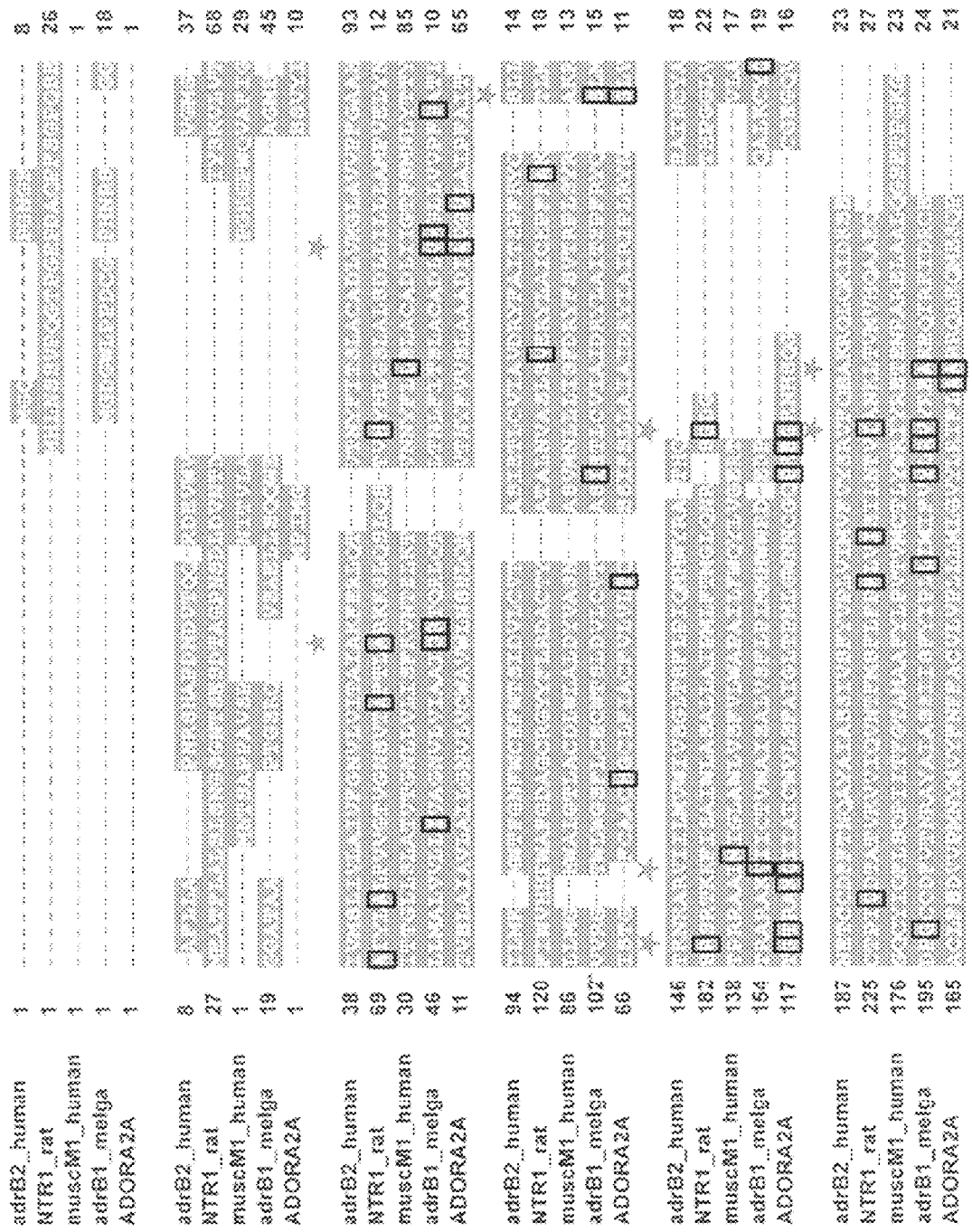
Figure 17B:
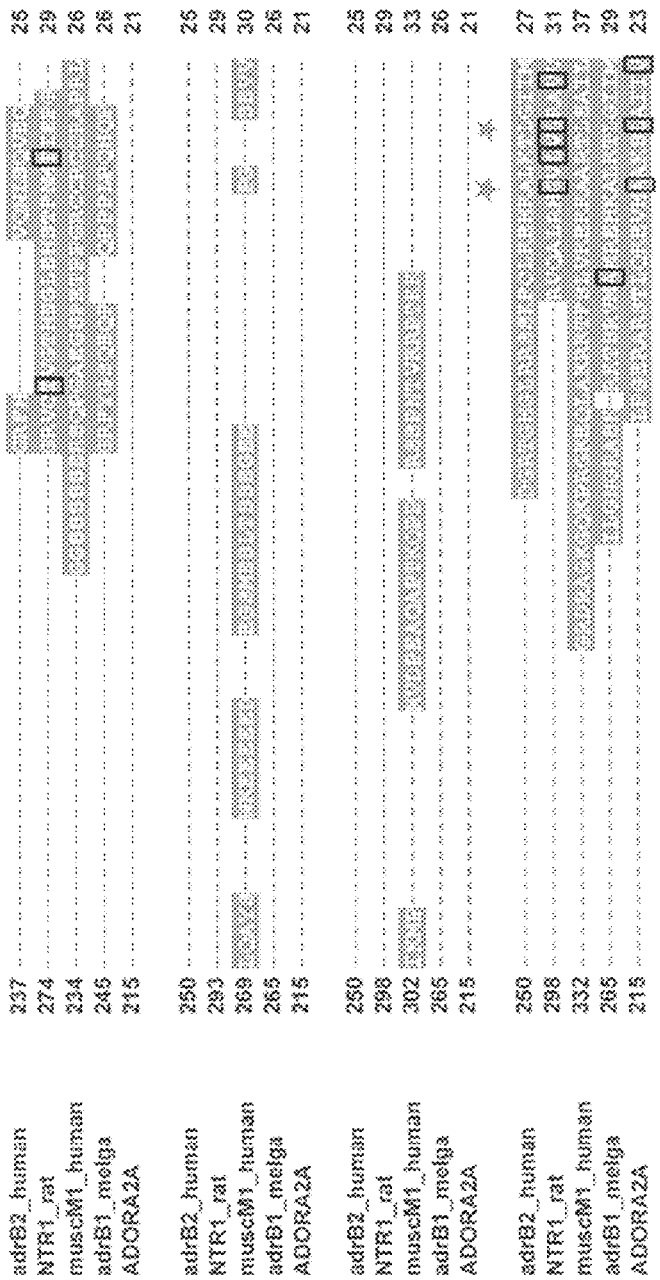
Figure 17C:
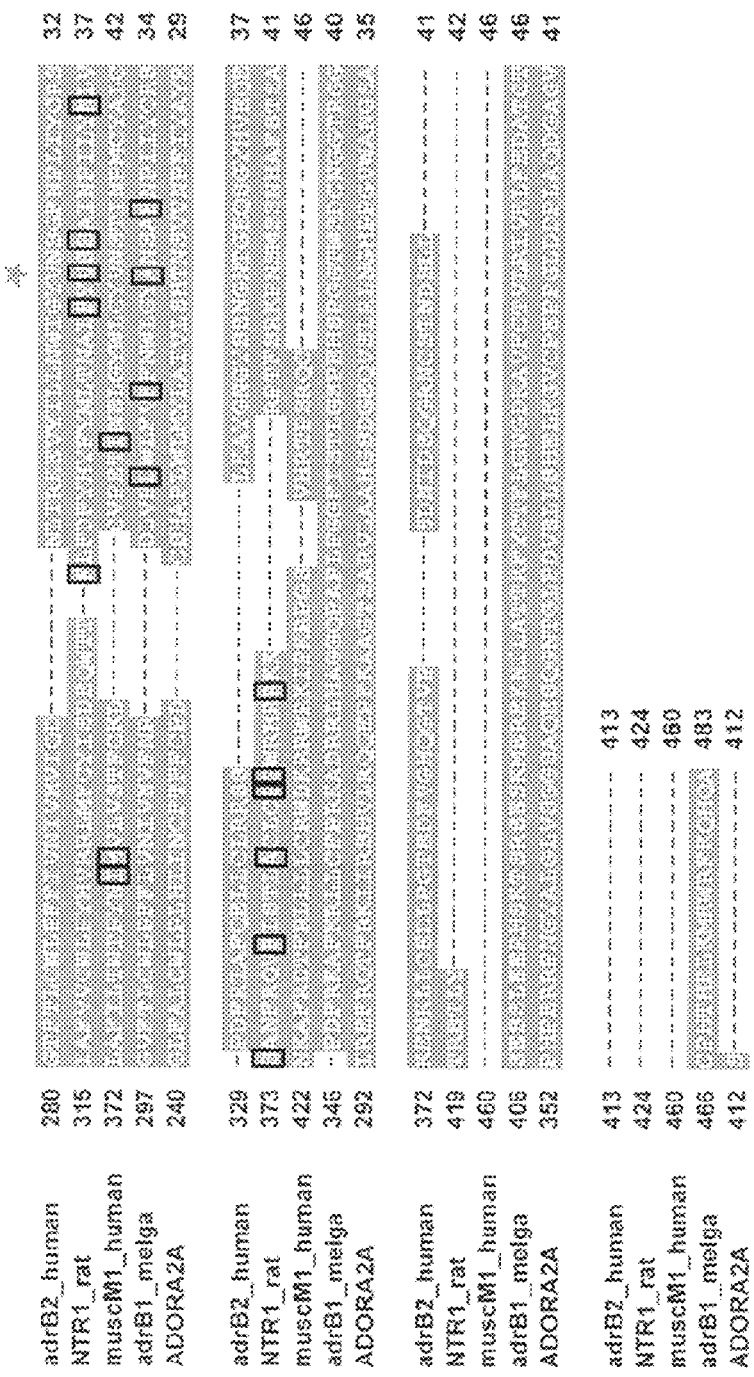

FIGS. 17A-C Multiple sequence alignment of human beta-2AR, rat NTR1, turkey beta-1 AR, human Adenosine A2aR and human muscarinic M1 receptors. In each sequence, thermostabilising mutations are marked with a box. Mutations occurring in two or more sequences are denoted with a star.

FIG. 18 Mapping of turkey beta1AR mutation I55A (human beta2AR 147) onto human beta2AR structure (pdb accession code 2RH1). Mutation is at the interface between 3 helices (H1, H2 kink, H7 kink). Left: side view; right: top view.

FIG. 19 Mapping of turkey beta1AR V89L mutation (human beta2AR V81) onto human beta2AR structure (pdb accession code 2RH1). Mutation is in the kink in helix 2. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: top view.

Figure 20:
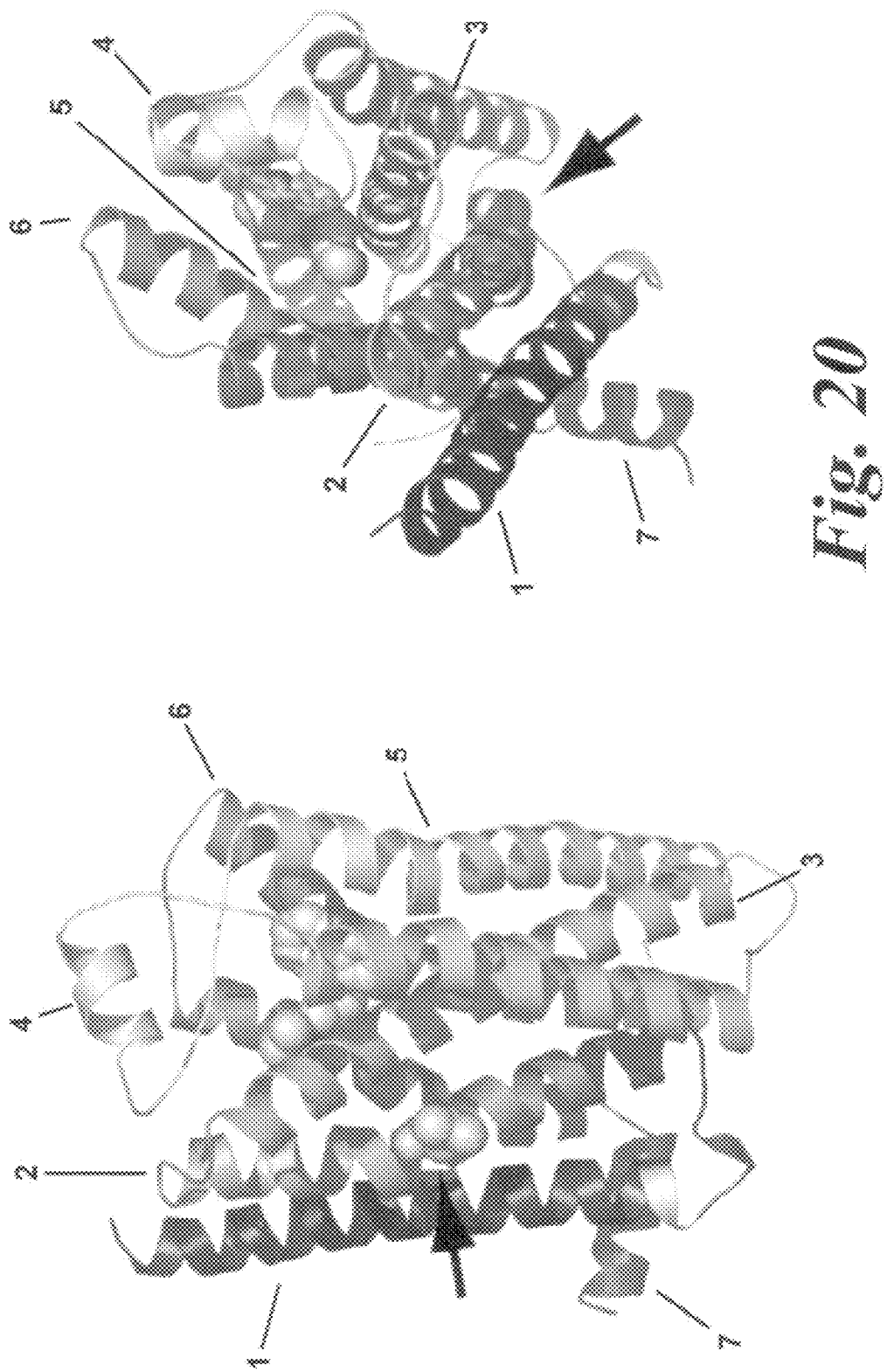

FIG. 20 Mapping of turkey beta1AR M90V mutation (human beta2AR M82) onto human beta2AR structure (pdb accession code 2RH1). Mutation is in kink in helix 2 oriented towards the binding pocket. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: top view.

FIG. 21 Mapping of turkey beta1AR I129V mutation (human beta2AR I121) onto human beta2AR structure (pdb accession code 2RH1). Mutation is opposite a kink in helix 5. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: bottom view.

FIG. 22 Mapping of turkey beta1AR F338M mutation (human beta2AR F321) onto human beta2AR structure (pdb accession code 2RH1). Mutation is in kink in helix 7. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: top view.

FIG. 23 Mapping of turkey beta1AR Y227A mutation (human beta2AR Y219) onto human beta2AR structure (pdb accession code 2RH1). Mutation is at helix-helix interface. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: bottom view.

FIG. 24 Mapping of turkey beta1AR A282L mutation (human beta2AR C265) onto human beta2AR structure (pdb accession code 2RH1). Mutation is in loop region. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: top view.

Figure 25:
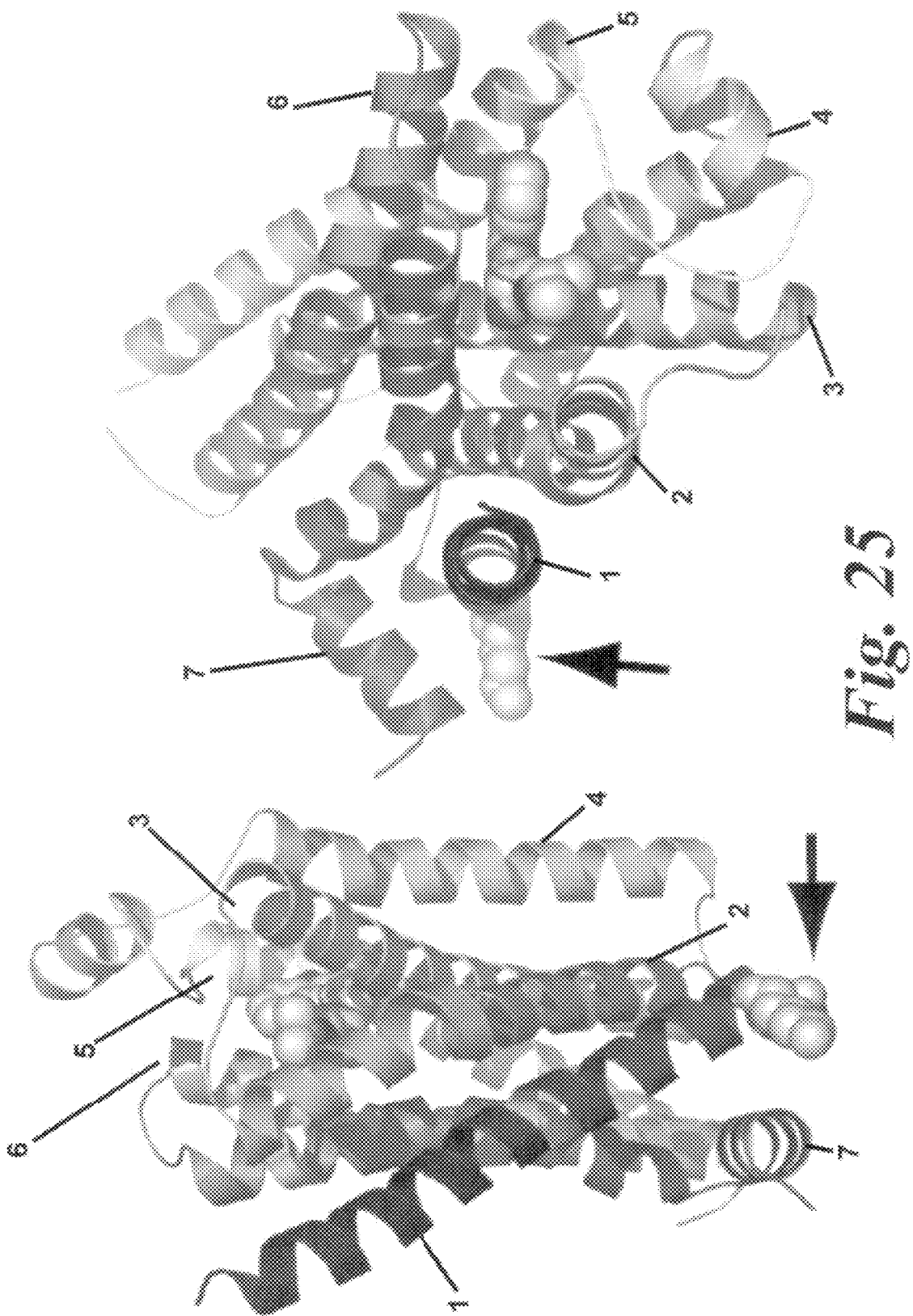

FIG. 25 Mapping of turkey beta1 AR R68S mutation (human beta2AR K60) onto human beta2AR structure (pdb accession code 2RH1). Mutation is at the lipid-water boundary, pointing into the solvent. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: angled top view.

FIG. 26 Comparison of the thermostabilities of three β adrenergic receptors (turkey β1 (■), human β1 (▼) and human β2 (●)) and two thermostabilised receptors (turkey β1-m23 (▲) and human β2-m23 (♦)). The six thermostabilising mutations in β1-m23 (R68S, M90V, Y227A, A282L, F327A, F338M) were all transferred directly to the human β2 receptor (K60S, M82V, Y219A, C265L, L310A, F321M) making β2-m23, based upon the alignment in FIGS. 9A-B. The resulting mutants were transiently expressed in mammalian cells, solubilised in 0.1% dodecylmaltoside and assayed for thermostability in the minus-ligand format (heating the apo-state, quenching on ice, adding 3H-DHA). The apparent Tms for turkey β1 and β2-m23 were 23° C. and 45° C. respectively, giving a ΔTm of 22° C. as seen previously in E. coli expressed receptor. The Tms for human β2 and β2-m23 were 29° C. and 41° C. respectively, showing that the apo receptor was stabilised by 12° C. This exemplifies the principle of the transferability of thermostabilising mutations from one receptor to another receptor, which in this case are 59% identical. The human β1 receptor (Tm~12° C.) is much less stable than the turkey β1 receptor.

FIG. 27 Percentage identity of the turkey β1 adrenergic receptor, human adenosine receptor and rat neurotensin receptor to human β adrenergic receptors, human adenosine receptors and human neurotensin receptors, respectively.

Figure 28B:
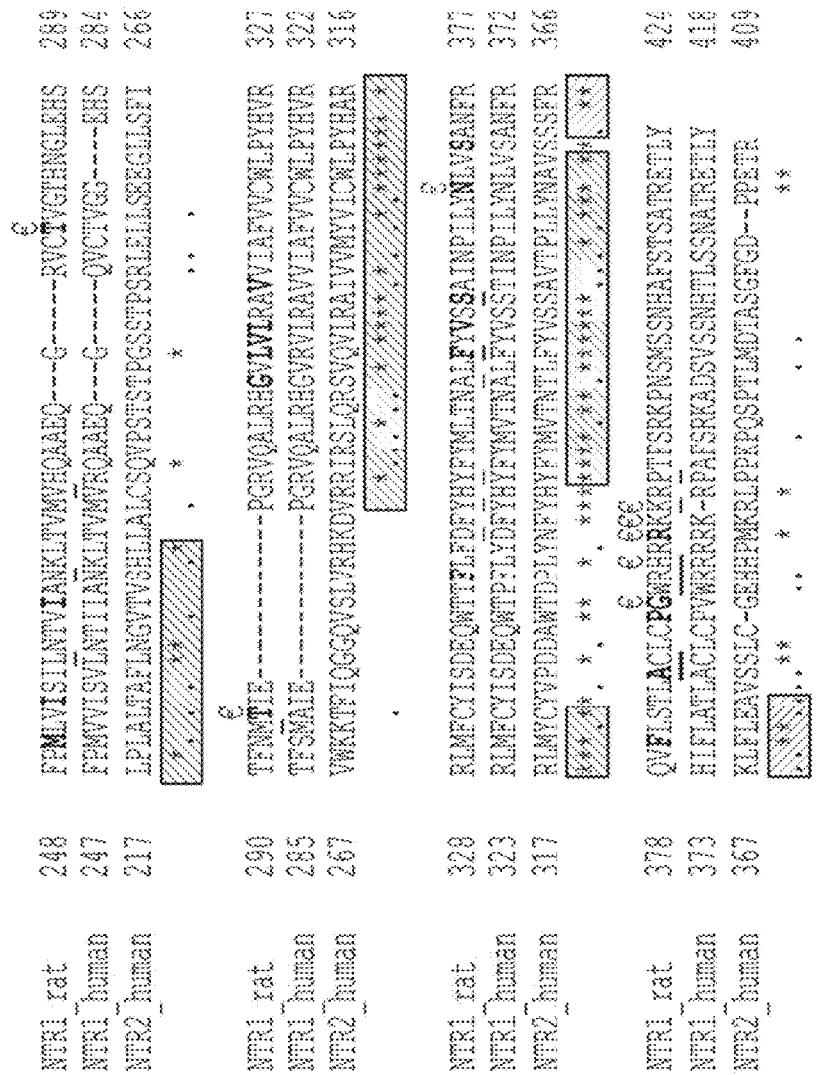

FIGS. 28A-B Alignment of neurotensin receptors.

FIG. 29 shows a list of A2aR stabilising mutations. Mutants were expressed in E. coli, solubilised in 2% DDM+ 10% glycerol and tested for ligand-binding, using the agonist [$^3$H]-NECA and the antagonist [$^3$H]-ZM241385. Concentrations of radioligands were 6-10-fold above their $K_D$ measured for the wild-type receptor. Expression of active receptor was evaluated by ligand binding at 4° C. Stability was assayed by heating the solubilised receptor in its apo-state at 30° C. for 30 minutes and then measuring residual binding activity. Under these conditions, wild-type activity decays to 50% (S.D.=15%). Data obtained for expression and stability were normalised to wild-type values. Mutations included in subsequent rounds of mutagenesis were those whose expression was ≥30-40% and stability ≥130-140% compared to the wild-type. Bold lines indicate cluster of mutations.

EXAMPLE 1

Conformational Stabilisation of the β-Adrenergic Receptor in Detergent-Resistant Form Summary There are over 500 non-odorant G protein-coupled receptors (GPCRs) encoded by the human genome, many of which are predicted to be potential therapeutic targets, but there is only one structure available, that of bovine rhodopsin, to represent the whole of the family. There are many reasons for the lack of progress in GPCR structure determination, but we hypothesise that improving the detergent-stability of these receptors and simultaneously locking them into one preferred conformation will greatly improve the chances of crystallisation. A generic strategy for the isolation of detergent-solubilised thermostable mutants of a GPCR, the β-adrenergic receptor, was developed based upon alanine scanning mutagenesis followed by an assay for receptor stability. Out of 318 mutants tested, 15 showed a measurable increase in stability. After optimisation of the amino acid residue at the site of each initial mutation, an optimally stable receptor was constructed by combining specific mutations. The most stable mutant receptor, βAR-m23, contained 6 point mutations that led to a Tm 21° C. higher than the native protein and, in the presence of bound antagonist, βARm23 was as stable as bovine rhodopsin. In addition, βAR-m23 was significantly more stable in a wide range of detergents ideal for crystallisation and was preferentially in an antagonist conformation in the absence of ligand.

Results

Selection of Single Mutations that Increase the Thermostability of the β1 Adrenergic Receptor βAR from turkey erythrocytes is an ideal target for structural studies because it is well characterised and is expressed at high-levels in insect cells using the baculovirus expression system[10,11]. The best overexpression of βAR is obtained using a truncated version of the receptor containing residues 34-424 (βAR$_{34-424}$) [9] and this was used as the starting point for this work. Alanine scanning mutagenesis was used to define amino residues in βAR$_{34-424}$ that, when mutated, altered the thermostability of the receptor; if an alanine was present in the sequence it was mutated to a leucine residue. A total of 318 mutations were made to amino acid residues 37-369, a region that encompasses all seven transmembrane domains and 23 amino acid residues at the C terminus; mutations at 15 amino residues were not obtained due to strong secondary structure in the DNA template. After sequencing each mutant to ensure the presence of only the desired mutation, the receptors were functionally expressed in E. coli and assayed for stability.

The assay for thermostability was performed on unpurified detergent-solubilised receptors by heating the receptors at 32° C. for 30 minutes, quenching the reaction on ice and then performing a radioligand binding assay, using the antagonist [$^3$H]-dihydroalprenolol, to determine the number of remaining functional βAR$_{34-424}$ molecules compared to the unheated control. Heating the unmutated βAR$_{34-424}$ at 32° C. for 30 min before the assay reduced binding to approximately 50% of the unheated control (FIG. 7); all the data for the mutants were normalised by including the unmutated βAR$_{34-424}$ as a control in every assay performed. In the first round of screening, eighteen mutants showed an apparent increase in stability, maintaining more than 75% of antagonist binding after heating and being expressed in E. coli to at least 50% of the native βAR$_{34-424}$ levels. In view of the possibility of increasing further the stability of these mutants, each of the 18 residues was mutated to 2-5 alternative amino acid residues of varying size or charge (FIG. 1). Out of these 18 mutants, 12 were not improved by further changes, 5 had better thermostability if another amino acid was present and one mutation from the first screen turned out to be a false positive. In addition, three residues that were not stabilised upon mutation to alanine (V89, S151, L221) were mutated to a range of other amino acid residues; the two positions that when mutated to alanine did not affect thermostability, were also unaffected by other changes. In contrast, V89 showed less thermostability when mutated to alanine, but thermostability increased when it was mutated to Leu. Thus the initial alanine scanning successfully gave two-thirds of the best amino acid residues of those tested for any given position.

The position and environment predicted for each of the 16 amino residues that gave the best increases in thermostability when mutated were determined by aligning the βAR sequence with that of rhodopsin whose structure is known (FIG. 2). Fourteen of these residues were predicted to be present in transmembrane α-helices, with five of the residues predicted to be lipid-facing, 4 being deeply buried and the remainder were predicted to be at the interfaces between the helices. Some of these residues would be expected to interact with each other in the βAR structure, such as the consecutive amino acids G67 and R68 (V63 and Q64 in rhodopsin), or the amino acids within the cluster Y227, R229, V230 and A234 in helix 5 (Y223, Q225, L226 and V230 in rhodopsin). Other amino acid residues that could interact in βAR were Q194A in external loop 2 and D322A in external loop 3 (G182 and P285 in rhodopsin, respectively).

The increase in stability that each individual mutation gave to βAR$_{34-424}$ was determined by measuring the Tm for each mutant (results not shown); Tm in this context is the temperature that gave a 50% decrease in functional binding after heating the receptor for 30 minutes. Each mutation increased the Tm of βAR$_{34-424}$ by 1-3° C., with the exception of M90A and Y227A that increased the Tm by 8° C.

Combining Mutations to Make an Optimally Stable Receptor

Initially, mutations that improved thermostability that were adjacent to one another in the primary amino sequence of βAR were combined. Constructions containing the mutations G67A and R68S, or different combinations of the mutations at the end of helix 5 (Y227A, R229Q, V230A and A234L) were expressed and assayed; the Tm values (results not shown) were only 1-3° C. higher than the Tm for βAR$_{34-424}$ and one mutant was actually slightly less stable, suggesting that combining mutations that are adjacent to one another in the primary amino acid sequence does not greatly improve thermostability. Subsequently, mutations predicted to be distant from one another in the structure were combined. PCR reactions were performed using various mixes of primers to combine up to 5 different mutations in a random manner and then tested for thermostability (Table 1). The best of these combinations increased the Tm more than 10° C. compared to the Tm of βAR$_{34-424}$. In some cases, there was a clear additive effect upon the Tm with the sequential incorporation of individual mutations. This is seen in a series of 3 mutants, m4-1, m4-7 and m4-2, with the addition of V230A to m4-1 increasing the Tm by 2° C. and the additional mutation D332A in m4-7 increasing the Tm a further 3° C. Mutants that contained Y227A and M90A all showed an increase in Tm of 10° C. or more. Just these two mutations together increased the Tm of βAR$_{34-424}$ by 13° C. (m7-5), however, the total antagonist binding was less than 50% of βAR$_{34-424}$ suggesting impaired expression of this mutant. The addition of F338M to m7-5 did not increase the thermostability, but it increased levels of functional expression in E. coli.

TABLE 1

Combinations of mutations by PCR.

| PCR | Receptor | Mutations | $T_m$ (° C.) |
|---|---|---|---|
|  | βAR$_{34-424}$ |  | 31.7 ± 0.1 |
| 4 | m4-1 | G67A, G98A | 35.5 ± 0.9 |
|  | m4-2 | G67A, G98A, V230A, D322A | 40.9 ± 0.9 |
|  | m4-6 | G98A, D322A | 35.0 ± 0.2 |
|  | m4-7 | G67A, G98A, V230A | 38.0 ± 1.2 |
| 6 | m6-1 | Y227A, A234L, A282L, A334L | 41.6 ± 0.9 |
|  | m6-4 | R68S, Y227A, A234L, A282L | 41.6 ± 0.1 |
|  | m6-5 | R68S, A234L, A282L, A334L | 41.9 ± 0.5 |
|  | m6-9 | R68S, Y227A, A234L, A282L, A334L | 43.7 ± 0.4 |
|  | m6-10 | R68S, Y227A, A282L, A334L | 47.4 ± 1.1 |
|  | m6-11 | R68S, A282L, A334L | 39.1 ± 0.5 |
| 7 | m7-1 | M90V, A282L, F338M | 43.0 ± 0.8 |
|  | m7-2 | M90V, A282L | 38.9 ± 0.6 |
|  | m7-5 | M90V, Y227A | 45.2 ± 1.0 |
|  | m7-6 | M90V, I129V | 40.0 ± 0.6 |
|  | m7-7 | M90V, Y227A, F338M | 45.2 ± 2.0 |
| 10 | m10-4 | R68S, M90V, V230A, A334L | 46.9 ± 1.0 |
|  | m10-8 | R68S, M90V, V230A, F327A, A334L | 47.3 ± 1.4 |

10 PCR reactions were performed combining different pairs of primers that contained the selected mutations. Successful PCR reactions are shown in the table. The stability of these new mutants was assayed as described in FIG. 7 and the Tm calculated. The results are shown as the mean ± S.E. from duplicates.

The most thermostable mutants obtained, which were still expressed at high levels in E. coli, were m6-10, m7-7 and m10-8. These mutants contained collectively a total of 10 different mutations, with 8 mutations occurring in at least two of the mutants. A second round of mutagenesis was performed using m10-8 as the template and adding or replacing mutations present in m6-10 and m7-7 (FIG. 3); some of these mutations were very close in the primary amino acid sequence of βAR and therefore were not additive as noted above, but many mutations improved the Tm further (Table 2). For example, exchanging two mutations in m10-8, to create m18, raised the Tm to 49.6° C. and adding A282L to make m23 increased the Tm a further 3° C. to 52.8° C. This produced the most thermostable βAR$_{34-424}$ mutant so far and will be referred to as βAR-m23.

TABLE 2

Improvement of best combination of mutations. These new mutants were obtained mixing the changes present in mutants m6-10, m7-7 and m10-8 by PCR. The stability of these new mutants was assayed as described in FIG. 7 and the Tm calculated. The results are shown as the mean ± S.E. from duplicates.

| | Mutations | | | | | | | | $T_m$ (° C.) |
|---|---|---|---|---|---|---|---|---|---|
| m17 | R68S | M90V | Y227A | V230A | — | F327A | A334L | — | 48.2 ± 1.4 |
| m18 | R68S | M90V | Y227A | V230A | A282L | F327A | — | F338M | 49.6 ± 0/9 |
| m19 | R68S | M90V | Y227A | — | A282L | F327A | — | F338M | 49.0 ± 0.8 |
| m20 | R68S | M90V | — | — | — | F327A | A334L | — | 48.4 ± 0.7 |
| m21 | R68S | M90V | Y227A | — | — | F327A | A334L | — | 47.0 ± 1.3 |
| m22 | R68S | M90V | Y227A | | | F327A | A334L | — | 47.4 ± 0.5 |
| m23 | R68S | M90V | Y227A | — | A282L | F327A | — | F338M | 52.8 ± 1.4 |

The thermostability assays used to develop βAR$_{34-424}$ mutants were performed by heating the receptor in the absence of the antagonist, but it is well known that bound ligand stabilises receptors. Therefore, stability assays for βAR$_{34-424}$ and βAR-m23 were repeated with antagonist bound to the receptors during the heating step (FIG. 4).

As expected, the Tm of the receptor that contained bound antagonist during the incubation was higher than that for the receptor without antagonist. For βAR$_{34-424}$ the Tm was 6° C. higher with bound antagonist and for βAR-m23 the Tm increased 2° C. to 55° C.; the smaller increase in thermostability observed for βAR-m23 when antagonist binds suggests that the receptor is already in a more stable conformation similar to the antagonist bound state than βAR$_{34-424}$ (see also below). The Tm of βAR-m23 with antagonist bound is very similar to the Tm of dark-state rhodopsin in dodecylmaltoside (DDM)[12], whose structure has been solved by two independent laboratories[13,14]. This suggested that βAR-m23 is sufficiently stable for crystallisation.

Characterization of βAR-m23

The three characteristic activities measured for βAR-m23 and βAR$_{34-424}$ to identify the effect of the six mutations were the affinity of antagonist binding, the relative efficacies of agonist binding and the ability of βAR-m23 to couple to G proteins. Saturation binding experiments to membranes using the antagonist [$^3$H]-dihydroalprenolol (FIG. 8) showed that the affinity of binding to βAR-m23 ($K_D$ 6.5±0.2 nM, n=2) was slightly lower than for βAR$_{34-424}$ ($K_D$ 2.8±0.1 nM, n=2), suggesting that there are no large perturbations in the structure of βARm23 in the antagonist-bound conformation. This is consistent with the observation that none of the mutations in βAR-m23 correspond with amino acids believed to be implicated in ligand binding. In contrast to antagonist binding, the efficacy of agonist binding by βAR-m23 is 3 orders of magnitude weaker than for βAR$_{34-424}$ (FIG. 5). The potency of the agonist isoprenaline is consistently lower in βAR-m23 and βAR$_{34-424}$ than for the native agonist norepinephrine, indicating that the agonist-bound conformation for the two receptors is likely to be similar. However, the large decrease in agonist efficacy in βAR-m23 compared to βAR$_{34-424}$ indicates that the 6 mutations in βAR-m23 have locked the receptor preferentially in an antagonist-bound conformation. From a crystallisation perspective, this is an added bonus to thermostabilisation, because it is essential to have a conformationally homogeneous protein population for the production of diffraction-quality crystals.

All of the thermostability assays used to derive βAR-m23 were performed on receptors solubilised in DDM. The aim of the thermostabilisation process was to produce a receptor that is ideal for crystallography, which means being stable in a variety of different detergents and not just DDM. We therefore tested the stability of βAR-m23 and βAR in a variety of different detergents, concentrating on small detergents that are preferentially used in crystallising integral membrane proteins.

Membranes prepared from *E. coli* expressing βAR-m23 or βAR$_{34-424}$ were solubilised in DDM, bound to Ni-NTA agarose then washed with either DDM, decylmaltoside (DM), octylglucoside (OG), lauryldimethylamine oxide (LDAO) or nonylglucoside (NG). Stability assays were performed on the receptors in each of the different detergents (FIG. 6). βAR$_{34-424}$ was only stable in DDM and DM, with no active receptors eluting from the resin washed with OG, NG or LDAO. In contrast, functional βAR-m23 was still present in all detergents and the Tm could be determined. As expected, the smaller detergents were considerably more denaturing than either DDM (Tm 52° C.) or DM (Tm 48° C.), with $T_m$s of 25° C. (NG), 23° C. (LDAO) and 17° C. (OG). The difference in Tm between βAR-m23 and βAR$_{34-424}$ is about 20° C., irrespective of whether the receptors were solubilised in either DDM or DM; it is therefore not surprising that no active βAR$_{34-424}$ could be found in even NG, because the predicted Tm would be about 5° C., thus resulting in rapid inactivation of the receptor under the conditions used for purification. The selection strategy used for the generation of βAR-m23 was chosen deliberately to be based upon thermostability, because it is far simpler to apply than selecting for stability in detergents of increasing harshness. However, it is clear that increasing the thermostability of βAR$_{34-424}$ also resulted in increasing tolerance to small detergents ideal for crystallising integral membrane proteins.

Crystallisation of Mutant GPCR

Earlier attempts to crystallise several different constructs of turkey beta-adrenegic receptor failed. Despite experimenting with a variety of conditions, using both the native sequence and several truncated and loop-deleted constructs, over many years, no crystals were obtained.

However, once the stabilising mutations from βAR-m23 were transferred into the constructs, several different crystals were obtained in different detergents and different conditions.

The crystals that have been most studied so far were obtained using the purified beta-36 construct (amino acid residues 34-367 of the turkey beta receptor containing the following changes: point mutations C116L and C358A; the 6 thermostabilising point mutations in m23; replacement of amino acid residues 244-278 with the sequence ASKRK; a C terminal His6 tag) expressed in insect cells using the baculovirus expression system, after transferring the receptor into the detergent octyl-thioglucoside. The precipitant used was PEG600 or PEG1000 and the crystals obtained are elongated plates.

Experiments have also been carried out to see whether, once the crystallisation conditions had been defined using the stabilised receptor, it was possible to get crystals using the original non-stabilised construct. It was possible that similar or perhaps very small crystals could have been obtained, but, in fact, the "wild type" (i.e. the starting structure from which the mutagenesis began) never gave any crystals.

The crystals are plate-shaped with space group C2 and diffract well, though the cell dimensions do vary depending on the freezing conditions used.

In general, once a GPCR has been stabilised it may be subjected to a variety of well-known techniques for structure determination. The most common technique for crystallising membrane proteins is by vapour diffusion (20, 21), usually using initially a few thousand crystallisation conditions set up using commercial robotic devices (22). However, sometimes the crystals formed by vapour diffusion are small and disordered, so additional techniques may then be employed. One technique involves the co-crystallisation (by vapour diffusion) of the membrane protein with antibodies that bind specifically to conformational epitopes on the proteins' surface (23, 24); this increases the hydrophilic surface of the protein and can form strong crystal contacts. A second alternative is to use a different crystallisation matrix that is commonly called either lipidic cubic phase or lipidic mesophase (25, 26), which has also been developed into a robotic platform (27). This has proven very successful for producing high quality crystals of proteins with only small hydrophilic surfaces e.g. bacteriorhodopsin (28). Membrane protein structures can also be determined to high-resolution by electron crystallography (29).

The evolution of βAR-m23 from βAR$_{34-424}$ by a combination of alanine scanning mutagenesis and the selection of thermostable mutants has resulted in a GPCR that is ideal for crystallography. The Tm for βAR-m23 is 21° C. higher than for βAR$_{34-424}$ and, in the presence of antagonist, βAR-m23 has a similar stability to rhodopsin. The increased Tm of βAR-m23 has resulted in an increased stability in a variety of small detergents that inactivate βAR$_{34-424}$. In addition, the selection strategy employed resulted in a receptor that is preferentially in the antagonist-bound conformation, which will also improve the chances of obtaining crystals, because the population of receptor conformations will be more homogeneous than for wild type βAR$_{34-424}$. Thus we have achieved a process of conformational stabilisation in a single selection procedure.

It is not at all clear why the particular mutations we have introduced lead to the thermostabilisation of the receptor. Equivalent positions in rhodopsin suggest that the amino acid residues mutated could be pointing into the lipid bilayer, into the centre of the receptor or at the interfaces between these two environments. Given the difficulties in trying to understand the complexities of the thermostabilisation of soluble proteins[15], it seems unlikely that membrane proteins will be any easier to comprehend; we found that there was no particular pattern in the amino acid residues in βAR that, when mutated, led to thermostability. However, since nearly 5% of the mutants produced were more stable than the native receptor, alanine scanning mutagenesis represents an efficient strategy to rapidly identify thermostable mutants.

The procedure we have used to generate βAR-m23 is equally applicable to any membrane protein that has a convenient assay for detecting activity in the detergent solubilized form. While we have selected for stability as a function of temperature as the most convenient primary parameter, the procedure can easily be extended to test primarily for stability, for example, in a harsh detergent, an extreme of pH or in the presence of chaotropic salts. Conformational stabilisation of a variety of human receptors, channels and transporters will make them far more amenable to crystallography and will also allow the improvement in resolution of membrane proteins that have already been crystallised. It is to be hoped that conformational stabilisation will allow membrane protein crystallisation to become a far more tractable problem with a greater probability of rapid success than is currently the case. This should allow routine crystallisation of human membrane proteins in the pharmaceutical industry, resulting in valuable structural insights into drug development.

Methods

Materials. The truncated β1 adrenergic receptor from turkey (βAR$_{34-424}$)[9] was kindly provided by Dr Tony Warne (MRC Laboratory of Molecular Biology, Cambridge, UK). This βAR construct encoding residues 34-424 contains the mutation C116L to improve expression[11], and a C-terminal tag of 10 histidines for purification. 1-[4,6-propyl-$^3$H]-dihydroalprenolol ([$^3$H]-DHA) was supplied by Amersham Bioscience, (+) L-norepinephrine bitartrate salt, (−) isoprenaline hydrochloride, (−) alprenolol tartrate salt and s-propranolol hydrochloride were from Sigma.

Mutagenesis of DAR. The βAR cDNA was ligated into pRGIII to allow the functional expression of βAR in *E. coli* as a MalE fusion protein[16]. Mutants were generated by PCR using the expression plasmid as template using the QuikChange II methodology (Stratagene). PCR reactions were transformed into XL10-Gold ultracompetent cells (Stratagene) and individual clones were fully sequenced to check that only the desired mutation was present. Different mutations were combined randomly by PCR by including all the pairs of primers that introduced the following mutations: Mut4, G67A, G068A, V230A, D322A and F327A; Mut6, R068S, Y227A, A234L, A282L and A334L; Mut7, M90V, I129V, Y227A, A282L and F338M; Mut10, R68S, M90V, V230A, F327A and A334L. The PCR mixes were transformed and the clones sequenced to determine exactly which mutations were introduced.

Protein expression and membrane preparations. Expression of βAR and the mutants was performed in XL10 cells (Stratagene). Cultures of 50 ml of 2×TY medium containing ampicillin (100 µg/ml) were grown at 37° C. with shaking until OD$_{600}$=3 and then induced with 0.4 mM IPTG. Induced cultures were incubated at 25° C. for 4 h and then cells were harvested by centrifugation at 13,000×g for 1 min (aliquots of 2 ml) and stored at −20° C. For the assays, cells were broken by freeze-thaw (five cycles), resuspended in 500 pa of buffer [20 mM Tris pH 8, 0.4 M NaCl, 1 mM EDTA and protease inhibitors (Complete™, Roche)]. After an incubation for 1 h at 4° C. with 100 µg/ml lysozyme and DNase I (Sigma), samples were solubilized with 2% DDM on ice for 30 minutes. Insoluble material was removed by centrifugation (15,000×g, 2 min, 4° C.) and the supernatant was used directly in radioligand binding assays.

For large-scale membrane preparations, 2L and 6L of *E. coli* culture of βAR and Mut23, respectively, were grown as described above. Cells were harvested by centrifugation at 5,000×g for 20 min, frozen in liquid nitrogen and stored at −80° C. Pellets were resuspended in 10 ml of 20 mM Tris pH 7.5 containing 1× protease inhibitor cocktail (Complete™ EDTA-free, Roche); 1 mg DNase I (Sigma) was added and the final volume was made to 100 ml. Cells were broken by a French press (2 passages, 20,000 psi), and centrifuged at 12,000×g for 45 min at 4° C. to remove cell debris. The supernatant (membranes) was centrifuged at 200,000×g for 30 min at 4° C.; the membrane pellet was resuspended in 15 ml of 20 mM Tris pH 7.5 and stored in 1 ml aliquots at −80° C. after flash-freezing in liquid nitrogen. The protein concentration was determined by the amido black method[17]. These samples were used in radioligand binding assays after thawing and being solubilized in 2% DDM as above.

For competition assays, as well as testing different detergents, DDM-solubilized βAR was partially purified with Ni-NTA agarose (Qiagen). 200 µl of Ni-NTA agarose was added to 2 ml of solubilized samples (10 mg/ml of membrane protein) in 20 mM Tris pH 8, 0.4 M NaCl, 20 mM imidazole pH 8 and incubated for 1 h at 4° C. After incubation, samples were centrifuged at 13,000×g for 30 sec and washed twice with 250 µl of buffer (20 mM Tris pH 8, 0.4 M NaCl, 20 mM imidazole) containing detergent (either 0.1% DDM, 0.1% DM, 0.1% LDAO, 0.3% NG or 0.7% OG).

Receptors were eluted in 2×100 µl of buffer (0.4 M NaCl, 1 mM EDTA, 250 mM imidazole pH 8, plus the relevant detergent). The K$_D$ for [$^3$H]-DHA binding to semipurified βAR$_{34-424}$ and βAR-m23 was, respectively 3.7 nM and 12.5 nM and the final concentration of [$^3$H]-DHA used in the competition assays was 3 times the K$_D$ ie 12 nM for βAR$_{34-424}$ and 40 nM for βAR-m23.

Radioligand binding and thermostability assays. Single point binding assays contained 20 mM Tris pH 8, 0.4 M NaCl, 1 mM EDTA, 0.1% DDM (or corresponding detergent) with 50 nM [$^3$H]-DHA and 20-100 µg membrane protein in a final volume of 120 µl; equilibration was for 1 h at 4° C. Thermostability was assessed by incubating the binding assay mix, with or without [$^3$H]-DHA at the specified temperature for 30 minutes; reactions were placed on ice and [$^3$H]-DHA added as necessary and equilibrated for a further hour. Receptor-bound and free radioligand were separated by gel filtration as described previously[18]. Non-specific binding was determined in the presence of 1 µM of s-propranolol. Saturation curves were obtained using a range of [$^3$H]-DHA concentration from 0.4 nM to 100 nM. Competition assays were performed using a concentration of [$^3$H]-DHA of 12 nM for βAR$_{34-424}$ and 40 nM for βAR-m23 (ie three times the $K_D$) and various concentrations of unlabeled ligands (0-100 mM). Radioactivity was counted on a Beckman LS6000 liquid scintillation counter and data were analyzed by nonlinear regression using Prism software (GraphPad).

Location of βAR-m23 thermostable mutations in rhodopsin structure. The pdb file for the rhodopsin structure, accession code 1GZM[14], was downloaded from the Protein Data Bank website (www.pdb.org) and displayed in the program PyMOLX11Hybrid (DeLano Scientific). The equivalent amino acid residues in rhodopsin for the thermostable mutations in βAR were located in the rhodopsin structure based upon an alignment among the four GPCRs with which we are most familiar, namely rhodopsin, β1 adrenergic receptor, neurotensin receptor and adenosine A$_{2a}$ receptor[19].

EXAMPLE 2

Mutants of the Adenosine A$_{2a}$ Receptor (A$_{2a}$R) with Increased Thermostability 1. 315 site-directed mutants made between residues 2-316 of A$_{2a}$R.
2. All of these mutants have been assayed for thermostability using an assay measuring agonist and antagonist binding after the heating step (Ligand(-) format as described in FIG. 12).
   a. 26 mutants showed improved thermostability when measured with $^3$H-NECA (agonist): G114 A, G118A, L167A, A184L, R199A, A203L, L208A, Q210A, S213A, E219A, R220A, S223A, T224A, Q226A, K227A, H230A, L241A, P260A, S263A, L267A, L272A, T279A, N284A, Q311A, P313A, K315A.
   b. 18 mutants showed improved thermostability when assayed with $^3$H-ZM241385 (antagonist): A54L, V57A, H75A, T88A, G114A, G118A, T119A, K122A, G123A, P149A, E151A, G152A, A203L, A204L, A231L, L235A, V239A.
3. Mutations have been combined to generate mutants in a putative antagonist conformation. Wildtype A$_{2a}$R has a Tm of 31° C. with ZM241385 bound.
   a. Rant17 A54L+K122A+L235A Tm 48° C. (ZM241385 bound)
   b. Rant19 A54L, T88A, V239A+A204L Tm 47° C. (ZM241385 bound)
   c. Rant21 A54L, T88A, V239A+K122A Tm 49° C. (ZM241385 bound)
4. Mutations from the agonist screen have been combined, but have led to only a very low level of improvement in Tm of +2° C.

Table (i) in FIG. 29 provides a list of A2aR stabilising mutations.

TABLE (ii)

Stability of best combinations.

| | Tm (° C.) | | | Tm (° C.) | |
|---|---|---|---|---|---|
| | − agonist | + agonist | | − antagonist | + antagonist |
| Wt | 21 | 29 | wt | 31 | 32 |
| Rag 1 (A184L/R199A/ L272A) | 26 | 34 | Rant 5 (A54L/T88A/ V239A) | 42 | 46 |
| Rag 23 (Rag 1 + F79A/ L208A) | 22 | 38 | Rant 21 (Rant 5 + K122A) | 41 | 49 |

Receptors were solubilised in 1% DDM (no glycerol). A melting profile was obtained by heating the solubilised receptor at different temperatures in absence (apo-state) or presence of ligand (ligand-occupied state). Data shown are representative of at least three independent experiments. S.D. is <1° C.

TABLE (iii)

Summary of results for competition assays of detergent-solubilised wild-type A2aR and thermo-stable mutant Rant 21.

| | $K_i$ (M) | |
|---|---|---|
| Competitor | wt | Rant 21 |
| XAC | 2.3 × 10$^{-6}$ | 2.3 × 10$^{-6}$ |
| Theophylline | 1.5 × 10$^{-3}$ | 0.9 × 10$^{-3}$ |
| NECA | 7.0 × 10$^{-6}$ | >1 × 10$^{-1}$ |
| R-PIA | 1.6 × 10$^{-5}$ | 3.6 × 10$^{-3}$ |

Values are representative of two independent experiments.
Each data point was assayed in triplicate and plotted as mean ± SD. Each solubilised receptor was incubated with ligands for one hour on ice in binding buffer (50 mM Tris pH 7.5 and 0.025% DDM) containing 400 mM NaCl.
Binding of [3H]ZM241385 (10 nM) in the absence of unlabeled ligand was set to 100%. Data shown are from two independent experiments with each data point measured in triplicate.
Incubation of samples with ligands was for 1 hour on ice with [$^3$H]ZM241385 at a concentration of 10 nM. $K_i$ values were calculated according to the Cheng and Prusoff equation using the non-linear regression equation of the software Prism, applying a $K_D$ for [$^3$H]ZM241385 of 12 nM for the wild-type and 15 nM for Rant 21.
Rant 21 did not bind NECA sufficiently for an accurate $K_i$ determination (hence indicated as >1 × 10$^{-1}$). The affinity of Rant21 for agonist binding is weakened 232 fold for R-PIA and at least by 1900 fold for NECA.

TABLE (iv)

Summary of results for saturation assays of detergent-solubilised wild-type A2aR and thermo-stable mutants.

| | $K_D$ (nM) | |
|---|---|---|
| Receptor | [$^3$H]NECA (agonist) | [$^3$H]ZM241385 (antagonist) |
| wt | 32 ± 1 | 12 ± 3 |
| Rag 1 | 26 ± 0.4 | 26 ± 0.5 |
| Rag 23 | 21 ± 1 | 62 ± 1 |
| Rant 21 | >450 | 15 ± 3 |

Values are representative of three independent experiments. Each data point was assayed in triplicate and plotted as mean ± SD. Data were fitted to the Michaelis-Menten equation using the non-linear regression equation of the software Prism.

TABLE (v)

Summary of stability of wild-type and mutant receptors in different detergents.

| | Tm (° C.) | | | |
|---|---|---|---|---|
| | Agonist-binding | | Antagonist-binding | |
| | wt | Rag 23 | wt | Rant 21 |
| 0.01% DDM | 27 | 34 | 25 | 39 |
| 0.1% DM | 23 | 29 | 10 | 28 |
| 0.3% NM | 22 | 28 | <4 | 25 |
| 0.3% NG | † | † | † | 22 |
| 0.6% OG | <9 | 16 | † | 23 |
| 0.003% LDAO | 28 | 38 | 32 | 42 |
| 0.006% FC12 | 37 | 39 | 43 | 49 |

Solubilisation of receptors and detergent exchange was performed during the IMAC step.
S.D. is <1° C.
It was not possible to determine the Tm for some receptor-detergent combinations, because the receptor was too unstable (†).

EXAMPLE 3

Mutants of the Neurotensin Receptor (NTR) with Increased Thermostability 1. 340 site-directed mutants have been made between residues 61-400 of NTR.
2. Initially, all of these mutants were assayed for thermostability using an assay measuring $^3$H-neurotensin (agonist) binding after the heating step. 24 mutations led to a small but significant increase in thermostability: A356L, H103A, D345A, A86L, A385L, Y349A, C386A, K397A, H393A, I116A, F358A, S108A, M181A, R392A, D113A, G209A, L205A, L72A, A120L, P399A, Y351A, V268A, T207A, A155L, S362A, F189A, N262A, L109A, W391A, T179A, S182A, M293A, L256A, F147A, D139A, S100A, K176A, L111A, A90L, N270A.
3. Mutants tested for thermostability by heating in the absence of the agonist were re-tested using a slightly different assay where the mutants were heated in the presence of $^3$H-neurotensin (Ligand(+) format in FIG. 12). Mutants with improved thermostability are: A69L, A73L, A86L, A90L, H103A, V165A, E166A, G215A, V229A, M250A, I253A, A177L, R183A, I260A, T279A, T294A, G306A, L308A, V309A, L310A, V313A, F342A, F358A, V360A, S362A, N370A, S373A, F380A, A385L, P389A, G390A, R395A.
4. There are also mutants that have a significantly enhanced expression level compared to the wildtype receptor and could be used to boost preceptor production levels for crystallisation: A86L, H103A, F358A, S362A, N370A, A385L, G390A. All of these also have increased thermostability.
5. Preferred combinations are
   a. Nag7m F358A+A86L+I260A+F342A Tm 51° C. (neurotensin bound)
   b. Nag7n F358A+H103A+I260A+F342A Tm 51° C. (neurotensin bound) Wildtype NTR has a Tm of 35° C. with neurotensin bound.

EXAMPLE 4

Identification of Structural Motifs in which Stabilising GPCR Mutations Reside

The structure of the β2 adrenergic receptor has been determined (20, 21), which is 59% identical to the turkey β1 receptor, but with a distinctly different pharmacological profile (22, 23). In order to determine the structural motifs in which the stabilising mutations of the turkey β1 receptor reside, we mapped the mutations onto the human β2 structure (21).

The beta adrenergic receptors were first aligned using ClustalW in the MacVector package; thermostabilising mutations in turkey β1 were highlighted along with the corresponding residue in the human β2 sequence. The human β2 model (pdb accession code 2RH1) was visualised in Pymol and the desired amino acids were shown as space filling models by standard procedures known in the art. The structural motifs in which the stabilising mutations were located, were determined by visual inspection.

Table (vi) lists the equivalent positions in the β2 receptor corresponding to the thermostabilising mutations in βAR-m23 and the structural motifs in which they reside.

As seen from Table (vi), the mutations are positioned in a number of distinct localities. Three mutations are in loop regions that are predicted to be accessible to aqueous solvent (loop). Eight mutations are in the transmembrane α-helices and point into the lipid bilayer (lipid); three of these mutations are near the end of the helices and may be considered to be at the hydrophilic boundary layer (lipid boundary). Eight mutations are found at the interfaces between transmembrane α-helices (helix-helix interface), three of which are either within a kinked or distorted region of the helix (kink) and another two mutations occur in one helix but are adjacent to one or more other helices which contain a kink adjacent in space to the mutated residue (opposite kink). These latter mutations could affect the packing of the amino acids within the kinked region, which could result in thermostabilisation. Another mutation is in a substrate binding pocket. (pocket).

TABLE (vi)

Position in the human β2 structure of the amino acid residues equivalent to the thermostabilising mutations found in the turkey β1 receptor and the structural motifs in which they reside.

| | Turkey β1 | Human β2 | Description | |
|---|---|---|---|---|
| Helix 1 | I55A | I47 | 3-helix kink interface | FIG. 18 |
| Helix 1 | G67A | A59 | lipid boundary | |
| Helix 1 | R68S | K60 | lipid boundary | FIG. 25 |
| Helix 2 | V89L | V81 | kink | FIG. 19 |
| Helix 2 | M90V | M82 | kink | FIG. 20 |
| Helix 2 | G98A | G90 | pocket | |
| Helix 3 | I129V | I121 | opposite kink | FIG. 21 |
| | S151E | S143 | loop | |
| Helix 4 | V160A | V152 | lipid | |
| | Q194A | A186 | loop | |
| Helix 5 | L221V | V213 | lipid | |
| Helix 5 | Y227A | Y219 | helix-helix interface | FIG. 23 |
| Helix 5 | R229Q | R221 | lipid | |
| Helix 5 | V230A | V222 | helix-helix interface | |
| Helix 5 | A234L | A226 | helix-helix interface | |
| Helix 6 | A282L | C265 | loop | FIG. 24 |
| | D322A | K305 | lipid boundary | |
| Helix 7 | F327A | L310 | lipid | |
| Helix 7 | A334L | V317 | lipid | |
| Helix 7 | F338M | F321 | kink | FIG. 22 |

Such structural motifs, by virtue of them containing stabilising mutations, are important in determining protein stability. Therefore, targeting mutations to these motifs will facilitate the generation of stabilised mutant GPCRs. Indeed, there were several instances where more than one mutation mapped to the same structural motif. For example, the Y227A, V230A and A234L mutations in the turkey β1 adrenergic receptor all mapped to the same helical interface, the V89L and M90V mutations mapped to the same helical kink and the F327A and A334L mutations mapped to the same helical surface pointing towards the lipid bilayer (Table (vi)). Thus, when one stabilising mutation has been identified, the determination of the structural motif in which that mutation is located will enable the identification of further stabilising mutations.

REFERENCES

1. S. H. White (2004) *Protein Sci* 13, 1948-1949.
2. C. G. Tate (2001) *FEBS Lett* 504, 94-98.
3. R. Grisshammer, C. G. Tate (1995) *Q Rev Biophys* 28, 315-422.
4. J. U. Bowie (2001) *Curr Opin Struct Biol* 11, 397-402.
5. F. W. Lau, S. Nauli, Y. Zhou, J. U. Bowie (1999) *J Mol Biol* 290, 559-564.
6. Y. Zhou, J. U. Bowie (2000) *J Biol Chem* 275, 6975-6979.
7. S. Faham, D. Yang, E. Bare, S. Yohannan, J. P. Whitelegge, J. U. Bowie (2004) *J Mol Biol* 335, 297-305.
8. Y. Yarden, H. Rodriguez, S. K. Wong, D. R. Brandt, D. C. May, J. Burnier, R. N. Harkins, E. Y. Chen, J. Ramachandran, A. Ullrich, et al (1986) *Proc. Natl. Acad. Sci. USA* 83, 6795-6799.
9. T. Warne, J. Chirnside, G. F. Schertler (2003) *Biochim Biophys Acta* 1610, 133-140.
10. E. M. Parker, E. M. Ross (1991) *J Biol Chem* 266, 9987-9996.
11. E. M. Parker, K. Kameyama, T. Higashijima, E. M. Ross (1991) *J Biol Chem* 266, 519-527.
12. W. J. Degrip (1982) *Methods in Enzymology* 81, 256-265.
13. K. Palczewski, T. Kumasaka, T. Hori, C. A. Behnke, H. Motoshima, B. A. Fox, I. Le Trong, D. C. Teller, T. Okada, R. E. Stenkamp, et al (2000) *Science* 289, 739-745.
14. J. Li, P. C. Edwards, M. Burghammer, C. Villa, G. F. Schertler (2004) *J Mol Biol* 343, 1409-1438.
15. R. Jaenicke, G. Bohm (1998) *Current Opinion in Structural Biology* 8, 738-748.
16. J. Tucker, R. Grisshammer (1996) *Biochem J* 317 (Pt 3), 891-899.
17. W. Schaffner, C. Weissmann (1973) *Anal. Biochem.* 56, 502-514.
18. C. G. Tate (1998) *Methods Enzymol* 296, 443-455.
19. H. M. Weiss, R. Grisshammer (2002) *Eur J Biochem* 269, 82-92.
20. Rasmussen, S. G., Choi, H. J., Rosenbaum, D. M., Kobilka, T. S., Thian, F. S., Edwards, P. C., Burghammer, M., Ratnala, V. R., Sanishvili, R., Fischetti, R. F., Schertler, G. F., Weis, W. I. and Kobilka, B. K. (2007) *Nature* 15, 383-387.
21. Cherezov, V., Rosenbaum, D. M., Hanson, M. A., Rasmussen, S. G., Thian, F. S., Kobilka, T. S., Choi, H. J., Kuhn, P., Weis, W. I., Kobilka, B. K. and Stevens, R. C. (2007) *Science* 318:1258-1265.
22. Minneman, K. P., Weiland, G. A. and Molinoff, P. B. (1980) *Mol Pharmacol* 17:1-7.
23. Parker, E. M., Swigart, P., Nunnally, M. H., Perkins, J. P. and Ross, E. M. (1995) *J Biol Chem* 270:6482-6487.

The invention claimed is:

1. A mutant GPCR wherein (i) the mutant GPCR is a mutant β-adrenergic receptor which, when compared to the corresponding wild-type adrenergic receptor, has increased conformational thermostability and has at least one amino acid replacement at a position which corresponds to any of the following positions according to the turkey β-adrenergic receptor defined as SEQ ID NO: 1: G67A, G98A, V230A, D322A, Y227A, A234L, A282L, A334L, R68S, M90V, F338M, I129V, V230A, or F327A; or wherein (ii) the mutant GPCR is a mutant adenosine receptor which, when compared to the corresponding wild-type adenosine receptor, has increased conformational stability and has at least one amino acid replacement at a position which corresponds to any of the following positions according to the human adenosine A2a receptor defined as SEQ ID NO: 5: G114A, G118A, L167A, A184L, R199A, A203L, L208A, Q210A, S213A, E219A, R220A, S223A, T224A, Q226A, K227A, H230A, L241A, P260A, S263A, L267A, L272A, T279A, N284A, Q311A, P313A, or K315A; or wherein (iii) the mutant GPCR is a mutant neurotensin receptor which, when compared to the corresponding wild-type neurotensin receptor, has increased conformational thermostability and has at least one amino acid replacement at a position which corresponds to any of the following positions according to the rat neurotensin receptor defined as SEQ ID NO: 9: A69L, A73L, A86L, A90L, H103A, V165A, E166A, G215A, V229A, M250A, I253A, A177L, R183A, I260A, T279A, T294A, G306A, L308A, V309A, L310A, V313A, F342A, F358A, V360A, S362A, N370A, S373A, F380A, A385L, P389A, G390A, or R395A.

2. A mutant GPCR according to claim 1, which is in a solubilized form.

3. A mutant GPCR according to claim 1, which is immobilized to a solid support.

* * * * *

```
SEQUENCE LISTING

<160> NUMBER OF SEQ ID NOS: 11

<210> SEQ ID NO 1
<211> LENGTH: 483
<212> TYPE: PRT
<213> ORGANISM: Meleagris gallopavo

<400> SEQUENCE: 1

Met Gly Asp Gly Trp Leu Pro Pro Asp Cys Gly Pro His Asn Arg Ser
1               5                   10                  15

Gly Gly Gly Gly Ala Thr Ala Ala Pro Thr Gly Ser Arg Gln Val Ser
            20                  25                  30

Ala Glu Leu Leu Ser Gln Gln Trp Glu Ala Gly Met Ser Leu Leu Met
        35                  40                  45

Ala Leu Val Val Leu Leu Ile Val Ala Gly Asn Val Leu Val Ile Ala
    50                  55                  60

Ala Ile Gly Arg Thr Gln Arg Leu Gln Thr Leu Thr Asn Leu Phe Ile
65                  70                  75                  80

Thr Ser Leu Ala Cys Ala Asp Leu Val Met Gly Leu Leu Val Val Pro
                85                  90                  95

Phe Gly Ala Thr Leu Val Val Arg Gly Thr Trp Leu Trp Gly Ser Phe
            100                 105                 110

Leu Cys Glu Cys Trp Thr Ser Leu Asp Val Leu Cys Val Thr Ala Ser
        115                 120                 125

Ile Glu Thr Leu Cys Val Ile Ala Ile Asp Arg Tyr Leu Ala Ile Thr
    130                 135                 140

Ser Pro Phe Arg Tyr Gln Ser Leu Met Thr Arg Ala Arg Ala Lys Val
145                 150                 155                 160
```

```
Ile Ile Cys Thr Val Trp Ala Ile Ser Ala Leu Val Ser Phe Leu Pro
                165                 170                 175

Ile Met Met His Trp Trp Arg Asp Glu Asp Pro Gln Ala Leu Lys Cys
            180                 185                 190

Tyr Gln Asp Pro Gly Cys Cys Asp Phe Val Thr Asn Arg Ala Tyr Ala
        195                 200                 205

Ile Ala Ser Ser Ile Ile Ser Phe Tyr Ile Pro Leu Leu Ile Met Ile
    210                 215                 220

Phe Val Tyr Leu Arg Val Tyr Arg Glu Ala Lys Glu Gln Ile Arg Lys
225                 230                 235                 240

Ile Asp Arg Cys Glu Gly Arg Phe Tyr Gly Ser Gln Glu Gln Pro Gln
                245                 250                 255

Pro Pro Pro Leu Pro Gln His Gln Pro Ile Leu Gly Asn Gly Arg Ala
            260                 265                 270

Ser Lys Arg Lys Thr Ser Arg Val Met Ala Met Arg Glu His Lys Ala
        275                 280                 285

Leu Lys Thr Leu Gly Ile Ile Met Gly Val Phe Thr Leu Cys Trp Leu
    290                 295                 300

Pro Phe Phe Leu Val Asn Ile Val Asn Val Phe Asn Arg Asp Leu Val
305                 310                 315                 320

Pro Asp Trp Leu Phe Val Phe Phe Asn Trp Leu Gly Tyr Ala Asn Ser
                325                 330                 335

Ala Phe Asn Pro Ile Ile Tyr Cys Arg Ser Pro Asp Phe Arg Lys Ala
            340                 345                 350

Phe Lys Arg Leu Leu Cys Phe Pro Arg Lys Ala Asp Arg Arg Leu His
        355                 360                 365

Ala Gly Gly Gln Pro Ala Pro Leu Pro Gly Gly Phe Ile Ser Thr Leu
    370                 375                 380

Gly Ser Pro Glu His Ser Pro Gly Gly Thr Trp Ser Asp Cys Asn Gly
385                 390                 395                 400

Gly Thr Arg Gly Gly Ser Glu Ser Ser Leu Glu Glu Arg His Ser Lys
                405                 410                 415

Thr Ser Arg Ser Glu Ser Lys Met Glu Arg Glu Lys Asn Ile Leu Ala
            420                 425                 430

Thr Thr Arg Phe Tyr Cys Thr Phe Leu Gly Asn Gly Asp Lys Ala Val
        435                 440                 445

Phe Cys Thr Val Leu Arg Ile Val Lys Leu Phe Glu Asp Ala Thr Cys
    450                 455                 460

Thr Cys Pro His Thr His Lys Leu Lys Met Lys Trp Arg Phe Lys Gln
465                 470                 475                 480

His Gln Ala

<210> SEQ ID NO 2
<211> LENGTH: 477
<212> TYPE: PRT
<213> ORGANISM: Homo sapiens

<400> SEQUENCE: 2

Met Gly Ala Gly Val Leu Val Leu Gly Ala Ser Glu Pro Gly Asn Leu
1               5                   10                  15

Ser Ser Ala Ala Pro Leu Pro Asp Gly Ala Ala Thr Ala Ala Arg Leu
            20                  25                  30

Leu Val Pro Ala Ser Pro Pro Ala Ser Leu Leu Pro Pro Ala Ser Glu
        35                  40                  45
```

```
Ser Pro Glu Pro Leu Ser Gln Gln Trp Thr Ala Gly Met Gly Leu Leu
    50                  55                  60
Met Ala Leu Ile Val Leu Ile Val Ala Gly Asn Val Leu Val Ile
65                  70                  75                  80
Val Ala Ile Ala Lys Thr Pro Arg Leu Gln Thr Leu Thr Asn Leu Phe
                85                  90                  95
Ile Met Ser Leu Ala Ser Ala Asp Leu Val Met Gly Leu Leu Val Val
            100                 105                 110
Pro Phe Gly Ala Thr Ile Val Val Trp Gly Arg Trp Glu Tyr Gly Ser
        115                 120                 125
Phe Phe Cys Glu Leu Trp Thr Ser Val Asp Val Leu Cys Val Thr Ala
    130                 135                 140
Ser Ile Glu Thr Leu Cys Val Ile Ala Leu Asp Arg Tyr Leu Ala Ile
145                 150                 155                 160
Thr Ser Pro Phe Arg Tyr Gln Ser Leu Leu Thr Arg Ala Arg Ala Arg
                165                 170                 175
Gly Leu Val Cys Thr Val Trp Ala Ile Ser Ala Leu Val Ser Phe Leu
            180                 185                 190
Pro Ile Leu Met His Trp Trp Arg Ala Glu Ser Asp Glu Ala Arg Arg
        195                 200                 205
Cys Tyr Asn Asp Pro Lys Cys Cys Asp Phe Val Thr Asn Arg Ala Tyr
    210                 215                 220
Ala Ile Ala Ser Ser Val Val Ser Phe Tyr Val Pro Leu Cys Ile Met
225                 230                 235                 240
Ala Phe Val Tyr Leu Arg Val Phe Arg Glu Ala Gln Lys Gln Val Lys
                245                 250                 255
Lys Ile Asp Ser Cys Glu Arg Arg Phe Leu Gly Gly Pro Ala Arg Pro
            260                 265                 270
Pro Ser Pro Ser Pro Ser Pro Val Pro Ala Pro Ala Pro Pro Pro Gly
        275                 280                 285
Pro Pro Arg Pro Ala Ala Ala Ala Thr Ala Pro Leu Ala Asn Gly
    290                 295                 300
Arg Ala Gly Lys Arg Arg Pro Ser Arg Leu Val Ala Leu Arg Glu Gln
305                 310                 315                 320
Lys Ala Leu Lys Thr Leu Gly Ile Ile Met Gly Val Phe Thr Leu Cys
                325                 330                 335
Trp Leu Pro Phe Phe Leu Ala Asn Val Val Lys Ala Phe His Arg Glu
            340                 345                 350
Leu Val Pro Asp Arg Leu Phe Val Phe Phe Asn Trp Leu Gly Tyr Ala
        355                 360                 365
Asn Ser Ala Phe Asn Pro Ile Ile Tyr Cys Arg Ser Pro Asp Phe Arg
    370                 375                 380
Lys Ala Phe Gln Gly Leu Leu Cys Cys Ala Arg Arg Ala Ala Arg Arg
385                 390                 395                 400
Arg His Ala Thr His Gly Asp Arg Pro Arg Ala Ser Gly Cys Leu Ala
                405                 410                 415
Arg Pro Gly Pro Pro Pro Ser Pro Gly Ala Ala Ser Asp Asp Asp Asp
            420                 425                 430
Asp Asp Val Val Gly Ala Thr Pro Pro Ala Arg Leu Leu Glu Pro Trp
        435                 440                 445
Ala Gly Cys Asn Gly Gly Ala Ala Ala Asp Ser Asp Ser Ser Leu Asp
    450                 455                 460
```

Glu Pro Cys Arg Pro Gly Phe Ala Ser Glu Ser Lys Val
465                 470                 475

<210> SEQ ID NO 3
<211> LENGTH: 413
<212> TYPE: PRT
<213> ORGANISM: Homo sapiens

<400> SEQUENCE: 3

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
        355                 360                 365

Glu Gln Glu Lys Glu Asn Lys Leu Leu Cys Glu Asp Leu Pro Gly Thr
        370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410

<210> SEQ ID NO 4
<211> LENGTH: 408
<212> TYPE: PRT
<213> ORGANISM: Homo sapiens

<400> SEQUENCE: 4

Met Ala Pro Trp Pro His Glu Asn Ser Ser Leu Ala Pro Trp Pro Asp
1               5                   10                  15

Leu Pro Thr Leu Ala Pro Asn Thr Ala Asn Thr Ser Gly Leu Pro Gly
                20                  25                  30

Val Pro Trp Glu Ala Ala Leu Ala Gly Ala Leu Leu Ala Leu Ala Val
            35                  40                  45

Leu Ala Thr Val Gly Gly Asn Leu Leu Val Ile Val Ala Ile Ala Trp
50                  55                  60

Thr Pro Arg Leu Gln Thr Met Thr Asn Val Phe Val Thr Ser Leu Ala
65                  70                  75                  80

Ala Ala Asp Leu Val Met Gly Leu Leu Val Val Pro Pro Ala Ala Thr
                85                  90                  95

Leu Ala Leu Thr Gly His Trp Pro Leu Gly Ala Thr Gly Cys Glu Leu
                100                 105                 110

Trp Thr Ser Val Asp Val Leu Cys Val Thr Ala Ser Ile Glu Thr Leu
            115                 120                 125

Cys Ala Leu Ala Val Asp Arg Tyr Leu Ala Val Thr Asn Pro Leu Arg
130                 135                 140

Tyr Gly Ala Leu Val Thr Lys Arg Cys Ala Arg Thr Ala Val Val Leu
145                 150                 155                 160

Val Trp Val Val Ser Ala Ala Val Ser Phe Ala Pro Ile Met Ser Gln
                165                 170                 175

Trp Trp Arg Val Gly Ala Asp Ala Glu Ala Gln Arg Cys His Ser Asn
            180                 185                 190

Pro Arg Cys Cys Ala Phe Ala Ser Asn Met Pro Tyr Val Leu Leu Ser
        195                 200                 205

Ser Ser Val Ser Phe Tyr Leu Pro Leu Leu Val Met Leu Phe Val Tyr
210                 215                 220

Ala Arg Val Phe Val Val Ala Thr Arg Gln Leu Arg Leu Leu Arg Gly
225                 230                 235                 240

Glu Leu Gly Arg Phe Pro Pro Glu Glu Ser Pro Pro Ala Pro Ser Arg
                245                 250                 255

Ser Leu Ala Pro Ala Pro Val Gly Thr Cys Ala Pro Pro Glu Gly Val
            260                 265                 270

Pro Ala Cys Gly Arg Arg Pro Ala Arg Leu Leu Pro Leu Arg Glu His
        275                 280                 285

Arg Ala Leu Cys Thr Leu Gly Leu Ile Met Gly Thr Phe Thr Leu Cys
290                 295                 300

Trp Leu Pro Phe Phe Leu Ala Asn Val Leu Arg Ala Leu Gly Gly Pro
305                 310                 315                 320

```
Ser Leu Val Pro Gly Pro Ala Phe Leu Ala Leu Asn Trp Leu Gly Tyr
            325                 330                 335

Ala Asn Ser Ala Phe Asn Pro Leu Ile Tyr Cys Arg Ser Pro Asp Phe
            340                 345                 350

Arg Ser Ala Phe Arg Arg Leu Leu Cys Arg Cys Gly Arg Arg Leu Pro
            355                 360                 365

Pro Glu Pro Cys Ala Ala Arg Pro Ala Leu Phe Pro Ser Gly Val
370                 375                 380

Pro Ala Ala Arg Ser Ser Pro Ala Gln Pro Arg Leu Cys Gln Arg Leu
385                 390                 395                 400

Asp Gly Ala Ser Trp Gly Val Ser
            405

<210> SEQ ID NO 5
<211> LENGTH: 412
<212> TYPE: PRT
<213> ORGANISM: Homo sapiens

<400> SEQUENCE: 5

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
    50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
        195                 200                 205

Lys Gln Met Glu Ser Gln Pro Leu Pro Gly Glu Arg Ala Arg Ser Thr
    210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
                245                 250                 255

Phe Phe Cys Pro Asp Cys Ser His Ala Pro Leu Trp Leu Met Tyr Leu
            260                 265                 270
```

```
Ala Ile Val Leu Ser His Thr Asn Ser Val Asn Pro Phe Ile Tyr
        275                 280                 285

Ala Tyr Arg Ile Arg Glu Phe Arg Gln Thr Phe Arg Lys Ile Ile Arg
    290                 295                 300

Ser His Val Leu Arg Gln Gln Glu Pro Phe Lys Ala Ala Gly Thr Ser
305                 310                 315                 320

Ala Arg Val Leu Ala Ala His Gly Ser Asp Gly Glu Gln Val Ser Leu
                325                 330                 335

Arg Leu Asn Gly His Pro Pro Gly Val Trp Ala Asn Gly Ser Ala Pro
                340                 345                 350

His Pro Glu Arg Arg Pro Asn Gly Tyr Ala Leu Gly Leu Val Ser Gly
            355                 360                 365

Gly Ser Ala Gln Glu Ser Gln Gly Asn Thr Gly Leu Pro Asp Val Glu
370                 375                 380

Leu Leu Ser His Glu Leu Lys Gly Val Cys Pro Glu Pro Pro Gly Leu
385                 390                 395                 400

Asp Asp Pro Leu Ala Gln Asp Gly Ala Gly Val Ser
                405                 410

<210> SEQ ID NO 6
<211> LENGTH: 332
<212> TYPE: PRT
<213> ORGANISM: Homo sapiens

<400> SEQUENCE: 6

Met Leu Leu Glu Thr Gln Asp Ala Leu Tyr Val Ala Leu Glu Leu Val
1               5                   10                  15

Ile Ala Ala Leu Ser Val Ala Gly Asn Val Leu Val Cys Ala Ala Val
                20                  25                  30

Gly Thr Ala Asn Thr Leu Gln Thr Pro Thr Asn Tyr Phe Leu Val Ser
            35                  40                  45

Leu Ala Ala Ala Asp Val Ala Val Gly Leu Phe Ala Ile Pro Phe Ala
    50                  55                  60

Ile Thr Ile Ser Leu Gly Phe Cys Thr Asp Phe Tyr Gly Cys Leu Phe
65                  70                  75                  80

Leu Ala Cys Phe Val Leu Val Leu Thr Gln Ser Ser Ile Phe Ser Leu
                85                  90                  95

Leu Ala Val Ala Val Asp Arg Tyr Leu Ala Ile Cys Val Pro Leu Arg
            100                 105                 110

Tyr Lys Ser Leu Val Thr Gly Thr Arg Ala Arg Gly Val Ile Ala Val
    115                 120                 125

Leu Trp Val Leu Ala Phe Gly Ile Gly Leu Thr Pro Phe Leu Gly Trp
130                 135                 140

Asn Ser Lys Asp Ser Ala Thr Asn Asn Cys Thr Glu Pro Trp Asp Gly
145                 150                 155                 160

Thr Thr Asn Glu Ser Cys Cys Leu Val Lys Cys Leu Phe Glu Asn Val
                165                 170                 175

Val Pro Met Ser Tyr Met Val Tyr Phe Asn Phe Phe Gly Cys Val Leu
            180                 185                 190

Pro Pro Leu Leu Ile Met Leu Val Ile Tyr Ile Lys Ile Phe Leu Val
    195                 200                 205

Ala Cys Arg Gln Leu Gln Arg Thr Glu Leu Met Asp His Ser Arg Thr
210                 215                 220
```

```
Thr Leu Gln Arg Glu Ile His Ala Ala Lys Ser Leu Ala Met Ile Val
225                 230                 235                 240

Gly Ile Phe Ala Leu Cys Trp Leu Pro Val His Ala Val Asn Cys Val
                245                 250                 255

Thr Leu Phe Gln Pro Ala Gln Gly Lys Asn Lys Pro Lys Trp Ala Met
            260                 265                 270

Asn Met Ala Ile Leu Leu Ser His Ala Asn Ser Val Val Asn Pro Ile
                275                 280                 285

Val Tyr Ala Tyr Arg Asn Arg Asp Phe Arg Tyr Thr Phe His Lys Ile
            290                 295                 300

Ile Ser Arg Tyr Leu Leu Cys Gln Ala Asp Val Lys Ser Gly Asn Gly
305                 310                 315                 320

Gln Ala Gly Val Gln Pro Ala Leu Gly Val Gly Leu
                325                 330
```

<210> SEQ ID NO 7
<211> LENGTH: 318
<212> TYPE: PRT
<213> ORGANISM: Homo sapiens

<400> SEQUENCE: 7

```
Met Pro Asn Asn Ser Thr Ala Leu Ser Leu Ala Asn Val Thr Tyr Ile
1               5                   10                  15

Thr Met Glu Ile Phe Ile Gly Leu Cys Ala Ile Val Gly Asn Val Leu
                20                  25                  30

Val Ile Cys Val Val Lys Leu Asn Pro Ser Leu Gln Thr Thr Thr Phe
            35                  40                  45

Tyr Phe Ile Val Ser Leu Ala Leu Ala Asp Ile Ala Val Gly Val Leu
        50                  55                  60

Val Met Pro Leu Ala Ile Val Val Ser Leu Gly Ile Thr Ile His Phe
65                  70                  75                  80

Tyr Ser Cys Leu Phe Met Thr Cys Leu Leu Leu Ile Phe Thr His Ala
                85                  90                  95

Ser Ile Met Ser Leu Leu Ala Ile Ala Val Asp Arg Tyr Leu Arg Val
                100                 105                 110

Lys Leu Thr Val Arg Tyr Lys Arg Val Thr Thr His Arg Arg Ile Trp
            115                 120                 125

Leu Ala Leu Gly Leu Cys Trp Leu Val Ser Phe Leu Val Gly Leu Thr
        130                 135                 140

Pro Met Phe Gly Trp Asn Met Lys Leu Thr Ser Glu Tyr His Arg Asn
145                 150                 155                 160

Val Thr Phe Leu Ser Cys Gln Phe Val Ser Val Met Arg Met Asp Tyr
                165                 170                 175

Met Val Tyr Phe Ser Phe Leu Thr Trp Ile Phe Ile Pro Leu Val Val
            180                 185                 190

Met Cys Ala Ile Tyr Leu Asp Ile Phe Tyr Ile Ile Arg Asn Lys Leu
        195                 200                 205

Ser Leu Asn Leu Ser Asn Ser Lys Glu Thr Gly Ala Phe Tyr Gly Arg
            210                 215                 220

Glu Phe Lys Thr Ala Lys Ser Leu Phe Leu Val Leu Phe Leu Phe Ala
225                 230                 235                 240

Leu Ser Trp Leu Pro Leu Ser Ile Ile Asn Cys Ile Ile Tyr Phe Asn
                245                 250                 255
```

Gly Glu Val Pro Gln Leu Val Leu Tyr Met Gly Ile Leu Leu Ser His
                260                 265                 270

Ala Asn Ser Met Met Asn Pro Ile Val Tyr Ala Tyr Lys Ile Lys Lys
            275                 280                 285

Phe Lys Glu Thr Tyr Leu Leu Ile Leu Lys Ala Cys Val Val Cys His
290                 295                 300

Pro Ser Asp Ser Leu Asp Thr Ser Ile Glu Lys Asn Ser Glu
305                 310                 315

<210> SEQ ID NO 8
<211> LENGTH: 326
<212> TYPE: PRT
<213> ORGANISM: Homo sapiens

<400> SEQUENCE: 8

Met Pro Pro Ser Ile Ser Ala Phe Gln Ala Ala Tyr Ile Gly Ile Glu
1               5                   10                  15

Val Leu Ile Ala Leu Val Ser Val Pro Gly Asn Val Leu Val Ile Trp
            20                  25                  30

Ala Val Lys Val Asn Gln Ala Leu Arg Asp Ala Thr Phe Cys Phe Ile
        35                  40                  45

Val Ser Leu Ala Val Ala Asp Val Ala Val Gly Ala Leu Val Ile Pro
    50                  55                  60

Leu Ala Ile Leu Ile Asn Ile Gly Pro Gln Thr Tyr Phe His Thr Cys
65                  70                  75                  80

Leu Met Val Ala Cys Pro Val Leu Ile Leu Thr Gln Ser Ser Ile Leu
                85                  90                  95

Ala Leu Leu Ala Ile Ala Val Asp Arg Tyr Leu Arg Val Lys Ile Pro
            100                 105                 110

Leu Arg Tyr Lys Met Val Val Thr Pro Arg Arg Ala Ala Val Ala Ile
        115                 120                 125

Ala Gly Cys Trp Ile Leu Ser Phe Val Val Gly Leu Thr Pro Met Phe
    130                 135                 140

Gly Trp Asn Asn Leu Ser Ala Val Glu Arg Ala Trp Ala Ala Asn Gly
145                 150                 155                 160

Ser Met Gly Glu Pro Val Ile Lys Cys Glu Phe Glu Lys Val Ile Ser
                165                 170                 175

Met Glu Tyr Met Val Tyr Phe Asn Phe Phe Val Trp Val Leu Pro Pro
            180                 185                 190

Leu Leu Leu Met Val Leu Ile Tyr Leu Glu Val Phe Tyr Leu Ile Arg
        195                 200                 205

Lys Gln Leu Asn Lys Lys Val Ser Ala Ser Ser Gly Asp Pro Gln Lys
    210                 215                 220

Tyr Tyr Gly Lys Glu Leu Lys Ile Ala Lys Ser Leu Ala Leu Ile Leu
225                 230                 235                 240

Phe Leu Phe Ala Leu Ser Trp Leu Pro Leu His Ile Leu Asn Cys Ile
                245                 250                 255

Thr Leu Phe Cys Pro Ser Cys His Lys Pro Ser Ile Leu Thr Tyr Ile
            260                 265                 270

Ala Ile Phe Leu Thr His Gly Asn Ser Ala Met Asn Pro Ile Val Tyr
        275                 280                 285

Ala Phe Arg Ile Gln Lys Phe Arg Val Thr Phe Leu Lys Ile Trp Asn
    290                 295                 300

-continued

Asp His Phe Arg Cys Gln Pro Ala Pro Pro Ile Asp Glu Asp Leu Pro
305                 310                 315                 320

Glu Glu Arg Pro Asp Asp
                325

<210> SEQ ID NO 9
<211> LENGTH: 424
<212> TYPE: PRT
<213> ORGANISM: Rattus norvegicus

<400> SEQUENCE: 9

Met His Leu Asn Ser Ser Val Pro Gln Gly Thr Pro Gly Glu Pro Asp
1               5                   10                  15

Ala Gln Pro Phe Ser Gly Pro Gln Ser Glu Met Glu Ala Thr Phe Leu
                20                  25                  30

Ala Leu Ser Leu Ser Asn Gly Ser Gly Asn Thr Ser Glu Ser Asp Thr
            35                  40                  45

Ala Gly Pro Asn Ser Asp Leu Asp Val Asn Thr Asp Ile Tyr Ser Lys
        50                  55                  60

Val Leu Val Thr Ala Ile Tyr Leu Ala Leu Phe Val Val Gly Thr Val
65                  70                  75                  80

Gly Asn Ser Val Thr Ala Phe Thr Leu Ala Arg Lys Lys Ser Leu Gln
                85                  90                  95

Ser Leu Gln Ser Thr Val His Tyr His Leu Gly Ser Leu Ala Leu Ser
            100                 105                 110

Asp Leu Leu Ile Leu Leu Leu Ala Met Pro Val Glu Leu Tyr Asn Phe
        115                 120                 125

Ile Trp Val His His Pro Trp Ala Phe Gly Asp Ala Gly Cys Arg Gly
130                 135                 140

Tyr Tyr Phe Leu Arg Asp Ala Cys Thr Tyr Ala Thr Ala Leu Asn Val
145                 150                 155                 160

Ala Ser Leu Ser Val Glu Arg Tyr Leu Ala Ile Cys His Pro Phe Lys
                165                 170                 175

Ala Lys Thr Leu Met Ser Arg Ser Arg Thr Lys Lys Phe Ile Ser Ala
            180                 185                 190

Ile Trp Leu Ala Ser Ala Leu Leu Ala Ile Pro Met Leu Phe Thr Met
        195                 200                 205

Gly Leu Gln Asn Arg Ser Gly Asp Gly Thr His Pro Gly Gly Leu Val
210                 215                 220

Cys Thr Pro Ile Val Asp Thr Ala Thr Val Lys Val Val Ile Gln Val
225                 230                 235                 240

Asn Thr Phe Met Ser Phe Leu Phe Pro Met Leu Val Ile Ser Ile Leu
                245                 250                 255

Asn Thr Val Ile Ala Asn Lys Leu Thr Val Met Val His Gln Ala Ala
            260                 265                 270

Glu Gln Gly Arg Val Cys Thr Val Gly Thr His Asn Gly Leu Glu His
        275                 280                 285

Ser Thr Phe Asn Met Thr Ile Glu Pro Gly Arg Val Gln Ala Leu Arg
290                 295                 300

His Gly Val Leu Val Leu Arg Ala Val Val Ile Ala Phe Val Val Cys
305                 310                 315                 320

Trp Leu Pro Tyr His Val Arg Arg Leu Met Phe Cys Tyr Ile Ser Asp
                325                 330                 335

```
Glu Gln Trp Thr Thr Phe Leu Phe Asp Phe Tyr His Tyr Phe Tyr Met
            340                 345                 350

Leu Thr Asn Ala Leu Phe Tyr Val Ser Ser Ala Ile Asn Pro Ile Leu
            355                 360                 365

Tyr Asn Leu Val Ser Ala Asn Phe Arg Gln Val Phe Leu Ser Thr Leu
        370                 375                 380

Ala Cys Leu Cys Pro Gly Trp Arg His Arg Lys Lys Arg Pro Thr
385                 390                 395                 400

Phe Ser Arg Lys Pro Asn Ser Met Ser Ser Asn His Ala Phe Ser Thr
                405                 410                 415

Ser Ala Thr Arg Glu Thr Leu Tyr
            420

<210> SEQ ID NO 10
<211> LENGTH: 418
<212> TYPE: PRT
<213> ORGANISM: Homo sapiens

<400> SEQUENCE: 10

Met Arg Leu Asn Ser Ser Ala Pro Gly Thr Pro Gly Thr Pro Ala Ala
1               5                   10                  15

Asp Pro Phe Gln Arg Ala Gln Ala Gly Leu Glu Glu Ala Leu Leu Ala
            20                  25                  30

Pro Gly Phe Gly Asn Ala Ser Gly Asn Ala Ser Glu Arg Val Leu Ala
        35                  40                  45

Ala Pro Ser Ser Glu Leu Asp Val Asn Thr Asp Ile Tyr Ser Lys Val
50                  55                  60

Leu Val Thr Ala Val Tyr Leu Ala Leu Phe Val Val Gly Thr Val Gly
65                  70                  75                  80

Asn Thr Val Thr Ala Phe Thr Leu Ala Arg Lys Lys Ser Leu Gln Ser
            85                  90                  95

Leu Gln Ser Thr Val His Tyr His Leu Gly Ser Leu Ala Leu Ser Asp
            100                 105                 110

Leu Leu Thr Leu Leu Leu Ala Met Pro Val Glu Leu Tyr Asn Phe Ile
            115                 120                 125

Trp Val His His Pro Trp Ala Phe Gly Asp Ala Gly Cys Arg Gly Tyr
        130                 135                 140

Tyr Phe Leu Arg Asp Ala Cys Thr Tyr Ala Thr Ala Leu Asn Val Ala
145                 150                 155                 160

Ser Leu Ser Val Glu Arg Tyr Leu Ala Ile Cys His Pro Phe Lys Ala
                165                 170                 175

Lys Thr Leu Met Ser Arg Ser Arg Thr Lys Lys Phe Ile Ser Ala Ile
            180                 185                 190

Trp Leu Ala Ser Ala Leu Leu Ala Val Pro Met Leu Phe Thr Met Gly
        195                 200                 205

Glu Gln Asn Arg Ser Ala Asp Gly Gln His Ala Gly Gly Leu Val Cys
210                 215                 220

Thr Pro Thr Ile His Thr Ala Thr Val Lys Val Val Ile Gln Val Asn
225                 230                 235                 240

Thr Phe Met Ser Phe Ile Phe Pro Met Val Val Ile Ser Val Leu Asn
            245                 250                 255

Thr Ile Ile Ala Asn Lys Leu Thr Val Met Val Arg Gln Ala Ala Glu
            260                 265                 270
```

```
Gln Gly Gln Val Cys Thr Val Gly Gly Glu His Ser Thr Phe Ser Met
            275                 280                 285

Ala Ile Glu Pro Gly Arg Val Gln Ala Leu Arg His Gly Val Arg Val
290                 295                 300

Leu Arg Ala Val Val Ile Ala Phe Val Val Cys Trp Leu Pro Tyr His
305                 310                 315                 320

Val Arg Arg Leu Met Phe Cys Tyr Ile Ser Asp Glu Gln Trp Thr Pro
            325                 330                 335

Phe Leu Tyr Asp Phe Tyr His Tyr Phe Tyr Met Val Thr Asn Ala Leu
            340                 345                 350

Phe Tyr Val Ser Ser Thr Ile Asn Pro Ile Leu Tyr Asn Leu Val Ser
            355                 360                 365

Ala Asn Phe Arg His Ile Phe Leu Ala Thr Leu Ala Cys Leu Cys Pro
            370                 375                 380

Val Trp Arg Arg Arg Lys Arg Pro Ala Phe Ser Arg Lys Ala Asp
385                 390                 395                 400

Ser Val Ser Ser Asn His Thr Leu Ser Ser Asn Ala Thr Arg Glu Thr
            405                 410                 415

Leu Tyr

<210> SEQ ID NO 11
<211> LENGTH: 409
<212> TYPE: PRT
<213> ORGANISM: Homo sapiens

<400> SEQUENCE: 11

Met Glu Thr Ser Ser Pro Arg Pro Pro Arg Pro Ser Ser Asn Pro Gly
1               5                   10                  15

Leu Ser Leu Asp Ala Arg Leu Gly Val Asp Thr Arg Leu Trp Ala Lys
            20                  25                  30

Val Leu Phe Thr Ala Leu Tyr Ala Leu Ile Trp Ala Leu Gly Ala Ala
        35                  40                  45

Gly Asn Ala Leu Ser Val His Val Val Leu Lys Ala Arg Ala Gly Arg
    50                  55                  60

Ala Gly Arg Leu Arg His His Val Leu Ser Leu Ala Leu Ala Gly Leu
65                  70                  75                  80

Leu Leu Leu Leu Val Gly Val Pro Val Glu Leu Tyr Ser Phe Val Trp
                85                  90                  95

Phe His Tyr Pro Trp Val Phe Gly Asp Leu Gly Cys Arg Gly Tyr Tyr
            100                 105                 110

Phe Val His Glu Leu Cys Ala Tyr Ala Thr Val Leu Ser Val Ala Gly
        115                 120                 125

Leu Ser Ala Glu Arg Cys Leu Ala Val Cys Gln Pro Leu Arg Ala Arg
    130                 135                 140

Ser Leu Leu Thr Pro Arg Arg Thr Arg Trp Leu Val Ala Leu Ser Trp
145                 150                 155                 160

Ala Ala Ser Leu Gly Leu Ala Leu Pro Met Ala Val Ile Met Gly Gln
                165                 170                 175

Lys His Glu Leu Glu Thr Ala Asp Gly Glu Pro Glu Pro Ala Ser Arg
            180                 185                 190

Val Cys Thr Val Leu Val Ser Arg Thr Ala Leu Gln Val Phe Ile Gln
        195                 200                 205

Val Asn Val Leu Val Ser Phe Val Leu Pro Leu Ala Leu Thr Ala Phe
    210                 215                 220
```

```
Leu Asn Gly Val Thr Val Ser His Leu Leu Ala Leu Cys Ser Gln Val
225                 230                 235                 240

Pro Ser Thr Ser Thr Pro Gly Ser Ser Thr Pro Ser Arg Leu Glu Leu
                245                 250                 255

Leu Ser Glu Glu Gly Leu Leu Ser Phe Ile Val Trp Lys Lys Thr Phe
            260                 265                 270

Ile Gln Gly Gly Gln Val Ser Leu Val Arg His Lys Asp Val Arg Arg
        275                 280                 285

Ile Arg Ser Leu Gln Arg Ser Val Gln Val Leu Arg Ala Ile Val Val
    290                 295                 300

Met Tyr Val Ile Cys Trp Leu Pro Tyr His Ala Arg Arg Leu Met Tyr
305                 310                 315                 320

Cys Tyr Val Pro Asp Asp Ala Trp Thr Asp Pro Leu Tyr Asn Phe Tyr
                325                 330                 335

His Tyr Phe Tyr Met Val Thr Asn Thr Leu Phe Tyr Val Ser Ser Ala
            340                 345                 350

Val Thr Pro Leu Leu Tyr Asn Ala Val Ser Ser Ser Phe Arg Lys Leu
    355                 360                 365

Phe Leu Glu Ala Val Ser Ser Leu Cys Gly Glu His His Pro Met Lys
    370                 375                 380

Arg Leu Pro Pro Lys Pro Gln Ser Pro Thr Leu Met Asp Thr Ala Ser
385                 390                 395                 400

Gly Phe Gly Asp Pro Pro Glu Thr Arg
                405
```